(12) United States Patent
Tang et al.

(10) Patent No.: US 11,944,682 B2
(45) Date of Patent: Apr. 2, 2024

(54) AGGREGATION INDUCED EMISSION-BACTERIOPHAGE BIOCONJUGATES

(71) Applicant: The Hong Kong University of Science and Technology, Hong Kong (CN)

(72) Inventors: Benzhong Tang, Hong Kong (CN); Xuewen He, Hong Kong (CN)

(73) Assignee: The Hong Kong University of Science and Technologyy, Hong Kong (CN)

(*) Notice: Subject to any disclaimer, the term of this patent is extended or adjusted under 35 U.S.C. 154(b) by 462 days.

(21) Appl. No.: 17/248,369

(22) Filed: Jan. 22, 2021

(65) Prior Publication Data
US 2021/0228721 A1 Jul. 29, 2021

Related U.S. Application Data

(60) Provisional application No. 62/995,297, filed on Jan. 24, 2020.

(51) Int. Cl.
| | | |
|---|---|---|
| *A61K 41/00* | (2020.01) | |
| *A61B 5/00* | (2006.01) | |
| *A61K 47/69* | (2017.01) | |
| *A61N 5/06* | (2006.01) | |
| *A61P 31/04* | (2006.01) | |
| *C07D 401/12* | (2006.01) | |
| *C12N 7/00* | (2006.01) | |
| *C12Q 1/04* | (2006.01) | |
| *G01N 21/64* | (2006.01) | |

(52) U.S. Cl.
CPC ...... *A61K 41/0057* (2013.01); *A61K 47/6901* (2017.08); *A61N 5/062* (2013.01); *A61N 5/0624* (2013.01); *A61P 31/04* (2018.01); *C07D 401/12* (2013.01); *C12N 7/00* (2013.01); *C12Q 1/04* (2013.01); *G01N 21/6428* (2013.01); *G01N 21/6458* (2013.01); *A61B 5/0071* (2013.01); *A61N 2005/0662* (2013.01); *C12N 2795/10032* (2013.01); *G01N 2021/6439* (2013.01)

(58) Field of Classification Search
None
See application file for complete search history.

(56) References Cited

FOREIGN PATENT DOCUMENTS

CN 110151994 A * 8/2019

OTHER PUBLICATIONS

Wang et al., Food and Agricultural Immunology, Nov. 14, 2019, 30(1):1303-1317. (Year: 2019).*
Zhang et al., Biosensors and Bioelectronics, Apr. 17, 2019, 135:173-180. (Year: 2019).*
Liu, X.; Li, M.; Han, T.; Cao, B.; Qiu, Z.; Li, Y.; Li, Q.; Hu, Y.; Liu, Z.; Lam, J. W. Y.; et al. In Situ Generation of Azonia Containing Polyelectrolytes for Luminescent Photopatterning and Superbug Killing. J. Am. Chem. Soc. 2019, 141, 11259-11268.
Kang, M.; Kwok, R. T. K.; Wang, J.; Zhang, H.; Lam, J. W. Y.; Li, Y.; Zhang, P.; Zou, H.; Gu, X.; Li, F.; et al. A Multifunctional Luminogen with Aggregation-Induced Emission Characteristics for Selective Imaging and Photodynamic Killing of both Cancer Cells and Gram-Positive Bacteria. J. Mater. Chem. B 2018, 6, 3894-3903.
Kang, M.; Zhou, C.; Wu, S.; Yu, B.; Zhang, Z.; Song, N.; Lee, M. M. S.; Xu, W.; Xu, F.-J.; Wang, D.; et al. Evaluation of Structure-Function Relationships of Aggregation-Induced Emission Luminogens for Simultaneous Dual Applications of Specific Discrimination and Efficient Photodynamic Killing of Gram-Positive Bacteria. J. Am. Chem. Soc. 2019, 141, 16781-16789.
Li, Y.; Zhao, Z.; Zhang, J.; Kwok, R. T. K.; Xie, S.; Tang, R.; Jia, Y.; Yang, J.; Wang, L.; Lam, J. W. Y.; et al. A Bifunctional Aggregation-Induced Emission Luminogen for Monitoring and Killing of Multidrug-Resistant Bacteria. Adv. Funct. Mater. 2018, 28, 1804632.
Mao, D.; Hu, F.; Ji, S.; Wu, W.; Ding, D.; Kong, D.; Liu, B. Metal-Organic-Framework-Assisted In Vivo Bacterial Metabolic Labeling and Precise Antibacterial Therapy. Adv. Mater. 2018, 30, 1706831.

* cited by examiner

*Primary Examiner* — Nicole Kinsey White
(74) *Attorney, Agent, or Firm* — S&F/WEHRW

(57) ABSTRACT

Aggregation-induced emission-bacteriophage bioconjugate including a bacteriophage covalently bonded to at least one aggregation-induced emission luminogen via an optional linker, pharmaceutical compositions including the same, and methods of preparation and use thereof.

11 Claims, 40 Drawing Sheets

AGGREGATION INDUCED EMISSION-BACTERIOPHAGE BIOCONJUGATES

CROSS-REFERENCE TO RELATED APPLICATIONS

This application claims priority from U.S. Provisional Patent Application No. 62/995,297, filed on Jan. 24, 2020, which is incorporated herein by reference in its entirety.

TECHNICAL FIELD

The present disclosure generally relates to aggregation-induced emission (AIE)-bacteriophage bioconjugates that can integrate the fluorescence monitoring, selective bacterial targeting, and AIE-based photodynamic therapy together towards bacteria, and use of these materials as an in vitro and in vivo antibacterial agent.

BACKGROUND

Bacterial infectious diseases have become one of the greatest global challenges, which seriously threaten the health and civilization of human beings. And increasing evidences revealed that bacteria can also indirectly promote the occurrence and progression of other diseases, such as cancer. On the other hand, bacterial communities are indispensable to human health, such as intestinal microbes whose balances determined the nutrient absorption from digested food in our bodies and should be always protected from unintentional damage. Therefore, in the antibacterial battle, promoting antibacterial agent in terms of targeting and killing efficiency is persistently pursued. Antibiotics have been predominately employed in the treatment of bacterial infections since the discovery of penicillin. However, using antibiotics, even narrow-spectrum antibiotics, both harmful bacteria and beneficial microbes could be killed, resulting side effects such as diarrhea, constipation and inflammatory bowel. The global abuse or overuse of antibiotics has promoted bacterial evolution and intensified the antibiotic resistance. The situation is worsening with the rapidly increased difficulty and cost in producing new robust antibacterial agents. Thus, it is highly desirable to develop pinpoint accurate drugs to kill certain species of harmful pathogens. Fortunately, bacteriophage had been verified with particular specificity to their hosts, and could evolve synchronously to adapt to infect resistant bacteria. Phagotherapy, which was used before antibiotics discovered, is now going through a revival driven by the crisis of antibiotic resistance. However, the bacteriophage alone normally shows moderate antibacterial effect, hindering the curing of infectious diseases especially the acute infections. Due to the lack of imaging moieties, the processes of phagotherapy including target recognition, binding and infection could not be easily monitored, resulting in difficult real-time evaluation of therapeutic performance. The introduction of sensitively detectable "radar" with powerful "weaponry", will therefore promote phagotherapy as a deluxe ensemble for both visualization of its infection process and their subsequent discriminative eradication.

Fluorescence imaging technology has emerged as a rapid, facile and powerful tool for visualization and tracking of bioanalytes with merits of high sensitivity, low cost and fast responsiveness. Surpassing traditional organic fluorophores that have usually suffered severe photobleaching and moderate signal-to-noise ratio, the newly developed luminogens with aggregation-induced emission characteristics (AIEgens) are becoming attractive candidates for advanced biosensing and imaging application. AIEgens display weak emission in solution, but intensified fluorescence upon aggregation via the restriction of intramolecular motion. The unique light-up fluorescence with negligible background noise and remarkable photostability, qualify AIEgens to be a superior choice in long-lasting fluorescence imaging and tracking for dynamic bioprocesses. What's more, with intelligent molecular designing, AIE-based materials display exceptional photodynamic activity for the treatments of malignant cancer and the inactivation of bacteria. However, the specific discrimination of a certain species of bacterium, has not yet been previously demonstrated by AIEgens, making them unsuitable for accurately removing certain targeted bacterium. Although the bioorthogonal method showed improvement in targeted labeling, the incorporation of exogenous reactive groups was demanding with challenges for large-scale applications. These limitations propelled us to engineer AIEgens with pinpoint specificity in order to realize the discriminative imaging and killing of a certain species of bacterium.

SUMMARY

Provided herein are AIE-bacteriophage bioconjugates, which integrate one or more AIEgens with a bacteriophage to form a new class of antimicrobial bioconjugates (exemplified by TVP-PAP) for the imaging and killing of a certain species of bacterium. Bacteriophage targeting *P. aeruginosa* was chosen as a prototype. The exemplary AIE molecule, TVP-S, was designed with excellent fluorescence properties and efficient photodynamic inactivation (PDI) activity. Through a simple amino-carboxyl reaction, the AIEgens could be facilely covalently bonded to the surface of bacteriophage. The generated TVP-PAP advantageously preserved the properties of both AIEgen and bacteriophage, with intrinsic AIE fluorescence serving the function of real-time monitoring of bacteriophage-bacterium interaction and particular specificity in bacterial targeting. What's more, the synergistic antibacterial effect with efficiency that significantly surpassing both individuals in the bioconjugates was achieved by integrating the PDI activity of AIEgen and the infection ability of bacteriophage itself. Superior performance of the bioconjugate was also demonstrated in in vivo treatment of infectious wounds caused by both wild and MDR *P. aeruginosa*.

In a first aspect, provided herein is an aggregation-induced emission (AIE)-bacteriophage bioconjugate comprising a bacteriophage covalently bonded to at least one aggregation-induced emission luminogen (AIEgen) via an optional linker.

In certain embodiments, the at least one AIEgen is a photosensitizer.

In certain embodiments, the at least one AIEgen has the Formula 1:

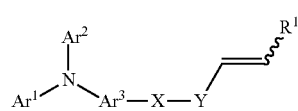

or a pharmaceutically acceptable salt thereof, wherein each of $Ar^1$, $Ar^2$, and $Ar^3$ is independently an optionally substituted aryl or an optionally substituted heteroaryl;

X is an optionally substituted aryl, an optionally substituted heteroaryl, or a covalent bond;
Y is an optionally substituted heteroaryl or a covalent bond; and
$R^1$ is a moeity having the formula:

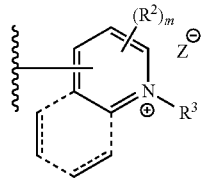

wherein m is a whole number selected from 1-4;
$R^2$ for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl;
$R^3$ is alkyl, cycloalkyl, alkenyl, alkynyl, optionally substituted aryl, optionally substituted aralkyl, heterocycloalkyl, optionally substituted heteroaryl, or —(CH$_2$)$_n$N(R$^4$)$_3$$^+$Z$^-$, wherein n is a whole number selected from a whole number selected from 2-8; and $R^4$ for each occurrence is independently alkyl;
R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and
Z is a pharmaceutically acceptable anion, wherein the bacteriophage is covalently bonded via an optional linker to Ar$^1$, Ar$^2$, Ar$^3$, X, Y, or $R^1$.

In certain embodiments, each of Ar$^1$, Ar$^2$, and Ar$^3$ is independently an optionally substituted aryl; X is an optionally substituted aryl or a covalent bond; and Y is a heteroaryl or a covalent bond.

In certain embodiments, wherein the at least one AIEgen has the Formula 2:

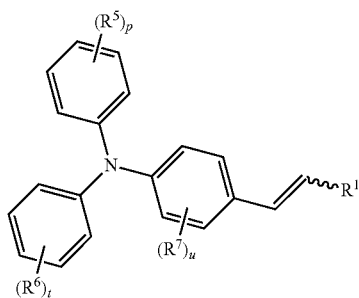

2 or a pharmaceutically acceptable salt thereof, wherein each of p and t is independently a whole number selected from 1-5;

u is a whole number selected from 1-4;
$R^1$ is a moeity having the formula:

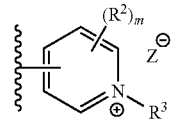

wherein m is a whole number selected from 1-4;
$R^2$ for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl; and
$R^3$ is alkyl, cycloalkyl, alkenyl, alkynyl, optionally substituted aryl, optionally substituted aralkyl, heterocycloalkyl, optionally substituted heteroaryl, or —(CH$_2$)$_n$N(R$^4$)$_3$$^+$Z$^-$, wherein n is a whole number selected from 2-8; and $R^4$ for each occurrence is independently alkyl;
each of $R^5$, $R^6$, and $R^7$ for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;
R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl;
$R^8$ represents a moiety having the structure:

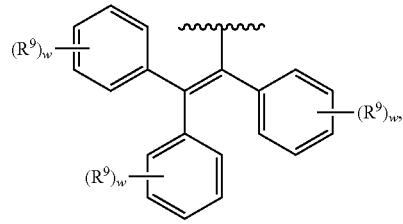

wherein w for each instance is independently a whole number selected from 1-5; and
$R^9$ for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl; and
Z for each occurrence is independently a pharmaceutically acceptable anion, wherein the bacteriophage is covalently bonded via an optional linker at R, $R^2$, $R^3$, $R^5$, $R^6$, $R^7$, or $R^9$.

In certain embodiments, each of m, p, t, u, and w is independently 1 or 2.

In certain embodiments, the at least one AIEgen has the Formula 3:

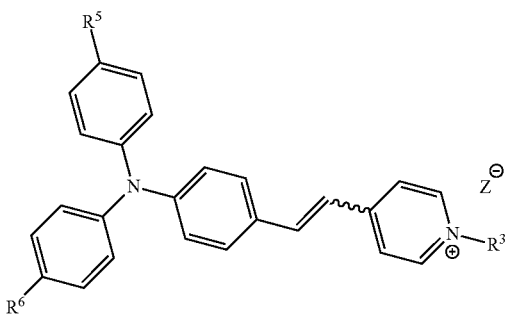

3 or a pharmaceutically acceptable salt thereof, wherein
R³ is alkyl, cycloalkyl, alkenyl, alkynyl, optionally substituted aryl, optionally substituted aralkyl, heterocycloalkyl, optionally substituted heteroaryl, or —(CH₂)$_n$N(R⁴)₃⁺Z⁻, wherein n is a whole number selected from 2-8; and R⁴ for each occurrence is independently alkyl;
each of R⁵ and R⁶ is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, aryl, aralkyl, heterocycloalkyl, heteroaryl, and R⁸;
R⁸ represents a moiety having the structure:

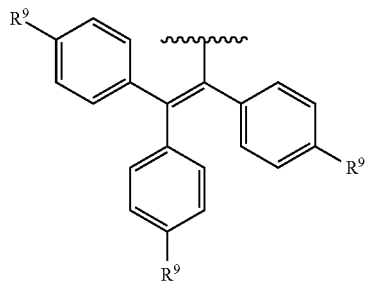

wherein R⁹ for each instance is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, optionally substituted aryl, optionally substituted aralkyl, heterocycloalkyl, and optionally substituted heteroaryl;
R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and Z for each occurrence is independently a pharmaceutically acceptable anion, wherein the bacteriophage is covalently bonded via an optional linker at R³, R⁵, or R⁶, or R⁹.

In certain embodiments, the optional linker is represented by the formula: *—(CR⁴₂)$_n$J-**, wherein n is a whole number selected from 0-12; J is —(C=O)—, —(C=S)—, —NH(C=O)—, or —NH(C=S)—; and R⁴ for each occurrence is independently selected from the group consisting of hydrogen and alkyl; or two instances of R⁴ taken together with the carbon or carbons to which they are covalently bonded form a 3-7 membered cycloalkyl, wherein * represents the site of covalent attachment to the AIEgen having Formula 1; and ** represents the site of covalent attachment of the bacteriophage.

In certain embodiments, the optional linker is represented by the formula: *—(CH₂)n(C=O)—** wherein n is a whole number selected from 2-8, wherein * represents the site of covalent attachment to the AIEgen having Formula 1; and ** represents the site of covalent attachment of the bacteriophage.

In certain embodiments, the optional linker is represented by the formula: *—(CR⁴₂)$_n$(C=O)—**, wherein n is a whole number selected from 0-12; and R⁴ for each occurrence is independently selected from the group consisting of hydrogen and alkyl; or two instances of R⁴ taken together with the carbon or carbons to which they are covalently bonded form a 3-7 membered cycloalkyl, wherein * represents the site of covalent attachment to the AIEgen having Formula 1; and ** represents the site of covalent attachment of the bacteriophage.

In certain embodiments, the at least one AIEgen has the Formula 4:

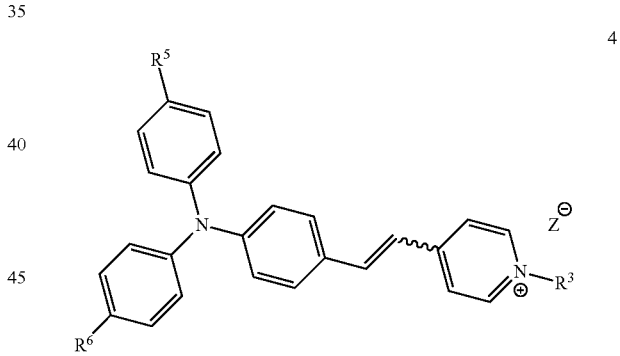

4 or a pharmaceutically acceptable salt thereof, wherein
R³ is the linker represented by the formula: *—(CR⁴₂)$_n$(C=O)—**, wherein n is a whole number selected from 1-10; and R⁴ for each occurrence is independently selected from the group consisting of hydrogen and alkyl; or two instances of R⁴ taken together with the carbon or carbons to which they are covalently bonded form a 3-7 membered cycloalkyl, wherein * represents the site of covalent attachment to the AIEgen having Formula 4; and ** represents the site of covalent attachment of the bacteriophage;
each of R⁵ and R⁶ is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, aryl, aralkyl, heterocycloalkyl, heteroaryl, and R⁸;

$R^8$ represents a moiety having the structure:

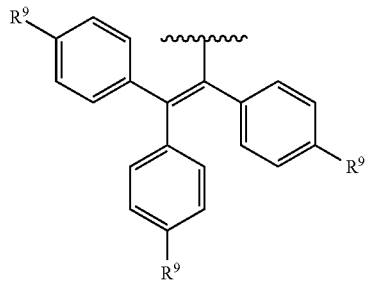

wherein $R^9$ for each instance is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl;

R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and Z for each occurrence is independently a pharmaceutically acceptable anion.

In certain embodiments, the bioconjugate comprises between 1,000-20,000 of the at least one AIEgen.

In certain embodiments, the at least one AIEgen and linker is a moiety selected from the group consisting of:

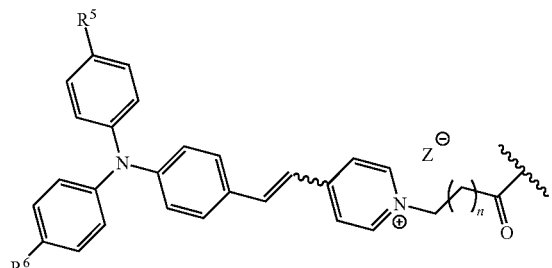

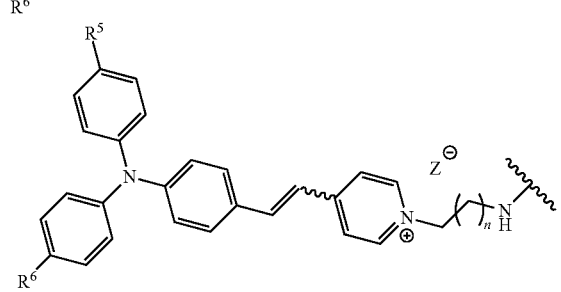

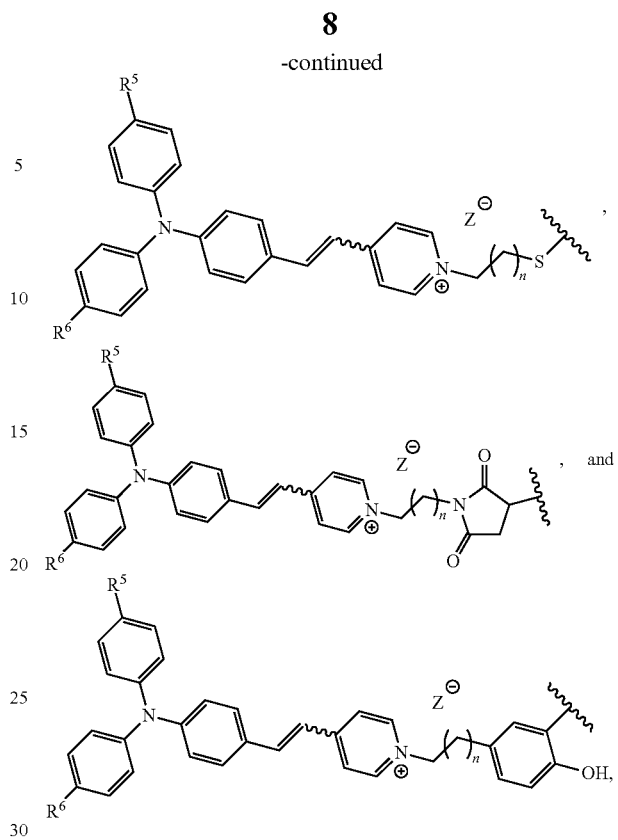

or a pharmaceutically acceptable salt thereof, wherein
n is a whole number selected from 0-4;
each of $R^5$ and $R^6$ is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;
$R^8$ represents a moiety having the structure:

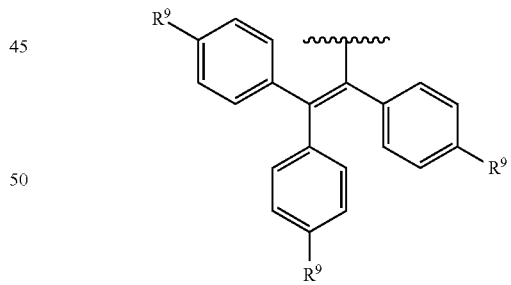

wherein $R^9$ for each instance is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl;

R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and Z for each occurrence is independently a pharmaceutically acceptable anion, wherein ⸱ represents the site of covalent attachment to the bacteriophage.

In certain embodiments, the at least one AIEgen and linker is represented by:

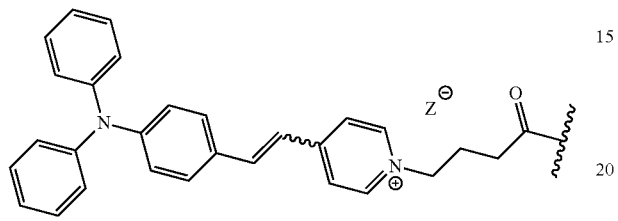

or a pharmaceutically acceptable salt thereof, wherein Z is a pharmaceutically acceptable anion; and ⸱ represents the site of covalent attachment to the bacteriophage.

In certain embodiments, the bacteriophage is a filamentous or icosahedral bacteriophage.

In certain embodiments, the bacteriophage is enterobacteria phage P7 (PAP).

In a second aspect provided herein is a pharmaceutical composition comprising a bioconjugate described herein and at least on pharmaceutically acceptable excipient.

In a third aspect provided herein is a compound of Formula 5:

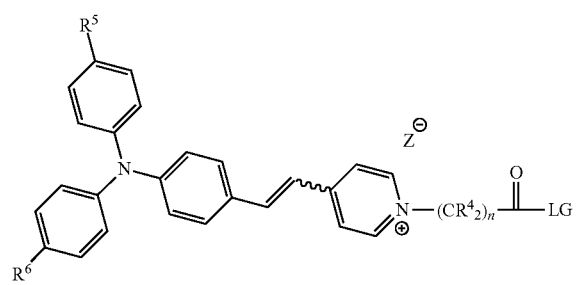

or a pharmaceutically acceptable salt thereof, wherein n is a whole number selected from 1-10;

LG is a leaving group;

each of $R^5$ and $R^6$ is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;

$R^8$ represents a moiety having the structure:

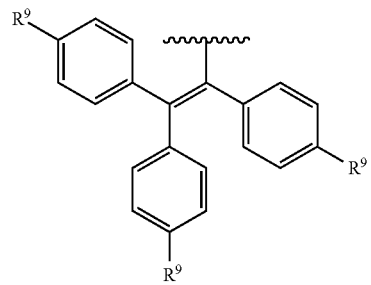

wherein $R^9$ for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl; and Z for each occurrence is independently a pharmaceutically acceptable anion.

In a fourth aspect, provided herein is a method of preparing the bioconjugate, the method comprising: contacting a compound of Formula 5:

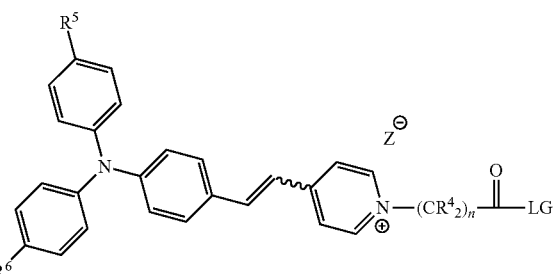

or a pharmaceutically acceptable salt thereof, wherein n is a whole number selected from 1-10;

LG is a leaving group;

each of $R^5$ and $R^6$ is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;

$R^8$ represents a moiety having the structure:

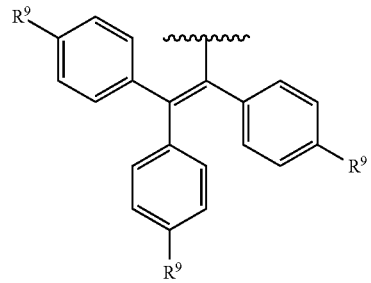

wherein $R^9$ for each instance is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl;

R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and Z for each occurrence is independently a pharmaceutically acceptable anion; with a bacteriophage thereby forming the bioconjugate.

In a fifth aspect, provided herein is a method of treating a bacterial infection in a subject in need thereof, the method comprising administering a therapeutically effective amount of a bioconjugate described herein to the subject and irradiating the site of the bacterial infection with electromagnetic radiation in the presence of oxygen.

In a sixth aspect, provided herein is a method of imaging a bacterial cell, the method comprising contacting a bioconjugate described herein with the bacterial cell; irradiating the bacterial cell with electromagnetic radiation; and detecting luminesence from the bioconjugate.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present disclosure. It will be appreciated that these drawings depict exemplary embodiments of the invention and as such are not intended to limit its scope. The invention will be described and explained with additional specificity and detail through the use of the accompanying drawings.

DETAILED DESCRIPTION OF THE INVENTION

Definitions

Figure 1:
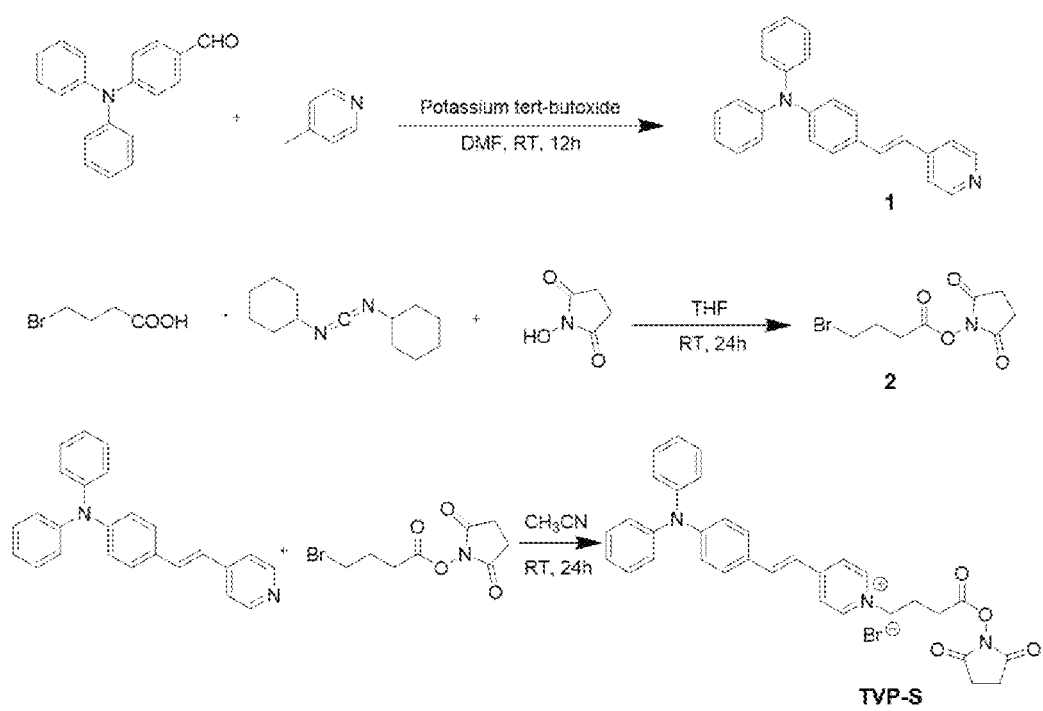
FIG. 1 depicts an exemplary synthesis of TVP-S.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "halo", "halide", or "halogen" refers to fluoro, chloro, bromo, and iodo.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., C1-40 alkyl group), for example, 1-30 carbon atoms (i.e., C1-30 alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

The term "aralkyl" is art-recognized and refers to an alkyl group substituted with an aryl group (e.g., an aromatic or heteroaromatic group).

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be optionally substituted as described herein. The aryl ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be optionally substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be optionally substituted as described herein. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl, aryl, heteroaryl, and the like, wherein one or more hydrogen may be replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like; or chemical moiety represented by the structure:

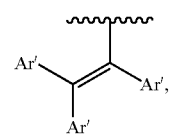

wherein Ar' for each instance is independently an optionally substituted phenyl.

The representation "⸦" as used herein in connection to chemical a group or moiety is intended to represent the covalent bond that the aforementioned chemical group or moiety is covalently bonded to another chemical group, moiety, or bacteriophage.

The phrase "aggregation-induced emission" or "AIE" as used herein refers to the enhancement of light-emission by a fluorescent compound upon aggregation in the amorphous or crystalline (solid) states or bound to the surface or inner cavity of larger macromolecules or particles via covalent or non-covalent interaction (electrostatic attraction, hydrophobic-hydrophobic interaction, hydrogen bonding, etc, with the inhibition of their molecular motions) of the fluorescent compound, whereas the fluorescent compound exhibits weak or substantially no emission when the AIE molecules are separated with each other.

The term "$\lambda_{ex}$" as used herein refers to the excitation wavelength.

The term "$\lambda_{em}$" as used herein refers to the emission wavelength.

The terms "bacteriophage" and "phage" are used interchangeably herein to indicate a bacterial virus, which forms a package comprising a protein coat containing nucleic acid required for its replication. The nucleic acid may be DNA or RNA, either double or single stranded, linear or circular.

As used herein by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "therapeutically effective" means the amount of the composition used is of sufficient quantity to ameliorate one or more causes or symptoms of a disease or disorder. Such amelioration only requires a reduction or alteration, not necessarily elimination.

As used herein, the term pharmaceutically acceptable salt refers to any salt of the compound of this invention which retains its biological properties and which is not toxic or otherwise undesirable for pharmaceutical use. Such salts may be derived from a variety of organic and inorganic counterions well known in the art and include them. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion (e.g., an alkali metal ion, an alkaline earth ion or an aluminum ion), or alkali metal or alkaline earth metal hydroxides (e.g., sodium, potassium, calcium, magnesium, aluminum, lithium, zinc, and barium hydroxide), ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. In addition, examples of salts include sodium, potassium, calcium, magnesium, ammonium, tetraalkylammonium and the like, and when the compound contains a basic functionality, salts of non-toxic organic or inorganic acids, such as halides (e.g., chloride, bromide, and iodide), sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate; fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

When trade names are used herein, applicants intend to independently include the trade name product formulation, the generic drug, and the active pharmaceutical ingredient(s) of the trade name product.

The present disclosure provides an AIE-bacteriophage bioconjugate comprising a bacteriophage covalently bonded to at least one AIEgen via an optional linker The at least one AIEgen can be covalently bonded to a surface of the protein coat of the bacteriophage via attachment to suitable functional groups in the protein coat, such as one or more functional groups selected from the group consisting of lysine side chains, cysteine side chains, and N-terminal amines.

There may be between 1-100,000 AIEgen covalently bonded to the bacteriophage via an optional linker. In certain embodiments, the bioconjugate comprises 1-50,000, 1-40,000, 1-30,000, 1-20,000, 1,000-20,000, 1,000-10,000, 1-10,000, 5,000-10,000, or 7,000-10,000 AIEgen covalently bonded to the bacteriophage via an optional linker.

In certain embodiments, the at least one AIEgen is or comprises a photosensitizer.

In certain embodiments, the at least one AIEgen has the Formula 1:

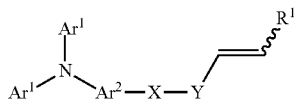

or a pharmaceutically acceptable salt thereof, wherein
each of $Ar^1$, $Ar^2$, and $Ar^3$ is independently an optionally substituted aryl or an optionally substituted heteroaryl;
X is an optionally substituted aryl, an optionally substituted heteroaryl, or a covalent bond;
Y is an optionally substituted heteroaryl or a covalent bond; and
$R^1$ is a moeity having the formula:

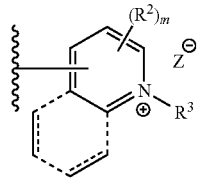

wherein m is a whole number selected from 1-4;
$R^2$ for each instance is independently selected from the group consisting of hydrogen, halide, cyano, nitro, —OR, —SR, —$N(R)_2$, —(C=O)R, —(C=O)OR, —(C=O)$N(R)_2$, —N(R)(C=O)R, —O(C=O)R, —N(R)(C=O)OR, —O(C=O)$N(R)_2$, —$SO_2R$, —$SO_2N(R)_2$, alkyl, cycloalkyl, alkenyl, alkynyl, optionally substituted aryl, optionally substituted aralkyl, heterocycloalkyl, and optionally substituted heteroaryl;
$R^3$ is alkyl, cycloalkyl, alkenyl, alkynyl, optionally substituted aryl, optionally substituted aralkyl, heterocycloalkyl, optionally substituted heteroaryl, or —$(CH_2)_nN(R^4)_3{}^+Z^-$, wherein n is a whole number selected from 2-8; and $R^4$ for each occurrence is independently alkyl;
R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and Z is an anion, wherein the bacteriophage is covalently bonded via an optional linker to $Ar^1$, $Ar^2$, $Ar^3$, X, Y, or $R^1$.

In certain embodiments, each of $Ar^1$, $Ar^2$, and $Ar^3$ is independently an optionally substituted aryl; X is an optionally substituted aryl or a covalent bond; and Y is a heteroaryl or a covalent bond. In certain embodiments, each of $Ar^1$, $Ar^2$, and $Ar^3$ is independently an optionally substituted phenyl; and X is an optionally substituted phenyl. In certain embodiments, Y is optionally substituted thiophene, optionally substituted furan, or a covalent bond.

In certain embodiments, $R^1$ is a moeity having the formula selected from the group consisting of:

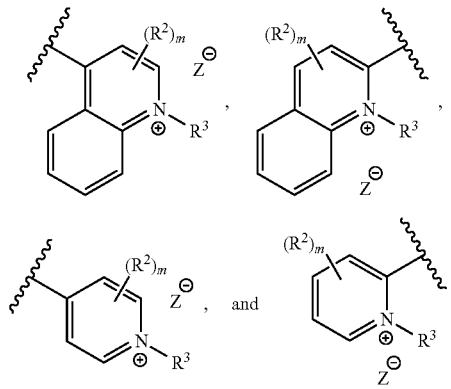

wherein m, $R^2$, $R^3$, and Z are as defined in any one or more embodiments described herein, and wherein if $R^1$ is a quinonlinium, each $R^2$ can independently be covalently bonded to any carbon ring atom of the quinonlinium permitted by valency.

In certain embodiments, the at least one AIEgen is selected from the group consisting of:

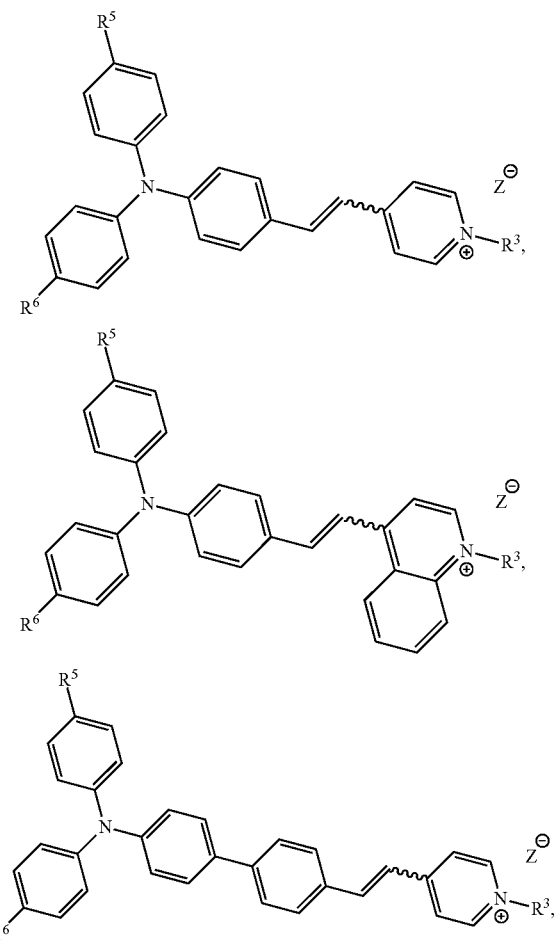

-continued

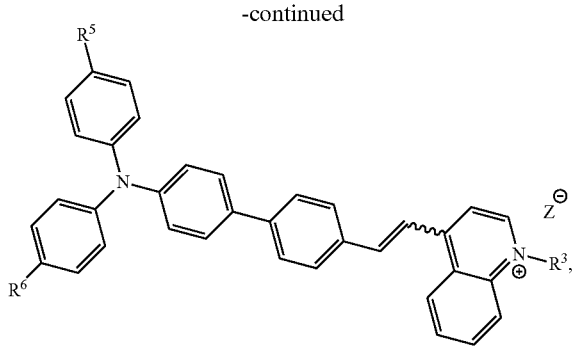

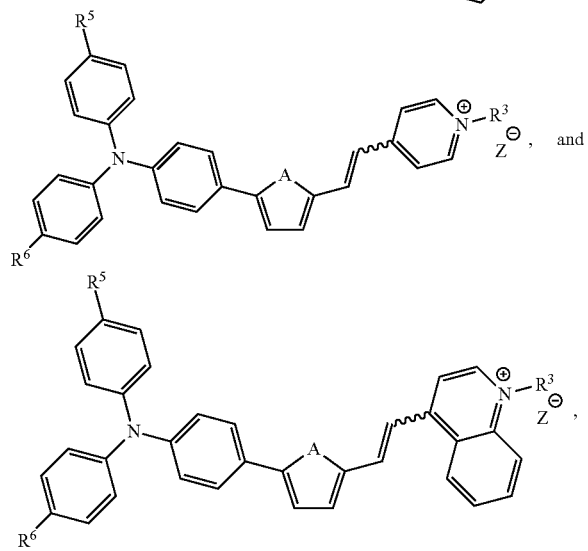

or a pharmaceutically acceptable salt thereof, wherein
A is O or S;
R³ is alkyl, cycloalkyl, alkenyl, alkynyl, optionally substituted aryl, optionally substituted aralkyl, heterocycloalkyl, optionally substituted heteroaryl, or —(CH$_2$)$_n$N(R$^4$)$_3$$^+$Z$^-$, wherein n is a whole number selected from 2-8; and R⁴ for each occurrence is independently alkyl;
each of R⁵ and R⁶ is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, aryl, aralkyl, heterocycloalkyl, heteroaryl, and R⁸;
R⁸ represents a moiety having the structure:

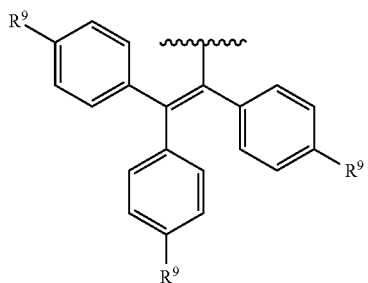

wherein R⁹ for each instance is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl; and
Z for each occurrence is independently a pharmaceutically acceptable anion, wherein the bacteriophage is covalently bonded via an optional linker at R³, R⁵, or R⁶, or R⁹.

In certain embodiments, the at least one AIEgen has the Formula 2:

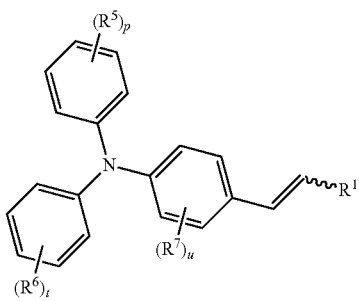

or a pharmaceutically acceptable salt thereof, wherein
each of p and t is independently a whole number selected from 1-5;
u is a whole number selected from 1-4;
R¹ is a moeity having the formula:

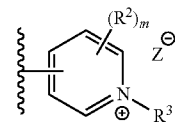

wherein m is a whole number selected from 1-4;
R² for each instance is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl; and
R³ is alkyl, cycloalkyl, alkenyl, alkynyl, optionally substituted aryl, optionally substituted aralkyl, heterocycloalkyl, optionally substituted heteroaryl, or —(CH$_2$)$_n$N(R$^4$)$_3$$^+$Z$^-$, wherein n is a whole number selected from 2-8; and R⁴ for each occurrence is independently alkyl;
each of R⁵, R⁶, and R⁷ for each instance is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, aryl, aralkyl, heterocycloalkyl, heteroaryl, and R⁸;
R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl;

R⁸ represents a moiety having the structure:

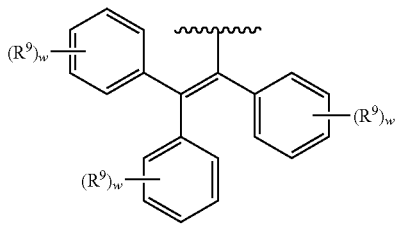

wherein w for each instance is independently a whole number selected from 1-5; and R⁹ for each instance is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, optionally substituted aryl, optionally substituted aralkyl, heterocycloalkyl, and optionally substituted heteroaryl; and Z for each occurrence is independently a pharmaceutically acceptable anion, wherein the bacteriophage is covalently bonded via an optional linker at R, R², R³, R⁵, R⁶, R⁷, or R⁹.

In certain embodiments, t and p are each 1 and R⁷ is hydrogen. In certain embodiments, w is 1. In certain embodiments, m is 1.

In certain embodiments, R¹ is a moiety selected from the group consisting of:

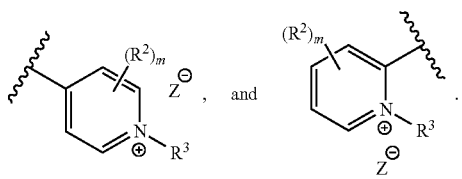

In certain embodiments, R² is hydrogen. In certain embodiments, R⁹ is hydrogen.

In certain embodiments, R³ is alkyl or —(CH₂)ₙN(R⁴)₃⁺Z⁻, wherein n is a whole number selected from 2-8; and R⁴ for each occurrence is independently alkyl.

In certain embodiments, each of R⁵ and R⁶ for each instance is independently selected from the group consisting of hydrogen, halide, cyano, nitro, —OR, —N(R)₂, —N(R)(C=O)R, —O(C=O)R, —N(R)(C=O)OR, —O(C=O)N(R)₂, alkyl, cycloalkyl, alkenyl, alkynyl, aryl, aralkyl, heterocycloalkyl, heteroaryl, and R⁸. In certain embodiments, each of R⁵ and R⁶ for each instance is independently selected from the group consisting of hydrogen, halide, cyano, nitro, alkyl, cycloalkyl, aryl, heterocycloalkyl, heteroaryl, and R⁸.

In certain embodiments, R⁷ for each instance is independently selected from the group consisting of hydrogen, halide, cyano, nitro, —OR, —N(R)₂, —N(R)(C=O)R, —O(C=O)R, —N(R)(C=O)OR, —O(C=O)N(R)₂, alkyl, cycloalkyl, alkenyl, alkynyl, aryl, aralkyl, heterocycloalkyl, heteroaryl, and R⁸. In certain embodiments, R⁷ for each instance is independently selected from the group consisting of hydrogen, halide, cyano, nitro, alkyl, cycloalkyl, aryl, heterocycloalkyl, heteroaryl, and R⁸.

Z may be selected from the group consisting of halides (e.g., chloride, bromide, and iodide), sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate; fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, and muconate.

In certain embodiments, the at least one AIEgen has the Formula 3:

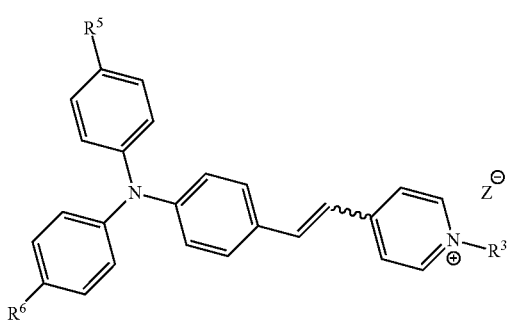

or a pharmaceutically acceptable salt thereof, wherein

R³ is alkyl, cycloalkyl, alkenyl, alkynyl, optionally substituted aryl, optionally substituted aralkyl, heterocycloalkyl, optionally substituted heteroaryl, or —(CH₂)ₙN(R⁴)₃⁺Z⁻, wherein n is a whole number selected from 2-8; and R⁴ for each occurrence is independently alkyl;

each of R⁵ and R⁶ is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, aryl, aralkyl, heterocycloalkyl, heteroaryl, and R⁸;

R⁸ represents a moiety having the structure:

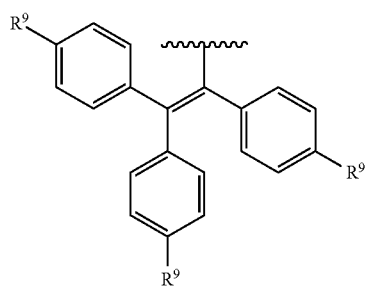

wherein R⁹ for each instance is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, optionally substituted aryl, optionally substituted aralkyl, heterocycloalkyl, and optionally substituted heteroaryl; and Z for each occurrence is independently a pharmaceutically acceptable anion, wherein the bacteriophage is covalently bonded via an optional linker at R³, R⁵, or R⁶, or R⁹.

The optional linker may be any linker known in the art. The optional linker may be a labile linker or a non-labile linker. Exemplary labile linkers include those which are labile under physiological conditions, such as acid labile linkers, base labile linkers, enzyme labile linkers. The linker may have a liner, cyclic, branched structure. The optional linker may comprise one or more functional groups in the linker selected from the group consisting of ethers, sulfides, disulfides, amides, amines, ketones, carbonates, carbamates, ureas, alkoxyamines, imines, alkoxy, imines and the like.

In certain embodiments, the linker is represented by the formula: *—(CR⁴₂)ₙJ-**, wherein n is a whole number selected from 0-12; J is —(C=O)—, —(C=S)—, —NH(C=O)—, —NH(C=S)—, —N— succinimidyl, —S—, —NH—, or phenol; and R⁴ for each occurrence is independently selected from the group consisting of hydrogen and alkyl; or two instances of R⁴ taken together with the carbon or carbons to which they are covalently bonded form a 3-7 membered cycloalkyl, wherein * represents the site of covalent attachment to the AIEgen having Formula 1; and ** represents the site of covalent attachment of the bacteriophage. In certain embodiments, n is a whole number selected from 1-6, 1-5, 2-5, or 2-4. In certain embodiments, each R is hydrogen.

In certain embodiments, the at least one AIEgen has the Formula 4:

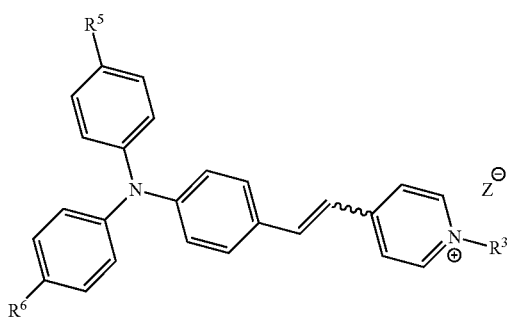

4 or a pharmaceutically acceptable salt thereof, wherein
R³ is the linker represented by the formula: *—(CR⁴₂)ₙ(C=O)—**, wherein n is a whole number selected from 1-10; and R⁴ for each occurrence is independently selected from the group consisting of hydrogen and alkyl; or two instances of R⁴ taken together with the carbon or carbons to which they are covalently bonded form a 3-7 membered cycloalkyl, wherein * represents the site of covalent attachment to the AIEgen having Formula 4; and ** represents the site of covalent attachment of the bacteriophage;

each of R⁵ and R⁶ is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, aryl, aralkyl, heterocycloalkyl, heteroaryl, and R⁸;

R⁸ represents a moiety having the structure:

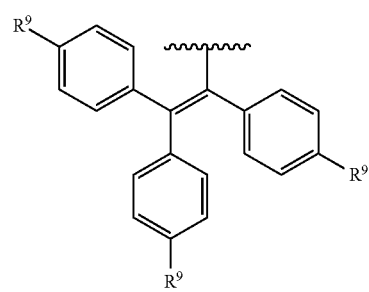

wherein R⁹ for each instance is independently selected from the group consisting of hydrogen, halide, cyano, nitro, —OR, —SR, —N(R)₂, —(C=O)R, —(C=O)OR, —(C=O)N(R)₂, —N(R)(C=O)R, —O(C=O)R, —N(R)(C=O)OR, —O(C=O)N(R)₂, —SO₂R, —SO₂N(R)₂, alkyl, cycloalkyl, alkenyl, alkynyl, optionally substituted aryl, optionally substituted aralkyl, heterocycloalkyl, and optionally substituted heteroaryl; and Z for each occurrence is independently a pharmaceutically acceptable anion.

In certain embodiments, the at least one AIEgen is selected from the group consisting of:

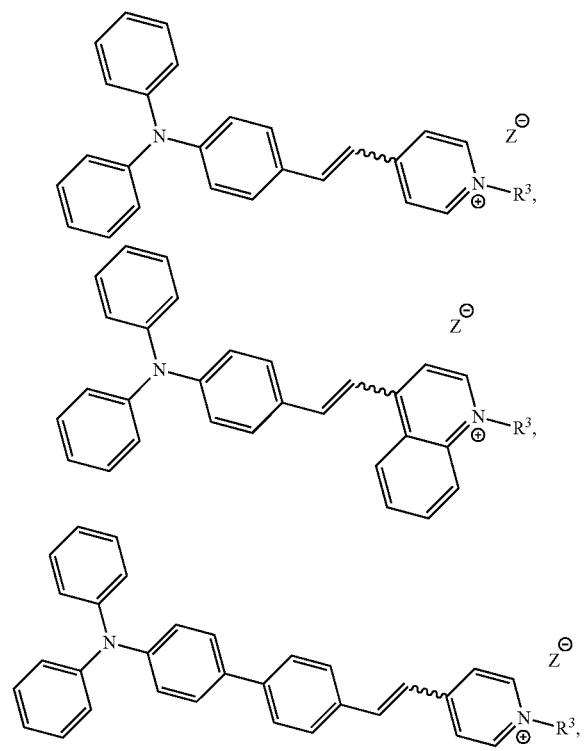

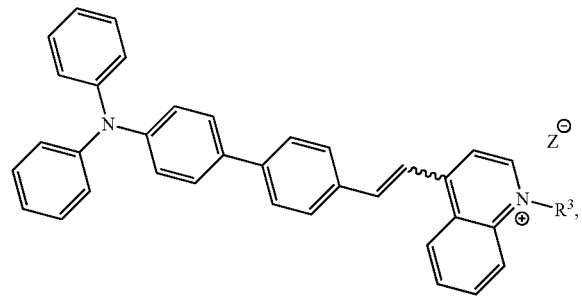

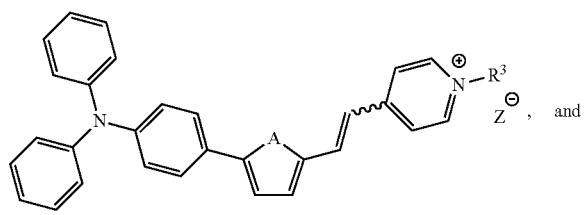

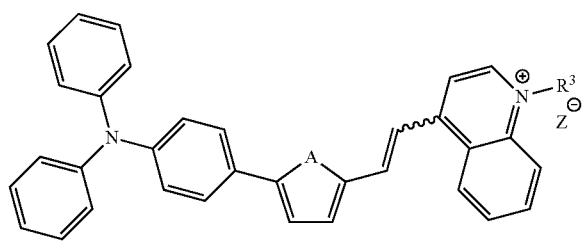

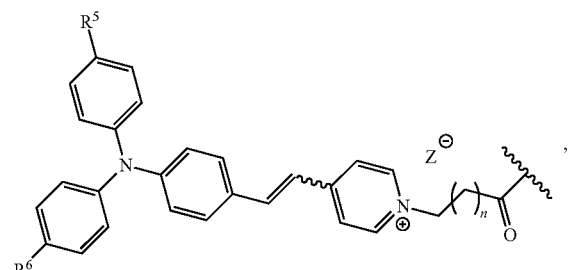

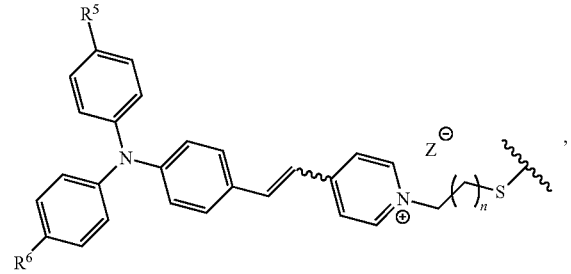

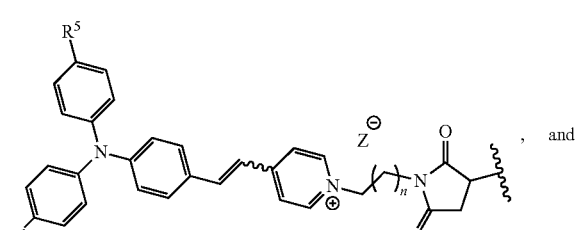

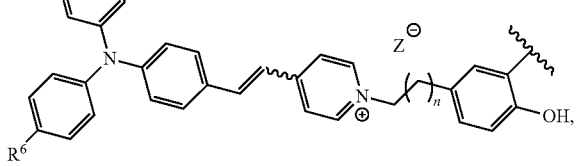

or a pharmaceutically acceptable salt thereof, wherein A is O or S; $R^3$ is: *—$(CH_2)_n$(C=O)—**, wherein n is a whole number selected from 1-6, 1-5, 1-4, or 2-4; * represents the site of covalent attachment to the AIEgen; and ** represents the site of covalent attachment of the bacteriophage; and Z is a pharmaceutically acceptable anion.

Depending on the reactive functionality present in the at least one AIEgen, the at least one AIEgen may be conjugated to the bacteriophage using any number of functional groups. For example, in instances in which the at least one AIEgen comprises a reactive amine, the at least one AIEgen may be conjugated to a C-terminal carboxylic acid or an amino acid side chain comprising a carboxylic acid (e.g., glutamic acid, aspartic acid, etc); in instances in which the at least one AIEgen comprises a reactive carboxyl group, the at least one AIEgen may be conjugated to a N-terminal amine or an amino acid side chain comprising an amine (e.g., lysine); in instances in which the at least one AIEgen comprises a reactive thiol, the at least one AIEgen may be conjugated to an amino acid side chain comprising a mercaptan (e.g., cysteine); in instances in which the at least one AIEgen comprises a reactive double bond (e.g., maleimide moiety), the at least one AIEgen may be conjugated to an amino acid side chain comprising a mercaptan (e.g., cysteine); and in instances in which the at least one AIEgen comprises a reactive phenolic group, the at least one AIEgen may be conjugated to an amino acid side chain comprising a phenol (e.g., tyrosine). Thus, in certain embodiments, the at least one AIEgen is selected from the group consisting:

or a pharmaceutically acceptable salt thereof, wherein n, Z, $R^5$, and $R^6$, are each independently as defined any one or more embodiments described herein; or n is a whole number selected from 0-12; 1-12; 0-10; 1-10; 0-8; 1-8; 0-6; 1-6; 0-5; 1-5; 0-4; 1-4; 0-3, 1-3, 0-2, 1-2, or 0-1; and ⁂ represents the site of covalent attachment to the bacteriophage.

In certain embodiments, the at least one AIEgen is:

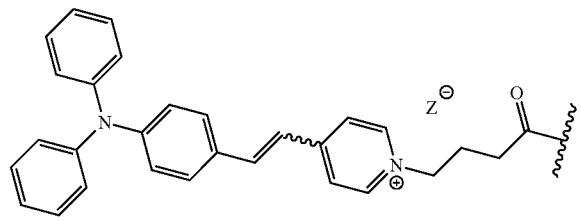 [SMILES: *C(=O)CCC[n+]1ccc(C=Cc2ccc(N(c3ccccc3)c3ccccc3)cc2)cc1]

or a pharmaceutically acceptable salt thereof, wherein Z is a pharmaceutically acceptable anion; and ⸠ represents the site of covalent attachment to the bacteriophage.

In certain embodiments, the bacteriophage is a member of a viral family selected from the group consisting of Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttavirus, Inoviridae, Leviviridae, Microviridae, Plasmaviridae, and Tectiviridae. In certain embodiments, the bacteriophage is lytic to a bacterial cell and selected from the group consisting of *Campylobacter, Cronobacter, Escherichia, Salmonella, Lactococcus, Vibrio, Erwinia, Xanthomonas, Shigella, Staphylococcus, Streptococcus, Clostridium, Pseudomonas, Mycobacterium, Neisseria*, and Bacilli.

In certain embodiments, the bacteriophage is selected from the group consisting of Phage PAP1, PAP2, PAP3, PAP7, Phage SWHAb1, SWHAb2, Bϕ-C62, φAbp1, Phage JSO1, Phage T2, T4, Phage ΦCrAss001, Phage SMP, Phage Φm46.1, and Phage P2.

The selection of the bacteriophage is based in part on the bacterial specificity of the bacteriophage. For example, lambda phage, Phage T2, and T4 may be used to target and infect *Escherichia coli* (a gram-negative bacteria); phi-104 may be used to target and infect *Bacillus subtilis*; Phage PAP1, PAP2, PAP3, PAP7 may be used to target and infect *Pseudomonas aeruginosa*; Phage SWHAb1, SWHAb2, Bϕ-C62, φAbp1 may be used to target and infect *Acinetobacter baumannii*; Phage JSO1 may be used to target and infect *Staphylococcus aureus*; Phage ΦCrAss001 may be used to target and infect *Bacteroides* intestinalis; Phage SMP may be used to target and infect *Streptococcus suis*; Phage Φm46.1 may be used to target and infect *Pyogenic streptococcus*; Phage P2 may be used to target and infect *Fusobacterium nucleatum*. In certain embodiments, the bacteriophage is PAP.

The present disclosure also provides a pharmaceutical composition comprising a bioconjugate described herein and at least one pharmaceutically acceptable excipient.

The bioconjugates described herein and their pharmaceutically acceptable salts can be administered to a subject either alone or in combination with pharmaceutically acceptable, excipients, carriers, and/or diluents in a pharmaceutical composition according to standard pharmaceutical practice. The bioconjugates can be administered orally or parenterally. Parenteral administration includes intravenous, intramuscular, intraperitoneal, subcutaneous and topical, the preferred method being intravenous and topical administrations.

Accordingly, the present disclosure provides pharmaceutically acceptable compositions, which comprise a therapeutically effective amount of one or more of the bioconjugates described herein, formulated together with one or more pharmaceutically, excipients, acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

As set out herein, certain embodiments of the bioconjugates described herein may contain a basic functional group, such as amino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present disclosure. These salts can be prepared in situ in the administration vehicle or the dosage form manufacturing process, or by separately reacting a purified bioconjugates of the invention in its free base form with a suitable organic or inorganic acid, and isolating the salt thus formed during subsequent purification. Representative salts include the hydrobromide, hydrochloride, sulfate, bisulfate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the bioconjugates of the present disclosure include the conventional non-toxic salts or quaternary ammonium salts of the compounds, e.g., from non-toxic organic or inorganic acids. For example, such conventional non-toxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the bioconjugates described herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present disclosure. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing these formulations include the step of bringing into association a bioconjugates described herein with the carrier or excipient and, optionally, one or more accessory ingredients. In general, the formulations are prepared by uniformly and intimately bringing into association a bioconjugates of the present disclosure with liquid carriers (liquid formulation), followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more bioconjugates described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the bioconjugates of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

The at least one AIEgen may be conjugated to the bacteriophage using any method known to those skilled in the art. A person of ordinary skill in the art can readily selected the appropriate synthetic methodology to effect the conjugation of the at least one AIEgen to the bacteriophage depending on the reactive functionality present in the at least one AIEgen.

In instances in which the at least one AIEgen is represented by the formula:

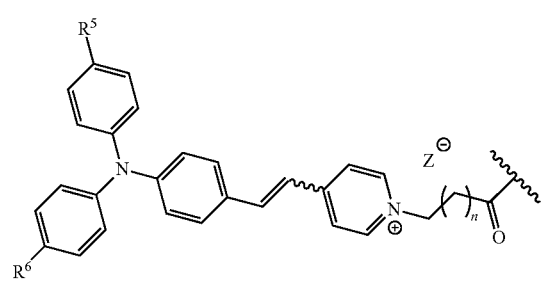 or

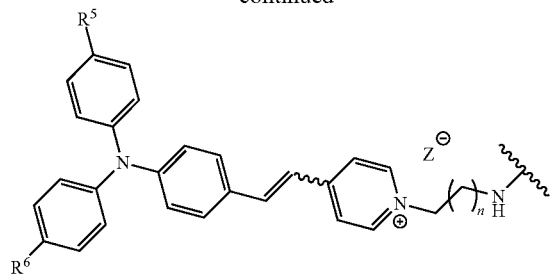

or a pharmaceutically acceptable salt thereof, wherein represents the site of covalent attachment to the bacteriophage; the bioconjugate can be prepared by the reaction of a compound selected from:

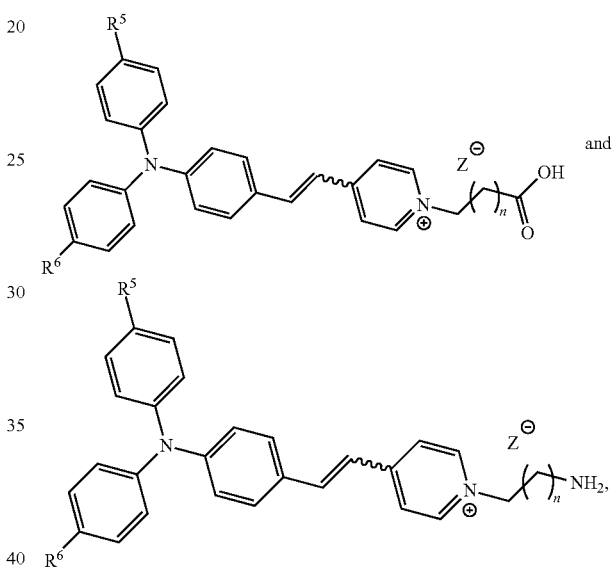

or a pharmaceutically acceptable salt thereof, wherein n, Z, $R^5$, and $R^6$, are each independently as defined any one or more embodiments described herein, the bacteriophage, and peptide coupling reagents, such as those described in greater detail below, which results in the conjugation of the compound to C-terminal carboxylic acid or an amino acid comprising a carboxylic side chain; or conjugation to the N-terminal amine of an amino acid comprising an amine side chain.

In instances in which the at least one AIEgen is represented by the formula:

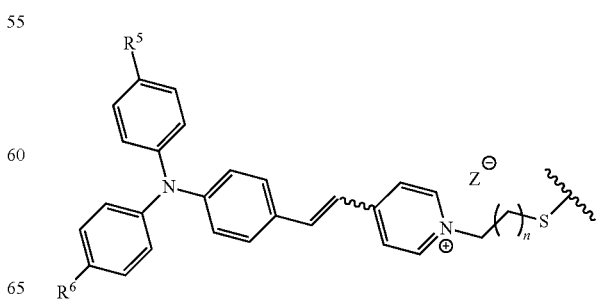

or a pharmaceutically acceptable salt thereof, wherein ⸹ represents the site of covalent attachment to the bacteriophage; the bioconjugate can be prepared by the reaction of a compound represented by the formula:

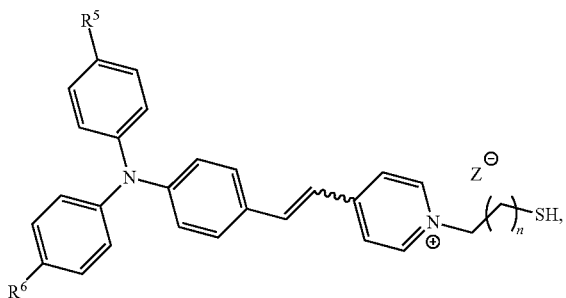

or a pharmaceutically acceptable salt thereof, wherein n, Z, $R^5$, and $R^6$, are each independently as defined any one or more embodiments described herein, and the bacteriophage under an oxidative coupling conditions, which results in the conjugation of the compound to an amino acid comprising a mercaptan side chain via oxidative coupling.

In instances in which the at least one AIEgen is represented by the formula:

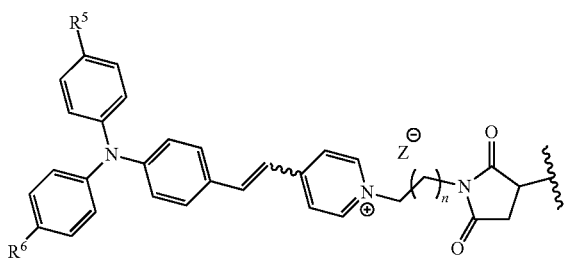

or a pharmaceutically acceptable salt thereof, wherein represents the site of covalent attachment to the bacteriophage; the bioconjugate can be prepared by the reaction of a compound represented by the formula:

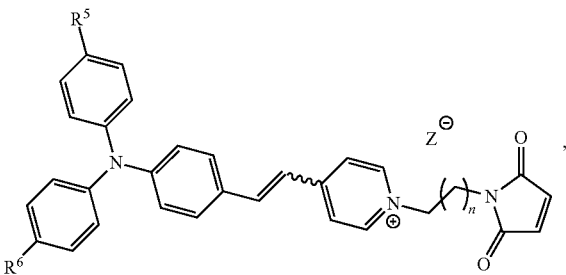

or a pharmaceutically acceptable salt thereof, wherein n, Z, $R^5$, and $R^6$, are each independently as defined any one or more embodiments described herein, and the bacteriophage under 1,4 addition reaction conditions (e.g., in the presence of a base or basic buffer solution), which results in the conjugation of the compound to an amino acid comprising a mercaptan side chain via a 1,4 addition reaction.

In instances in which the at least one AIEgen is represented by the formula:

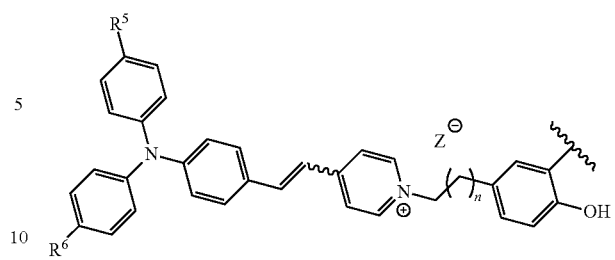

or a pharmaceutically acceptable salt thereof, the bioconjugate can be prepared by the reaction of a compound represented by the formula:

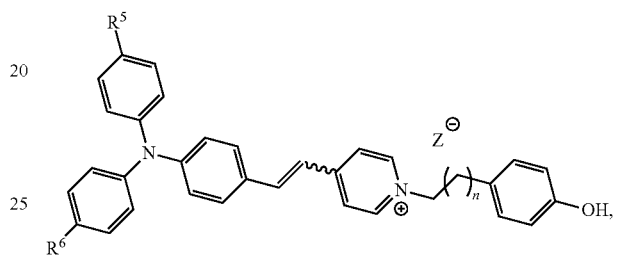

or a pharmaceutically acceptable salt thereof, wherein n, Z, $R^5$, and $R^6$, are each independently as defined any one or more embodiments described herein, and the bacteriophage by an enzyme mediated oxidative coupling (e.g., horseradish peroxidase or myeloperoxidase), which results in the conjugation of the compound to an amino acid comprising a phenol side chain via oxidative coupling.

Also provided herein is a method of preparing a bioconjugate, wherein the at least one AIEgen has the Formula 5, the method comprising: contacting a compound of Formula 5:

5

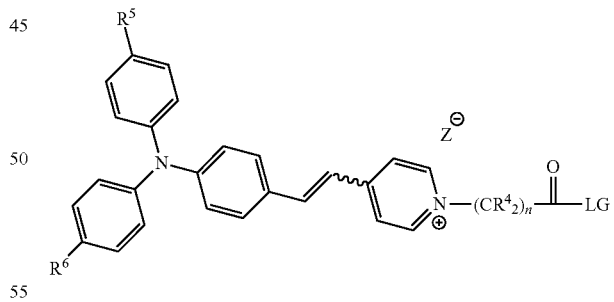

or a pharmaceutically acceptable salt thereof, wherein n is a whole number selected from 1-10;

LG is a leaving group;

each of $R^5$ and $R^6$ is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;

R[8] represents a moiety having the structure:

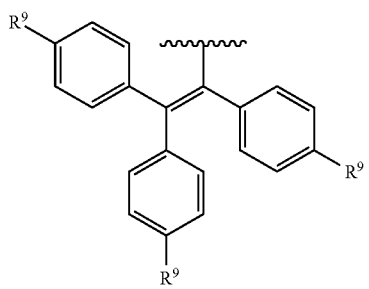

wherein R[9] for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl; and Z for each occurrence is independently a pharmaceutically acceptable anion; with a bacteriophage thereby forming the bioconjugate.

Exemplary leaving groups include, but are not limited to, Cl, Br, I, 3,5-dibromosalicylate, salicylate, or the like.

In certain embodiments, the leaving group is selected from the group consisting of:

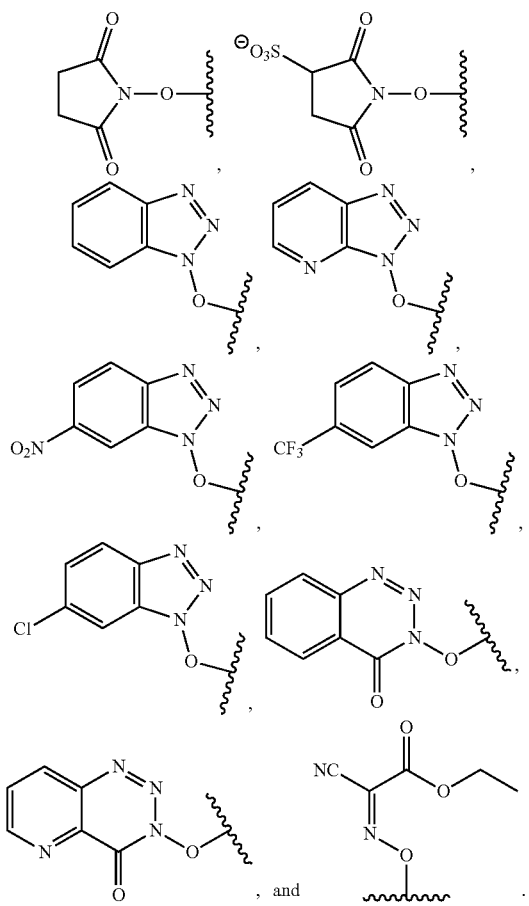

The compound of Formula 5 can be preformed or formed in situ, e.g., by reaction of the corresponding acid with a carbonyl activating agent and optionally a coupling additive.

Exemplary carbonyl activating agents include, but are not limited to, carbodiimide, such as DCC, DIC, EDC, CIC, BMC, CPC, BDDC, PIC, PEC, and BEM, a uronium/aminium salt, such as HATU, HBTU, TATU, TBTU, HAPyU, TAPipU, HAPipU, HBPipU, HAMBU, HBMDU, HAMTU, 5,6-B(HATU), 4,5-B(HATU), HCTU, TCTU, and ACTU, phosphonium salts, such as AOP, BOP, PyAOP, PyBOP, PyOxm, PyNOP, PyFOP, NOP, and PyClock, immonium salts, such as BOMI, BDMP, BMMP, BPMP, and AOMP.

Exemplary coupling additives include, but are not limited to, HOBt, 6-NO$_2$—HOBt, 6-Cl-HOBt, 6-CF$_3$—HOBt, HOAt, HODhbt, HODhat, HOSu, and Oxyma.

The preparation of the compound of Formula 5, including the appropriate selection of reagents and reaction conditions, is well within the skill of a person of ordinary skill in the art.

An intermediate useful in the preparation of the bioconjugates described herein is a compound of Formula 5:

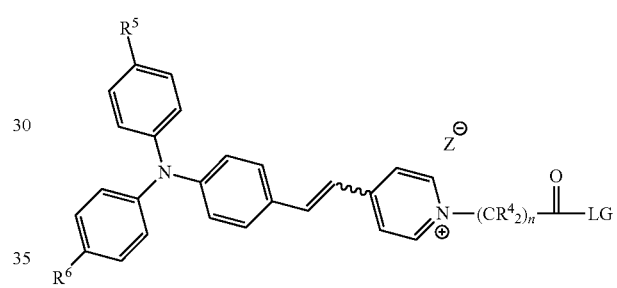

5 or a pharmaceutically acceptable salt thereof, wherein
n is a whole number selected from 1-10;
LG is a leaving group;
each of R[5] and R[6] is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, aryl, aralkyl, heterocycloalkyl, heteroaryl, and R[8];
R[8] represents a moiety having the structure:

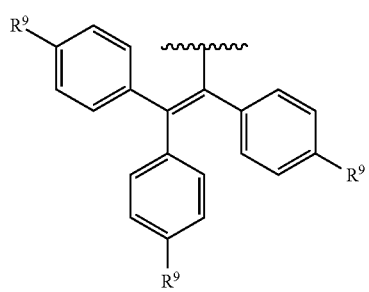

wherein R[9] for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl; and Z for each occurrence is independently an anion.

Also provided herein are methods of using the bioconjugates described herein as bacterial imaging agents and/or antibacterial agents.

In certain embodiments, the method of treating a bacterial infection comprises administering a therapeutically effective amount of a bioconjugate as described herein to the bacterial infection and irradiating the bacterial infection with electromagnetic radiation in the presence of oxygen. The bacterial cell may be Gram positive or Gram negative. In certain embodiments, the bacteria is multi-drug resistant. In certain embodiments, the bacterial cell is selected from the group consisting of *Pseudomonas aeruginosa*, *Acinetobacter baumannii*, *Staphylococcus aureus*, *Escherichia coli*, *Bacteroides intestinalis*, *Streptococcus suis*, *Pyogenic streptococcus*, and *Fusobacterium nucleatum*.

The method may be conducted in vivo or in vitro. The electromagnetic radiation may be white light. The oxygen present may be endogenous oxygen, exogenous oxygen, or a combination thereof.

In certain embodiments, provided herein is a method of prophylactically treating a potential bacterial infection in a subject in need thereof, the method comprising: contacting the site of the potential bacterial infection with a therapeutically effective amount of a bioconjugate described herein; and irradiating the site with electromagnetic radiation. The site of potential bacterial infection may be an injury, such as a cut that breaks the outer dermal layer of the skin, an animal bite, a dermal burn, or a surgical wound or incision that is highly susceptible to bacterial infection.

Also provided herein is a method of treating an aqueous solution with a bioconjugate described herein such that at least some or all of the bacteria that are present in the solution are killed. In certain embodiments, the method comprises contacting an aqueous solution suspected of containing bacteria with a therapeutically effective amount of a bioconjugate described herein and irradiating the aqueous solution with electromagnetic radiation. Treatment of the aqueous solution can reduce the chance of bacterial infection resulting from consumption of the aqueous solution. In certain embodiments, the aqueous solution is a solution that is subject to bacterial contamination, e.g., the water in a fish tank or wastewater, such as sewage.

In instances in which the method of treating a bacterial infection is conducted in vivo, provided herein is a method of treating a bacterial infection in a subject, the method comprising administering a therapeutically effective amount of a bioconjugate as described herein to the subject; and irradiating the site of bacterial infection with electromagnetic radiation.

The subject may be a cat, a dog, a cow, a horse, a pig, a mouse, a rat, a primate, or a human.

Also provided is a method of imaging a bacterial cell, the method comprising contacting a bioconjugate described herein with the bacterial cell; irradiating the bacterial cell with electromagnetic radiation; and detecting luminesence from the bioconjugate. The electromagnetic radiation can have an excitation wavelength between 250-700 nm; 400-600 nm; 400-650 nm, 450-600 nm, 450-550 nm; or 475-525 nm. The luminescence can have an emission wavelength between 300-750 nm; 425-700 nm; 475-650 nm; 300-500 nm; 300-450 nm; or 350-450 nm, or 375-425 nm. Any suitable means for detecting the luminescence can be used, such as a spectrometer.

Having described the invention, the following examples are given to illustrate specific applications of the invention including the best mode now known to perform the invention. These specific examples are not intended to limit the scope of the invention described in this application.

Experimental Section

Materials and Characterization

Sodium azide (NaN$_3$, 99%), dimethyl sulfoxide (DMSO, 99.7%), 3,3'-Dioctadecyloxacarbocyanine perchlorate (DiO), 2'-(4-Ethoxyphenyl)-5-(4-methyl-1-piperazinyl)-2,5'-bi-1H-benzimidazole trihydrochloride (Hoechst 33342, 97%), 2',7'-Dichlorofluorescin diacetate (DCFH, 97%), 9,10-Dimethylanthracene (ABDA, 99%) and Rose Bengal lactone (RB, 95%) were purchased from Sigma-Aldrich. Hydroxyphenyl fluorescein (HPF) and dihydrorhodamine 123 (DHR) were purchased from Thermal Fisher Scientific. 4-(N,N-Diphenylamino)benzaldehyde (98%), 4-Methylpyridine (98.5%), 4-bromobutanoic acid (98%), N,N-Dicyclohexylcarbodiimide (DCC, 99%), N-Hydroxysuccinimide (NHS, 98%), Potassium tert-butoxide (99%), Sodium chloride (NaCl, AR), Chloroform (CHCl$_3$), dichloromethane (DCM), tetrahydrofuran (THF), N,N-dimethylformamide (DMF), acetonitrile, ethanol and ethyl acetate were purchased from J&K. Phosphate buffered saline (10×PBS) was purchased from Thermo Scientific (HyClone). Other compounds were purchased from AIEgen Biotech. Co., limited. All other reagents and solvents are of analytical grade. Solvents including DCM and THF were distilled before using. Tryptone, yeast extract and Tryptic Soy Broth (TSB) broth were purchased from Oxoid Ltd (London, UK). Agar was obtained from Solarbio life science (Beijing, China). Cell Counting Kit-8 was purchased from MedChem Express (USA). *Pseudomonas aeruginosa* (*P. aeruginosa*, ATCC 27853), *Acinetobacter baumannii* (*A. baumannii*, ATCC 19606), and *Staphylococcus aureus* (*S. aureus*, ATCC 25923) strains were obtained from the American Type Culture Collection (ATCC). MDR *P. aeruginosa* was clinically isolated and identified by the Third Military Medical University. HaCaT cell line was purchased from the China center for type culture collection of Wuhan University. Water (18.2 MΩ·cm) was supplied by a Milli-Q Direct-8 purification system (Millipore). Enterobacteria phage P7 (Bacteriophage PAP7, "PAP") was a gift provided by the third Military Medical University (Chongqing, China), was isolated from the sewage of Southwest Hospital (Chongqing, China) on the basis of lambda bacteriophage isolation protocol. The bacteriophage titer was measured by the standard plaque assay.

Property Characterization

Fluorescence spectra and solid absolute quantum yield were recorded using a Horiba FluoroLog-3 fluorescence spectrophotometer. The delayed PL spectra and phosphorescence lifetime were measured on an Edinburgh FLSP 980 fluorescence spectrophotometer equipped with a xenon arc lamp (Xe900) and a microsecond flash-lamp (uF900). Absolute PL quantum yields were measured using a Hamamatsu absolute PL quantum yield spectrometer C11347 Quantaurus_QY UV-vis spectra were measured with a Shimadzu UV-2550 spectrophotometer (Shimadzu Co, Kyoto, Japan). X-ray diffraction (XRD) measurement was performed on a PANalytical X'pert PRO Multiple Crystals (powder) X-ray Diffractometer with 3.0 mg dry powder sample. Hydrodynamic size was measured on Zetasizer Nano ZS90 (Malvern) with 900 scattering angle and a He—Ne laser.

The AIE property of TVP-S was demonstrated by studying its fluorescence behavior in a mixture of DMSO and chloroform with different volume ratios. Each group contained 10 μM AIEgens and the FL spectra were collected under 460 nm excitation.

Measurement of ROS Generation

DCFH was used to measure the generated total ROS. A DCFH stock solution (1.0 mM, 10 μL) was added into the AIEgens contained suspensions in 1×PBS buffer (5.0 μM, 2.0 mL), and white light (4.2 mW/cm$^2$) was used to irradiate the suspensions. The FL intensity of DCFH at 524 nm (488 nm excitation) was recorded at desired time points. Similarly, HPF stock solution (5.0 mM, 2.0 μL) and DHR stock solution (10 mM, 1.0 μL) were added to the AIEgens contained suspensions in 1×PBS buffer (5.0 μM, 2.0 mL) with excitation wavelength at 490 nm and 505 nm, and the emission maximum intensities were employed for the tracking of the generation of hydroxyl radical (OH$^\bullet$) and superoxide ($O_2^{\bullet-}$), respectively. ABDA indicator was used to monitor the $^1O_2$ generation. ABDA stock solution (5.0 mM, 4.0 μL) was added into the AIEgens contained suspensions (5.0 μM, 2.0 mL), and white light (4.2 mW/cm$^2$) was used for the irradiation. The absorbance at 378 nm was recorded at various irradiation times.

Preparation of TVP-PAP Bioconjugates and Molar Ratio Quantitation

Typically, 4.0 μL TVP-S solution (1.0 mM) suspended in DMSO were mixed with 996 L PAP solution (8.48×10$^{10}$ PFU·mL$^{-1}$), followed by a 24 h reaction at 4° C. The produced TVP-PAP bioconjugates were then purified with free AIEgens extracted by chloroform (PBS: Chloroform=50:100 (v v) for three times). According the standard absorbance-concentration curve of AIEgen and PAP, the quantitation of the molar ratio of AIEgen molecule to PAP entity could then be calculated via the difference of absorbance at 457 nm.

Bacteria Culturing, Imaging, and Real-Time Tracking

*P. aeruginosa*, MDR *P. aeruginosa*, and *A. baumannii* were cultured in the LB medium at 37° C. with a shaking speed of 180 rpm. *S. aureus* was cultured in the TSB (Tryptic Soy Broth, OXO) medium at 37° C. The bacteria were then harvested via centrifugation (5000 rpm for 6 min) to completely remove the culture media, and resuspended in PBS buffer ready for the following experiments. The concentrations of the bacterial suspension were determined via optical density measurements of absorbance at 600 nm wavelength using a cell density meter (Amersham Bioscience, Ultrospec 10). For the co-staining experiment with cell membrane and nucleus dyes, 1.0 mL of bacterial suspension (1.0×10$^8$ CFU·mL$^{-1}$) was first incubated with DiO (30 nM) and Hoechst 33342 (20 nM) at 37° C. for 30 min. After washing for three times, the collected pellet was then mixed with 1.0 mL of TVP-PAP probe (1.0×10$^9$ PFU·mL$^{-1}$) in PBS for another 20 min at 37° C. To perform the fluorescence imaging of bacteria, 1.0 μL of stained bacteria solution was dropped onto the microscope slide and covered by a coverslip. The samples were kept under darkness during the whole process of real-time tracking of targeted staining with fluorescence pictures taken at desired time points. For long-time tracking of the killing process upon TVP-PAP treatment, 5.0 μL of bacterial solution was swiftly dropped onto the microscope slide after mixed with the TVP-PAP probes without cover slip immobilization. And the white light irradiation started from 30 min and continued to 80 min with fluorescence pictures taken at desired time points. The images were collected using confocal laser scanning microscope (CLSM, TCS SP8, Leica, Germany) or inverted fluorescence microscope with a mercury lamp (DMi 8, Leica, Germany) according to the request of experiments. Under CLSM imaging, 63× or 100× oil immersion objectives were employed.

In Vitro Antibacterial Assay

The antibacterial activities of PAP, TVP-S and TVP-PAP were evaluated by traditional plating method, respectively. For the group of TVP-PAP in the darkness, 1.0×10$^5$ CFU·mL$^{-1}$ bacteria were treated with various concentrations of TVP-PAP (3.18×10$^5$, 6.36×10$^5$, 9.54×10$^5$, 1.272×10$^6$, 1.59×10$^6$ PFU·mL$^{-1}$ for *P. aeruginosa*, 1.59×10$^7$, 3.18×10$^7$, 4.77×10$^7$, 6.36×10$^7$ PFU·mL$^{-1}$ for MDR *P. aeruginosa*, respectively) for 30 min at 37° C., respectively. Then, the bacteria suspensions were then diluted by 10-fold using 1×PBS buffer. 100 μL of diluted bacteria was spotted onto LB plates with triplicated parallel groups. After cultivation for overnight at 37° C., the surviving number of colony forming units (CFU) on each plate was then enumerated by viable counting. The survival rate was calculated based on the equation [B/A]×100%, where A was the mean number of bacteria colonies in the control sample (only bacteria), and B was the mean number of bacteria after incubation with TVP-PAP. For the group of TVP-PAP under irradiation, the bacteria were incubated for 30 min at 37° C. and then illuminated with white light for another 30 min. The calculated concentrations of AIEgens were 4.33, 8.66, 12.99, 17.32, 21.65 pM, corresponding to 3.18×10$^5$, 6.36×10$^5$, 9.54×10$^5$, 1.272×10$^6$, 1.59×10$^6$ PFU·mL$^{-1}$ TVP-PAP in the group of wild-type *P. aeruginosa*, respectively; and 217, 433, 650, 866 pM, corresponding to 1.59×10$^7$, 3.18×10$^7$, 4.77×10$^7$, 6.36×10$^7$ PFU·mL$^{-1}$ TVP-PAP in the group of MDR *P. aeruginosa*, respectively). And the molar concentration of PAP equaling to the corresponding TVP-PAP concentration in each group.) were separately treated as control experiments.

Influence of Treatment Sequence on the Antibacterial Activity of TVP-PAP

For the incubation-irradiation group, varying concentrations of TVP-PAP (9.54×10$^5$, 1.272×10$^6$, and 1.59×10$^6$ PFU·mL$^{-1}$) were incubated with 200 μL bacterial suspension (1.0×10$^5$ CFU·mL$^{-1}$), respectively, for 30 min. And they were then irradiated under white light for 30 min. As to the irradiation-incubation group, the same concentrations of the TVP-PAP were firstly irradiated under white light for 30 min, then mixed with the volume of bacterial suspension, respectively. Then, the antibacterial efficiencies were evaluated by agar plate dilution method. Each experiment was designed with triplicated parallel groups.

Scan Electron Microscopy (SEM)

100 μL (2.0×10$^4$ CFU·mL$^{-1}$) of bacteria suspension was pipetted on the sterilized slide putted into the 6-well plates. Then the bacteria were cultured for 12 h at 37° C. and washed with PBS before addition of TVP-PAP solution. After incubation at 37° C. for 30 min, the treated bacteria were then exposed to white light for another 30 min. Following washing with PBS for two times, the bacteria were fixed with 4% glutaraldehyde for overnight at 4° C. Then the bacteria were washed with sterile water, sequentially dehydrated by different content of ethanol (30%, 50%, 70%, 80%, 90%, 95% and 100%, v/v, respectively). The final samples were dried in critical point drying oven and then characterized by SEM with 5 kV operation voltage (Hitachi, SU8010).

Mammalian Cell Culture and Cytotoxicity Assay of TVP-PAP

HaCaT cells were cultured on 25 cm$^2$ cell culture plates with vent caps (Corning) in DMEM supplemented with 10% fetal bovine serum. All the cells were grown in a humidified incubator at 37° C. containing $CO_2$ (5%). The cells that grew to subconfluence were dissociated from the surface with a solution of 0.25% trypsin/EDTA. Then aliquots of cells were seeded in 96-well plates ($5 \times 10^3$ cell per well) and grown for required duration in FBS-containing cell media before experiments. After removing the medium, 100 μL of various concentrations of TVP-PAP were added and co-incubated with the bacteria for 30 min in the dark. For the irradiation group, the TVP-PAP-treated cells were exposed to white light for 30 min. For the control group, the TVP-PAP-treated cells were kept in darkness for 30 min. Cell viability was then assayed by CCK-8 method. Detailly, 100 μL fresh medium containing 10 μL CCK-8 solution was added into each well and incubated at 37° C. for 2 h, with the absorbance at 450 nm was recorded using a microplate reader (Multiscan GO, Thermo Scientific). The cell viability in each group was comparing the control group without TVP-PAP treatment in the darkness or white light irradiation, respectively.

In Vivo Antibacterial Assay

All procedures of animal experiments were approved by the Animal Care and Use committee of Chongqing Medical University and complied with all relevant ethical regulations. Female BALB/c mice (6-8 week) were purchased from Experimental Animal Central of Chongqing Medical University. BALB/c mice were randomly divided into three groups: (1) bacteria-infected group with TVP-PAP treatment and white light irradiation; (2) bacteria-infected group with TVP-PAP alone treatment; (3) bacteria-infected group without any treatment (n=5 in each group). The mice were anesthetized by injection of 1.5% pentobarbital sodium. Then two full-thickness injuries (~6 mm diameter) on each mouse were created. The bacteria-infected wound models were established by inoculating with 20 μL bacteria suspension ($1.0 \times 10^9$ CFU·mL$^{-1}$ of P. aeruginosa or $1.0 \times 10^8$ CFU mL$^{-1}$ of MDR P. aeruginosa) on the surface of wounds. After 12 h postinfection, 20 μL of PBS or TVP-PAP ($1.6 \times 10^{10}$ PFU·mL$^{-1}$ for P. aeruginosa group and $6.4 \times 10^{10}$ PFU·mL$^{-1}$ for MDR P. aeruginosa group) was added onto wound and kept for 30 min. Subsequently, the wounds were irradiated by white light (~4.2 mW·cm$^{-2}$) for 30 min or kept under darkness. The treatment of TVP-PAP injection and with or without white light irradiation were performed in the first day and continued for another two days with total three times. The wound healing processes were dynamically monitored through measurements of the wound size by a Vernier caliper. At the 8 day, all the infection tissues were harvested and homogenized for further evaluation. The bacteria burden of infection tissue of each mouse was evaluated by agar plate dilution method.

Synthesis

Synthesis of Compound TVP-S is According to FIG. 1

Synthesis of compound 1. The solvent of DMF (10 mL) was added 4-methylpyridine (800 L, 8.1 mmol) and potassium tert-butoxide (200 mg, 1.78 mmol) and stirred for 30 min in the room temperature. Then the mixture was added 4-(N, N-diphenylamino)benzaldehyde (1.1 g, 4.02 mmol), and stirred under room temperature for overnight. The reaction was then quenched by 30 mL saline, and the compound was extracted with ethyl acetate (EA). The collected organic layer was dried by anhydrous sodium sulfate and evaporated to dryness. The residue was subjected to column chromatography using EA and n-hexane mixture (1:6, v v) as eluent to afford compound 1 as a yellow solid (1.29 g, 3.71 mmol) in 92.3% yield. $^1$H NMR (Bruker Avance, 400 MHz, CDCl$_3$), δ (ppm): 8.56 (s, 2H), 7.41-7.22 (m, 9H), 7.13-7.04 (m, 7H), 6.90-6.86 (m, 2H); $^{13}$C NMR (Bruker Avance, 100 MHz, CDCl$_3$), δ (ppm): 148.5, 147.3, 132.7, 129.8, 129.4, 128.0, 124.9, 123.9, 123.5, 122.8. HRMS (EI): calculated for $C_{25}H_{20}N_2$ [M$^+$]: 348.1626; found: 348.1628.

Synthesis of compound 2. The solvent of THF (50 mL) was added 4-bromobutanoic acid (2.0 g, 12.0 mmol), N-hydroxysuccinimide (1.44 g, 12.5 mmol) and N,N'-dicyclohexylcarbodiimide (2.97 g, 14.4 mmol) and stirred for 12 hours in the room temperature. The collected organic layer was evaporated to dryness. And the residue was subjected to column chromatography using EA and n-hexane mixture (1:4, v v) as eluent to afford a yellow colored crude compound 2 for the next step reaction.

Synthesis of TVP-S. The solvent of acetonitrile (10 mL) was added compound 1 (200 mg, 0.58 mmol) and compound 2 (226 mg, 0.86 mmol) and stirred for 24 hours in the room temperature. The product was precipitated out by evaporated to dryness. The residue was subjected to column chromatography using DCM and methanol mixture (95:5, v v) as eluent to afford TVP-S as a red solid (299.5 g, 0.49 mmol) in 84.5% yield. $^1$H NMR (Bruker Avance, 400 MHz, CDCl$_3$), δ (ppm): 9.16 (s, 2H), 7.98 (s, 2H), 7.71-7.67 (m, 1H), 7.50-7.47 (m, 3H), 7.31-7.20 (m, 6H), 7.12-6.96 (m, 8H), 4.92 (s, 2H), 2.88-2.85 (m, 6H), 2.48 (s, 8H); $^{13}$C NMR (Bruker Avance, 100 MHz, CDCl$_3$), δ (ppm): 169.6, 167.9, 154.0, 150.6, 146.4, 144.1, 142.0, 130.0, 129.6, 127.3, 125.8, 124.6, 123.7, 121.0, 119.3, 58.3, 27.8, 26.7, 25.8. HRMS (EI): calculated for $C_{33}H_{30}BrN_3O_4$[M−Br]$^+$: 532.2231; found: 532.2218.

AIEgen Property Characterizations, and Bio-conjugation with Bacteriophage

Figure 2:
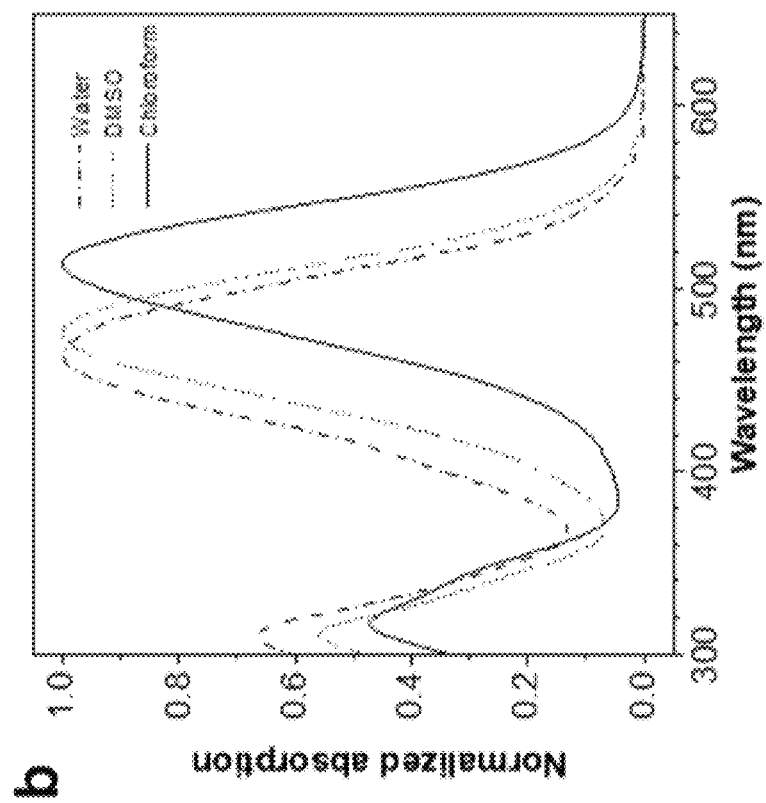
FIG. 2 depicts (a) molecular structure of AIEgen (TVP-S). (b) Normalized UV-vis spectra of TVP-S dissolved in water, DMSO and chloroform, respectively. (c) AIE curve of TVP-S in the mixture of DMSO and CHCl$_3$ with varying volume fraction. (d) Plotting of the emission maximum of TVP-S versus the fraction of the DMSO/CHCl$_3$ mixture. (e) Photodegradation of ABDA with TVP-S under white light irradiation in water. (f) Decomposition rates of ABDA with light irradiation at 379 nm absorbance.
Figure 2:
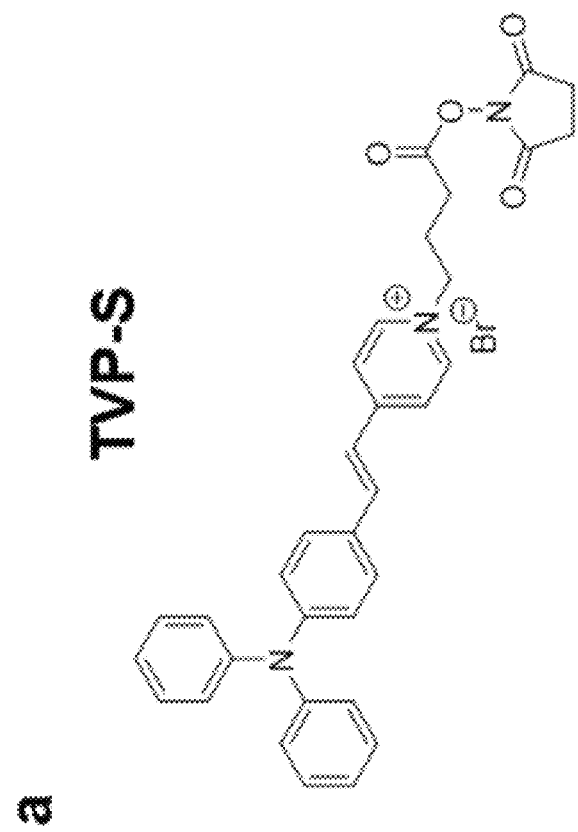
Figure 2:
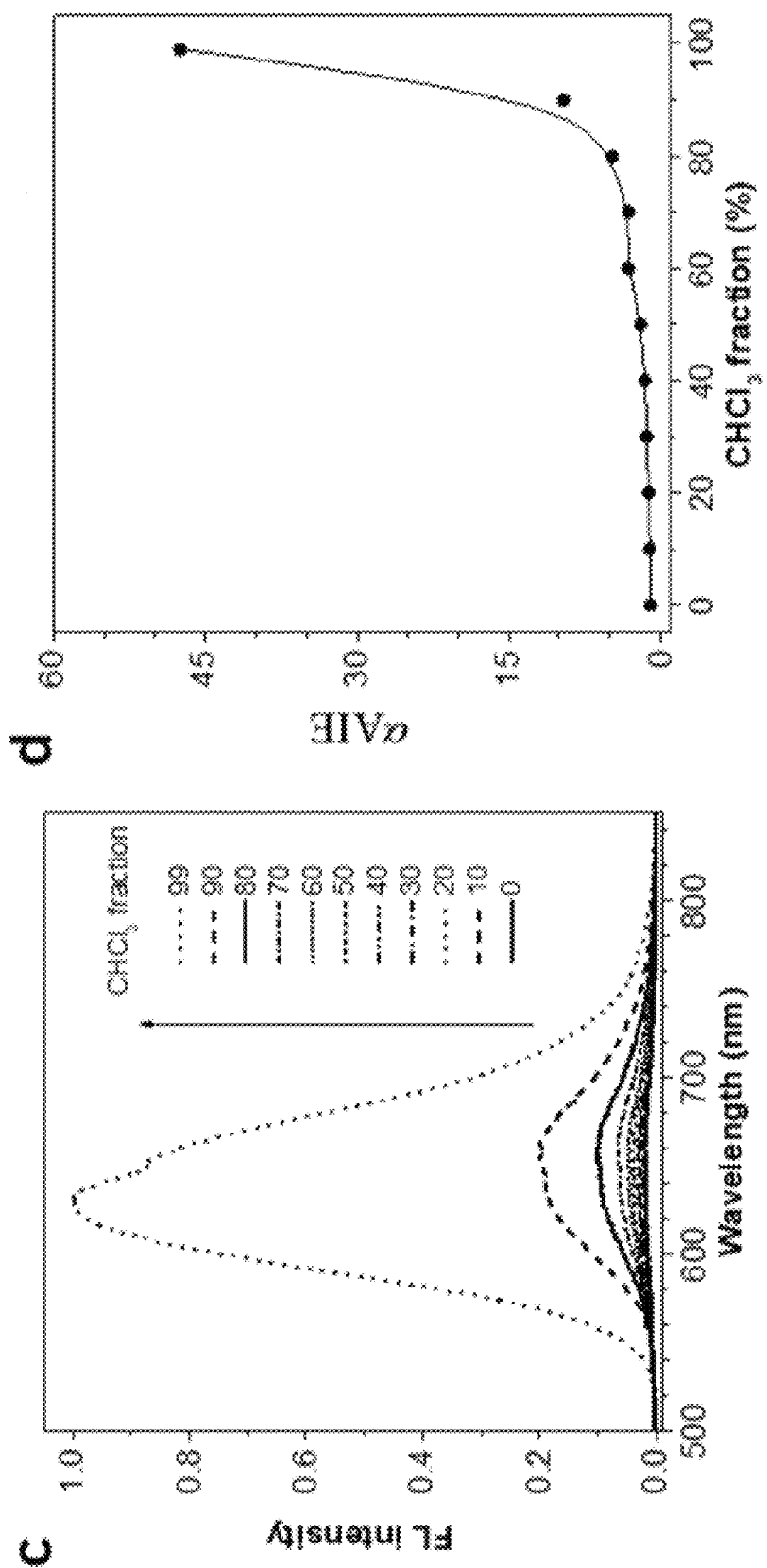
Figure 2:
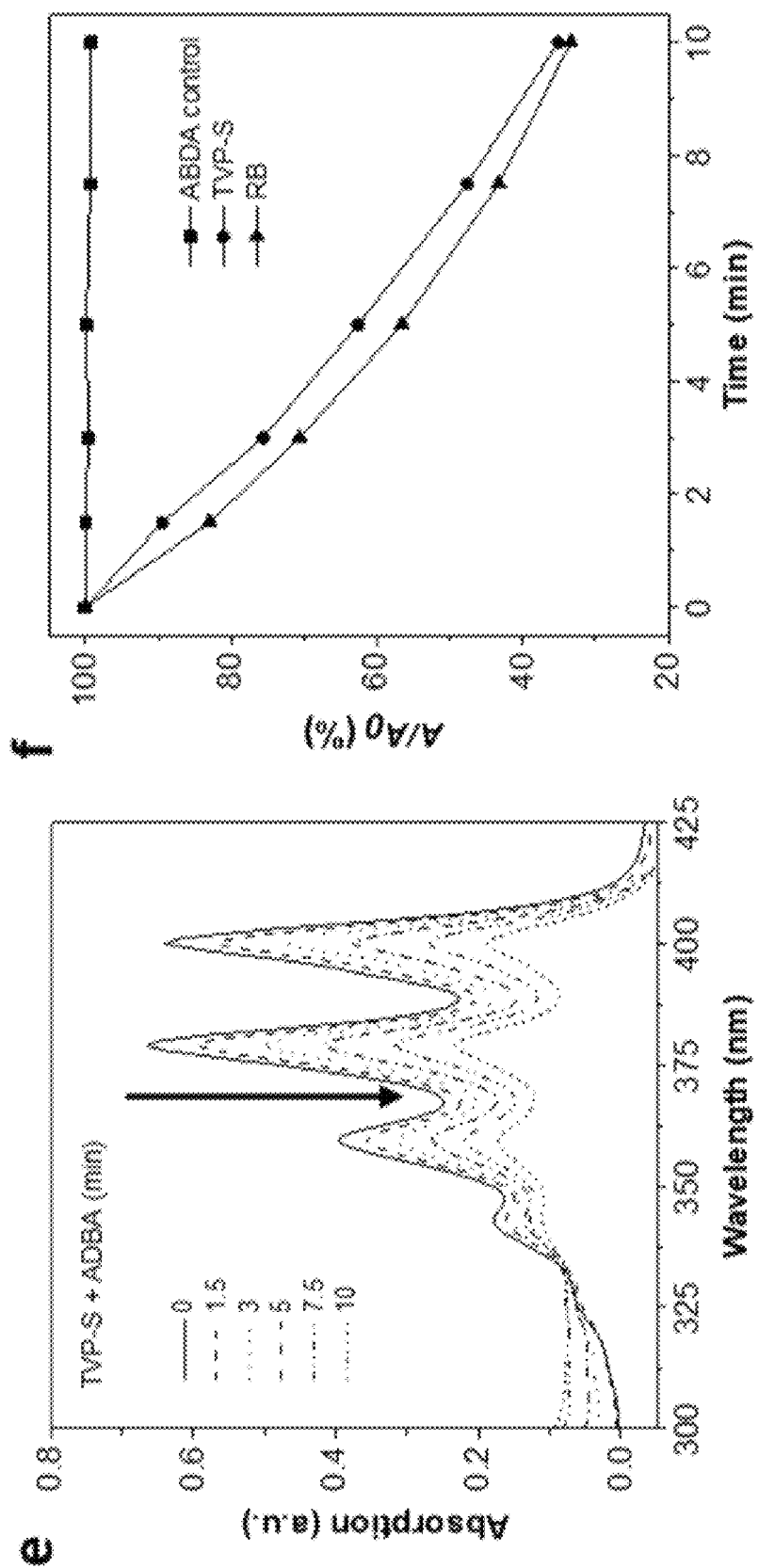
Figure 3:
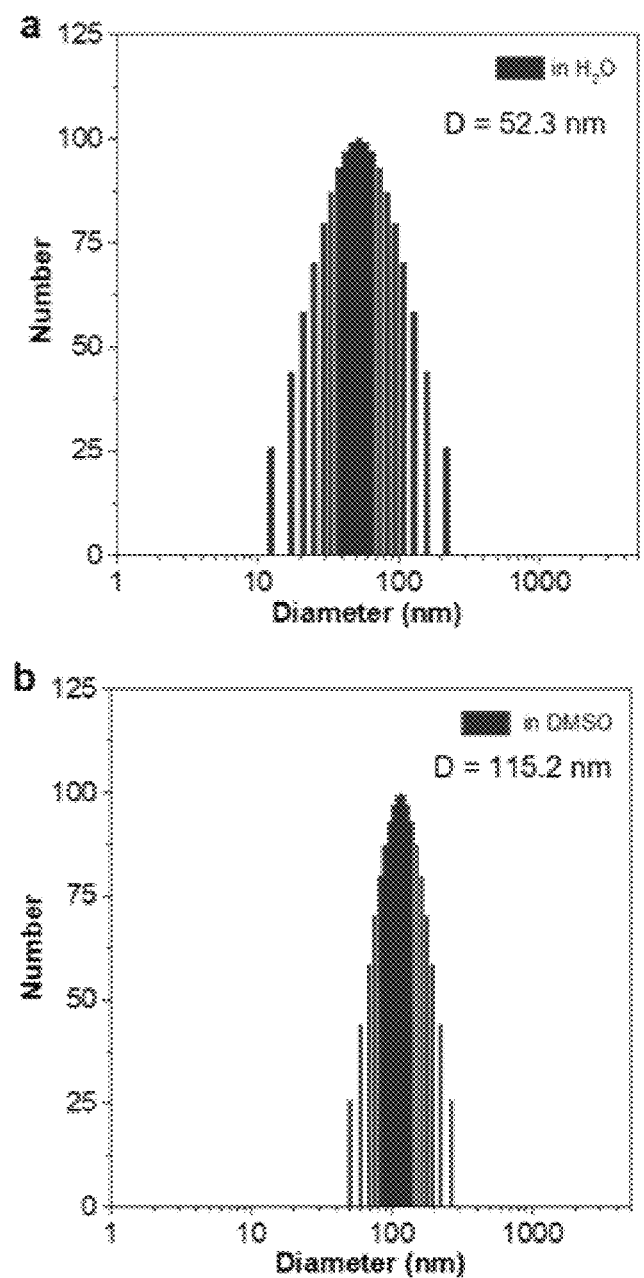
FIG. 3 DLS measurement of TVP-S dissolved in (a) water, (b) DMSO and (c) chloroform, respectively.
Figure 3:
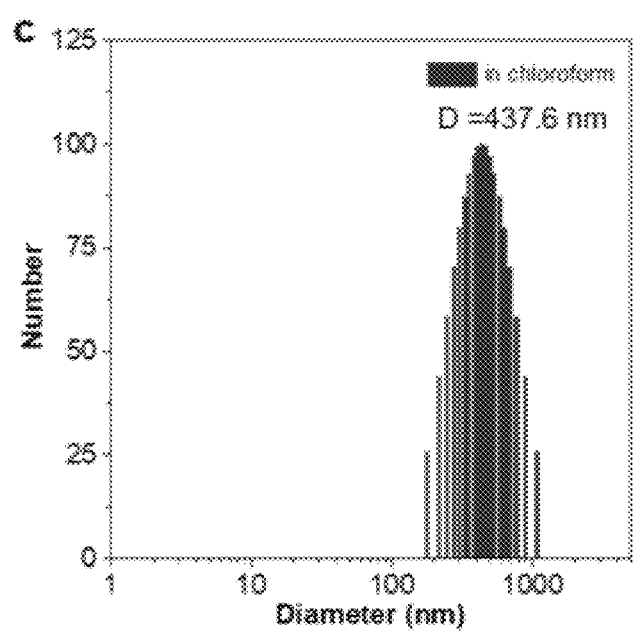

Attributed to the existence of positively charged pyridinium group and the hydrophilic carboxyl group in its structure, TVP-S could be well dissolved in high polarity solvent including water. More importantly, the activated carboxyl group in TVP-S structure endows it capability to straight-forwardly react the amino group that is widespread in the bioorganism. The obvious absorbance of TVP-S in the range between 400 and 600 nm with a maximum at 457 nm showed its strong capability of visible light absorption (FIG. 2b). As TVP-S could be well dissolved in solvent with large polarity, we investigated its AIE features in dimethyl sulfoxide (DMSO)/chloroform (CHCl$_3$) mixtures via varying the fractions of CHCl$_3$. As shown in FIG. 2c, TVP-S exhibited an apparent AIE property. Fluorescence could hardly be observed when it was dissolved in a good solvent, DMSO, whereas strong aggregated-state emission with 47 times enhancement in intensity appeared when the fraction of chloroform reached 99% (FIG. 2d). Their maximum emissions in the aggregation state are located at 630 nm, indicating its long-wavelength emission properties and large Stokes shifts. The significant increase in the absolute fluorescence quantum yield of TVP-S in Chloroform (33.3%) versus in DMSO (1.6%), further verified its typical AIE feature. Moreover, dynamic light scattering (DLS) analysis was performed to confirm the aggregation process by decreasing the solvent polarity, with obvious increasements in the average hydrodynamic diameters (FIG. 3).

Figure 4:
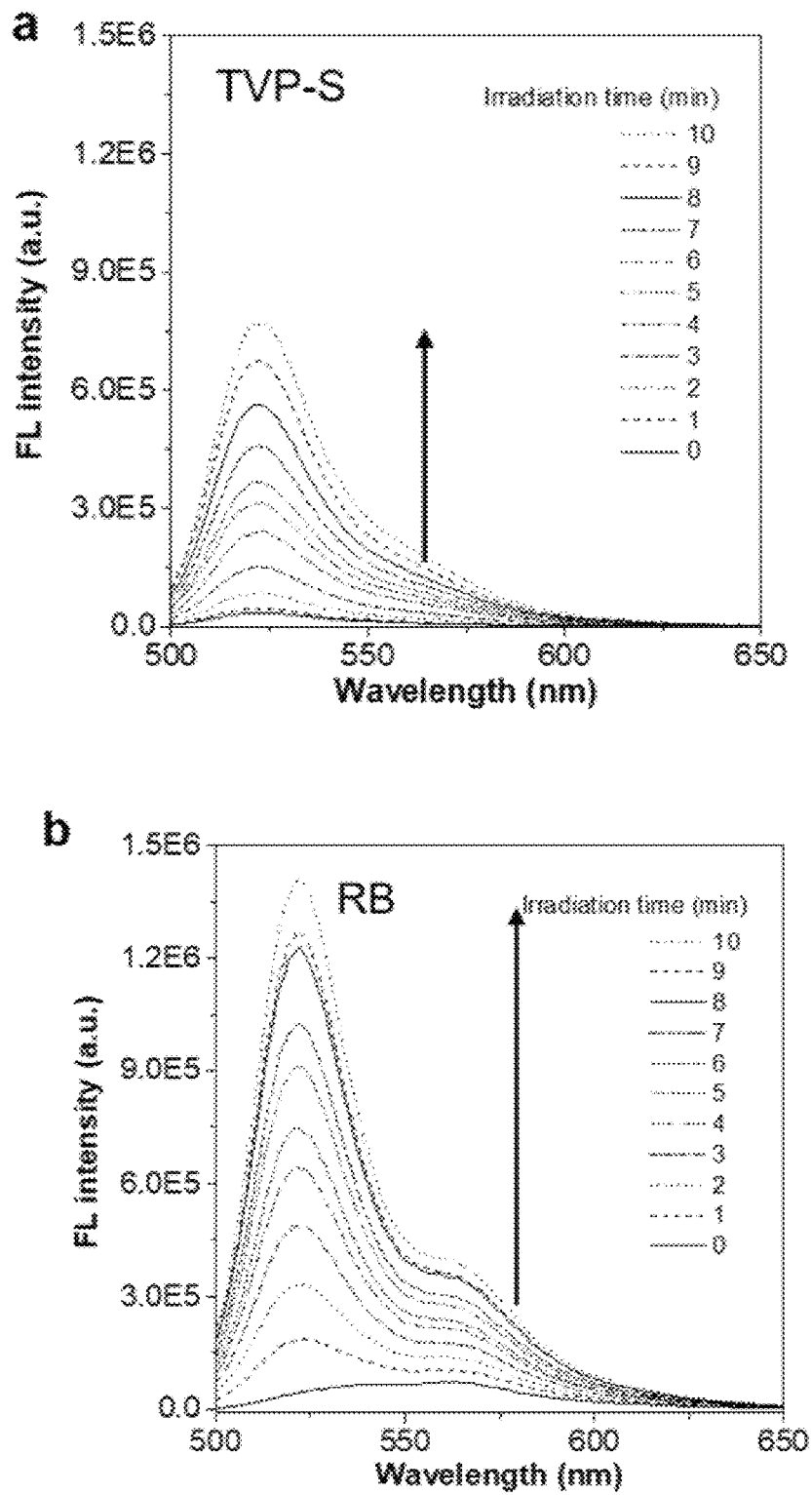
FIG. 4 depicts chemical trapping of total ROS generation. Photoactivation of DCFH with TVP-S (a), Rose Bengal (b), and DCFH control (c). These measurements were carried out under white light irradiation in 1×PBS buffer. (d) Activation rates of DCFH with light irradiation under different conditions at 524 nm emission.
Figure 4:
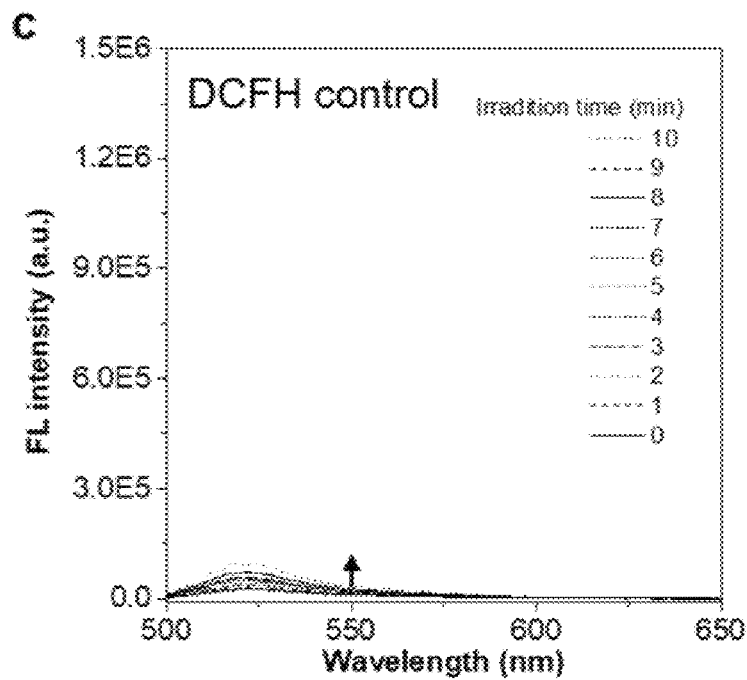
Figure 4:
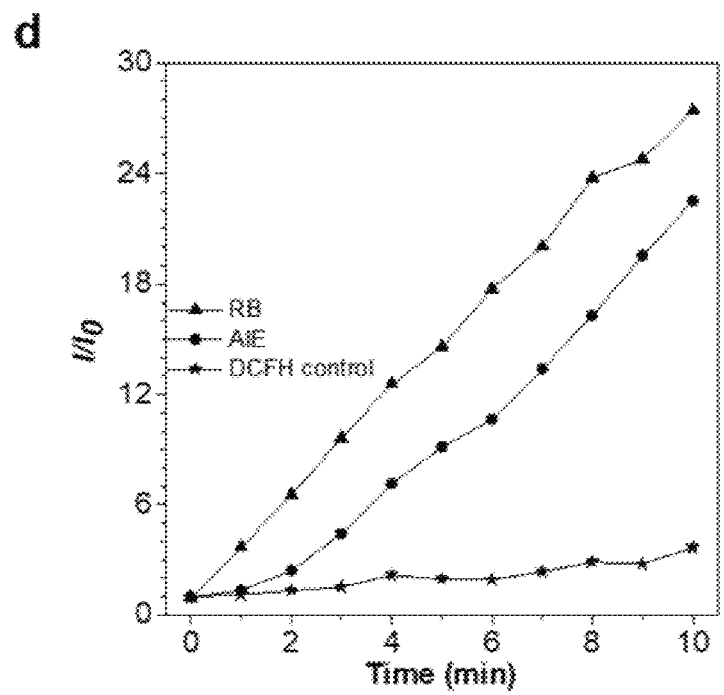
Figure 5:
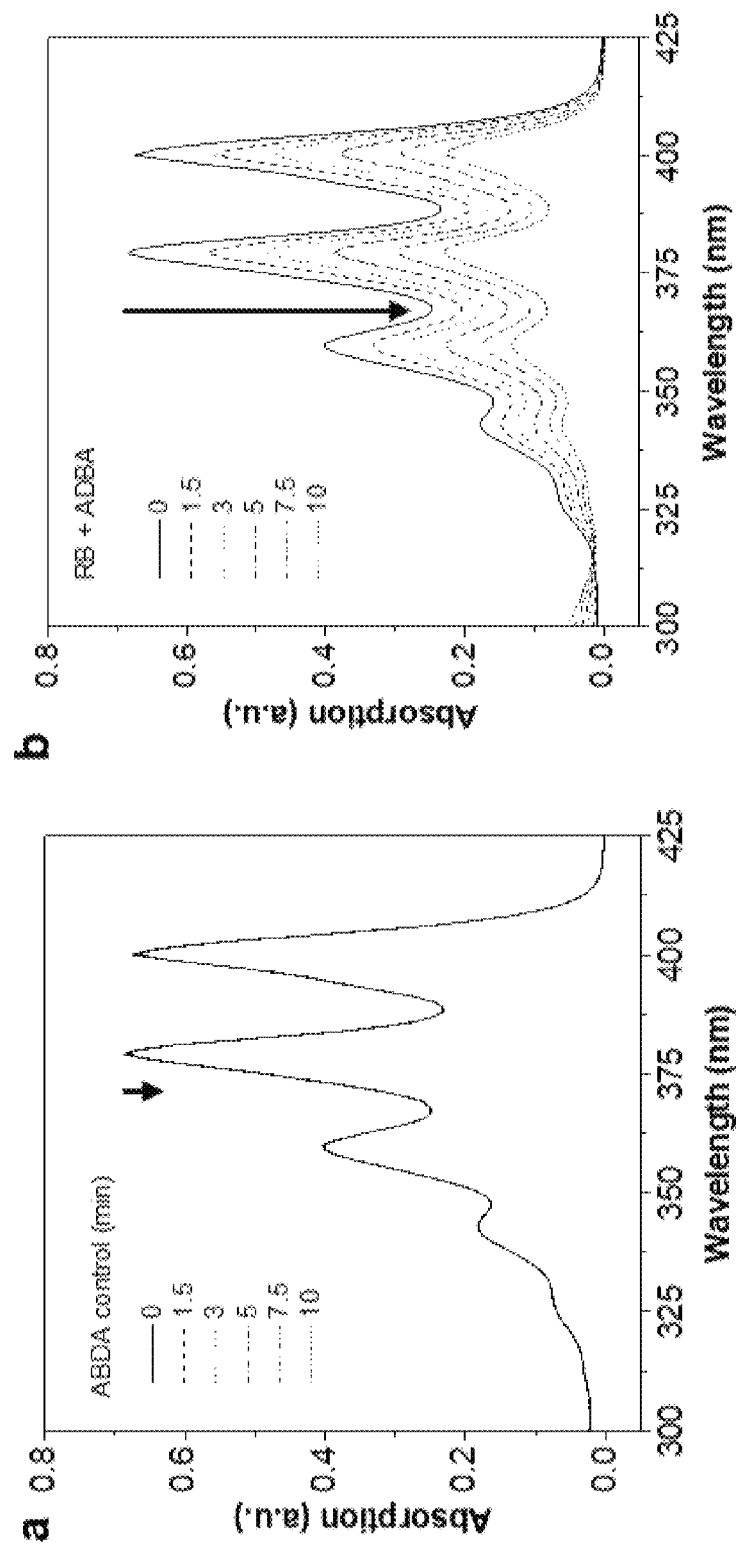
FIG. 5 depicts chemical trapping of the $^1O_2$ generation. Photodegradation of ABDA control (a) ABDA and Rose Bengal (b). These measurements were carried out under white light irradiation in water.
Figure 6:
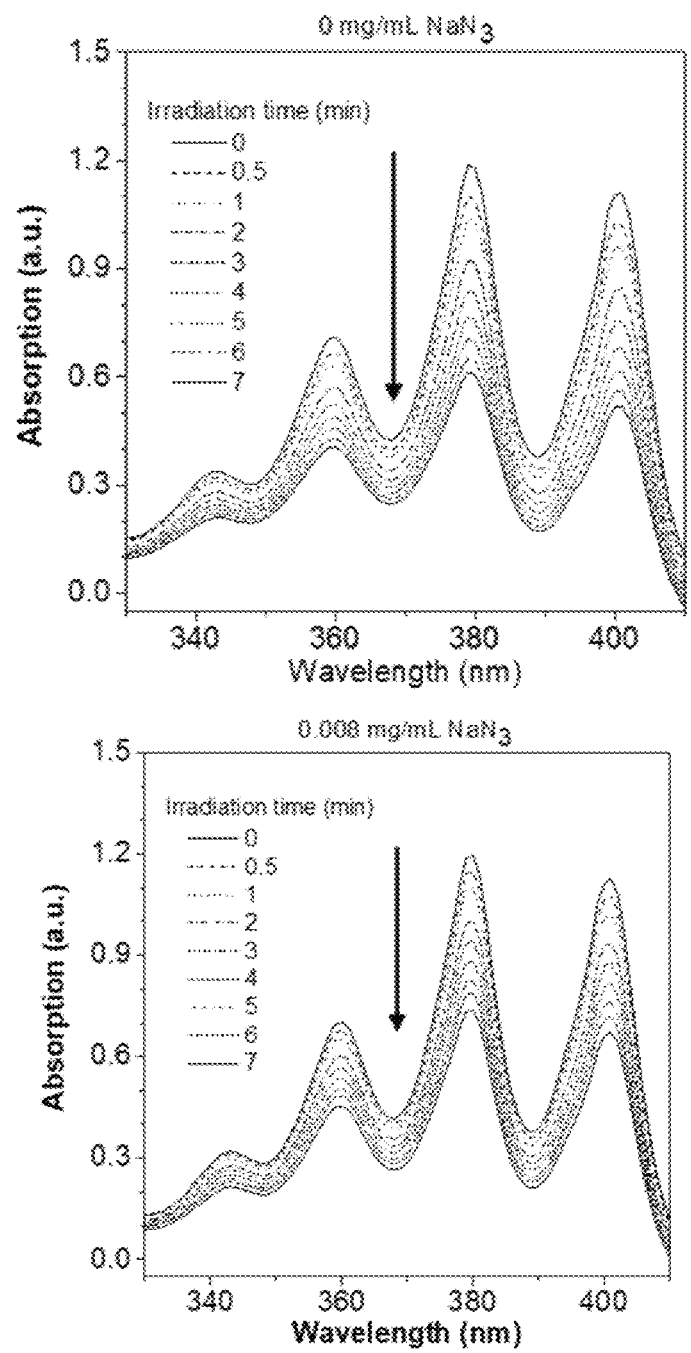
FIG. 6 depicts chemical trapping of the $^1O_2$ generation inhibited by various concentrations of NaN$_3$ via monitoring the photodegradation of ABDA with TVP-S. These measurements were carried out under white light irradiation. And the decomposition rates of ABDA with light irradiation under different conditions at absorbance of 379 nm.
Figure 6:
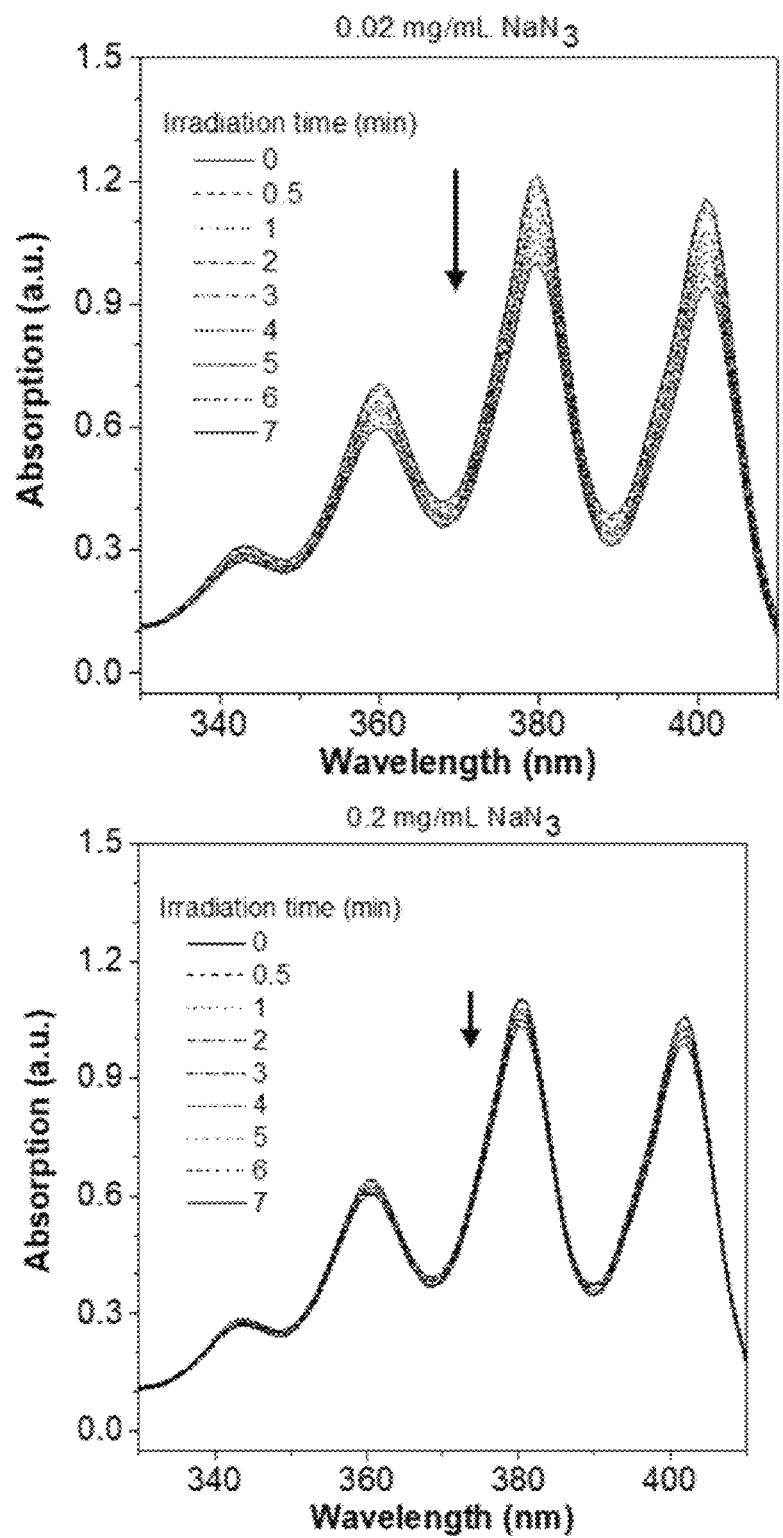
Figure 6:
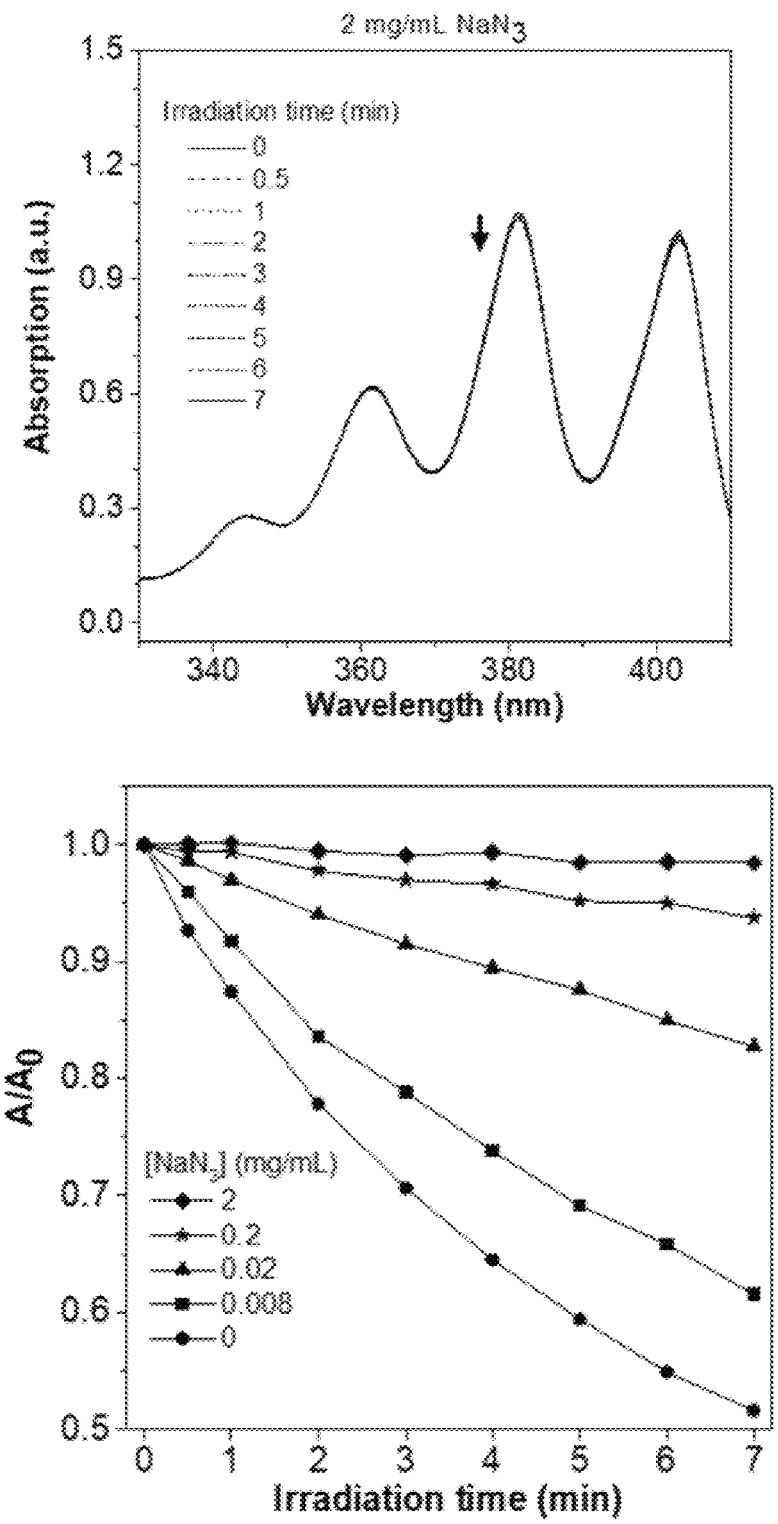
Figure 7:
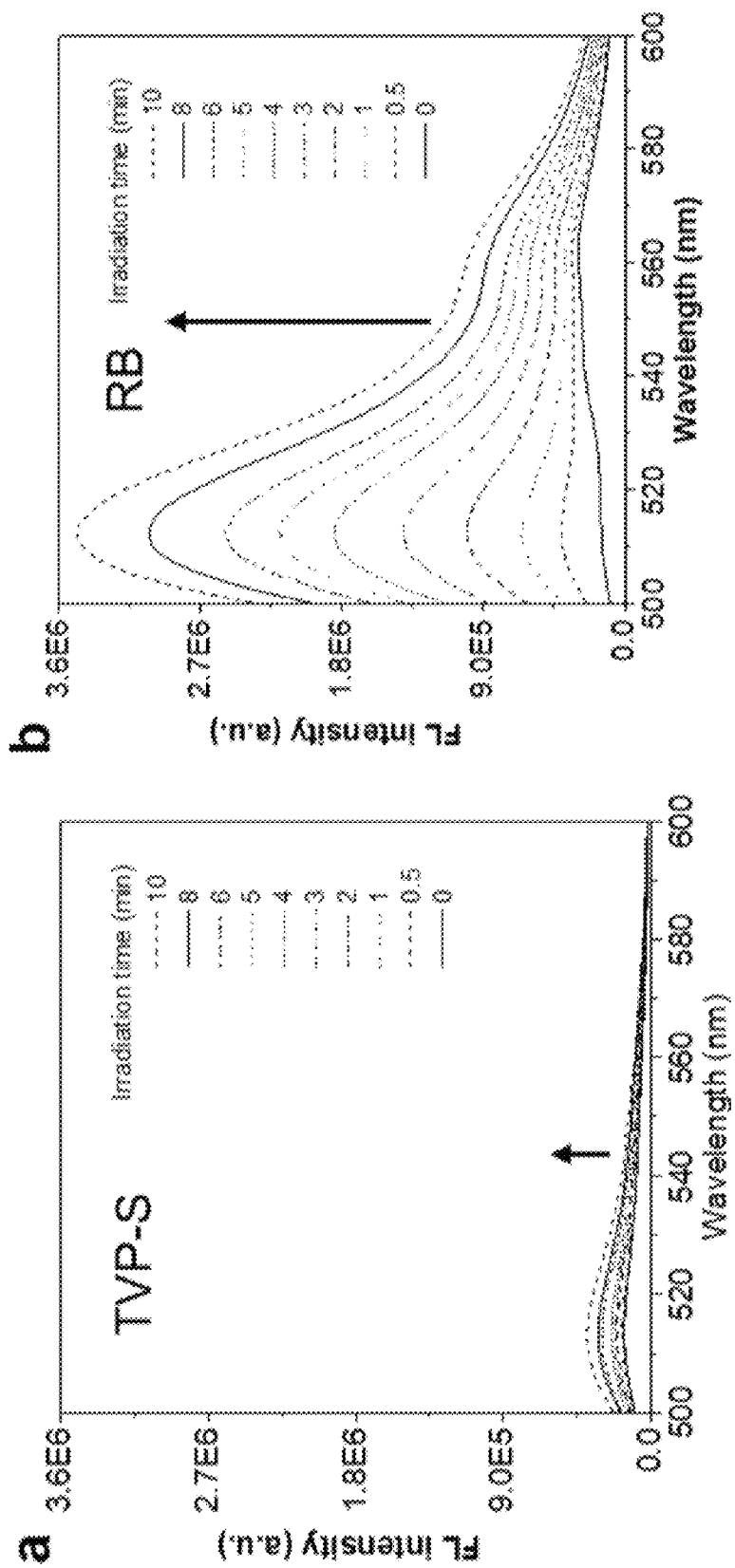
FIG. 7 depicts chemical trapping of the OH$^\bullet$ generation. Photoactivation of HPF with TVP-S (a), Rose Bengal (b), and HPF control (c). These measurements were carried out under white light irradiation in 1×PBS buffer. (d) Activation rates of HPF with light irradiation under different conditions at 515 nm fluorescence emission.
Figure 7:
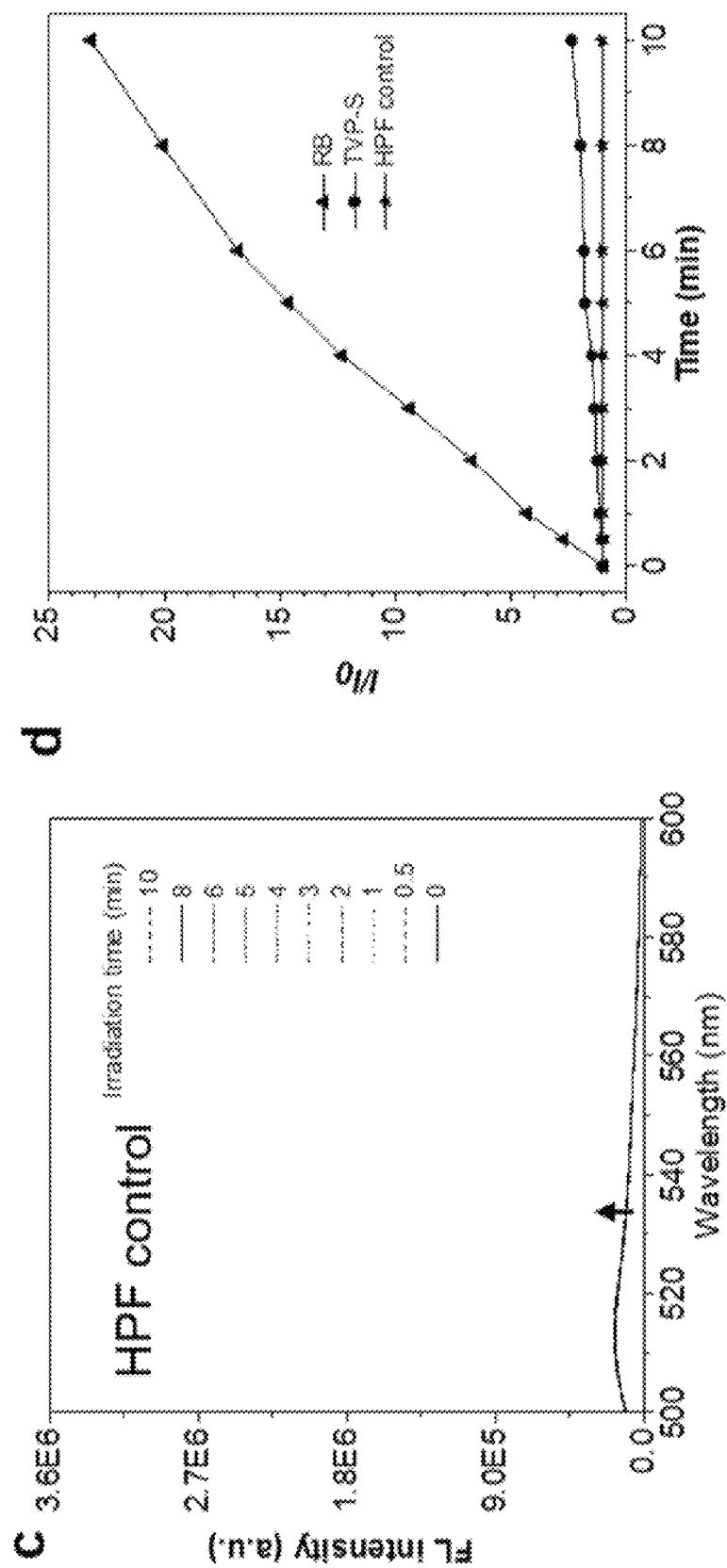
Figure 8:
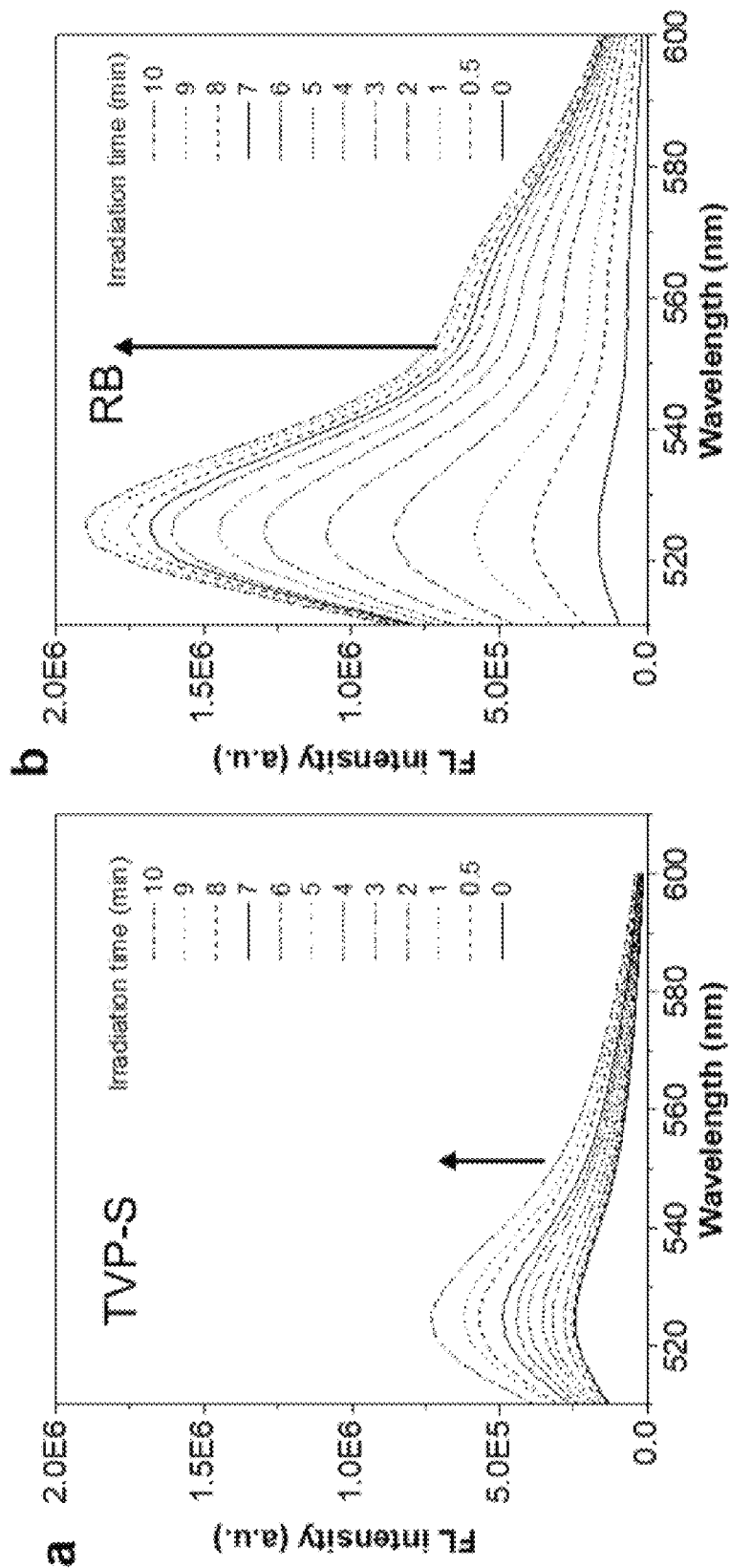
FIG. 8 depicts chemical trapping of the O2$^{\bullet-}$ generation. Photoactivation of DHR with TVP-S (a), Rose Bengal (b), and DHR control (c). These measurements were carried out under white light irradiation in 1×PBS buffer. (d) Activation rates of HBF with light irradiation under different conditions at 524 nm fluorescence emission.
Figure 8:
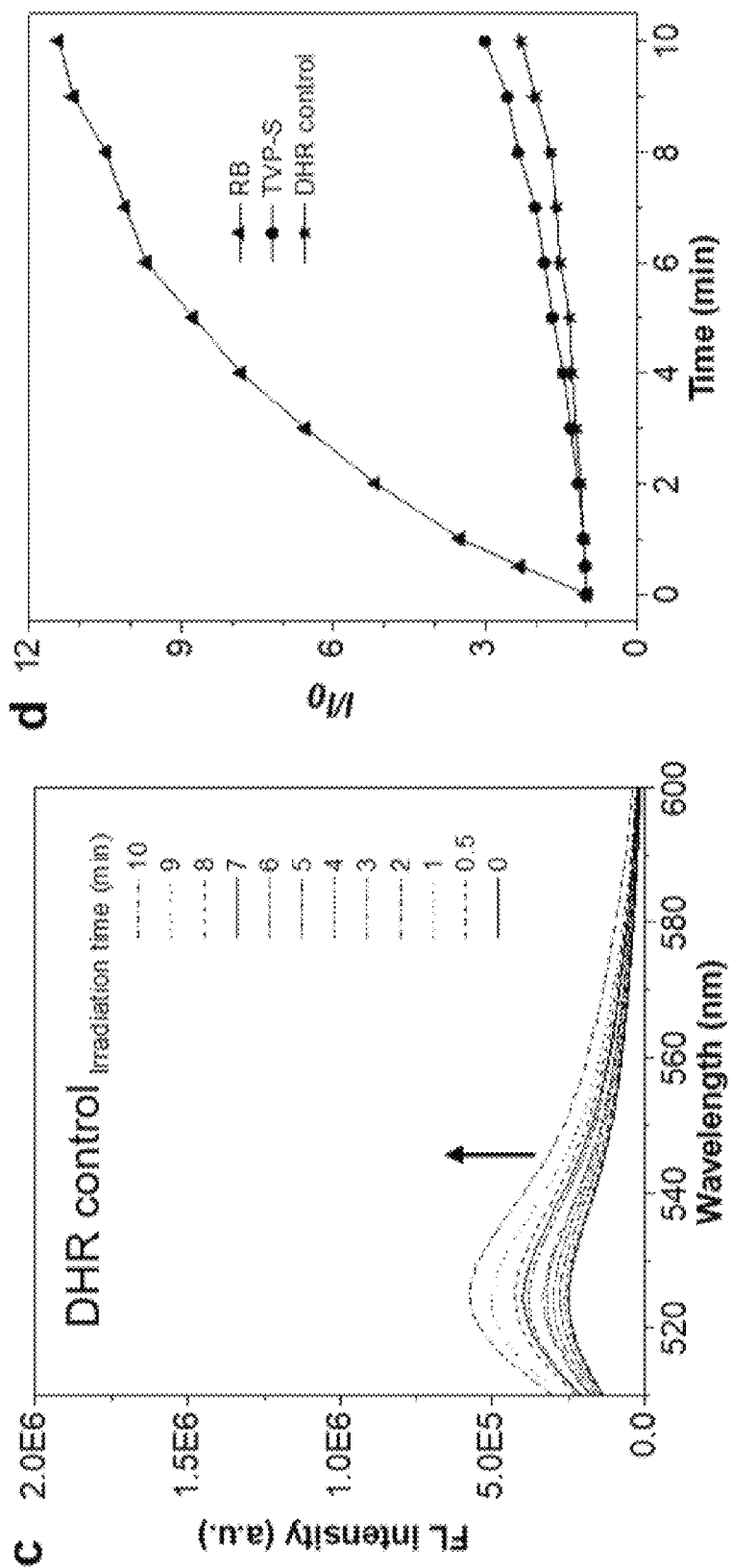
Figure 9:
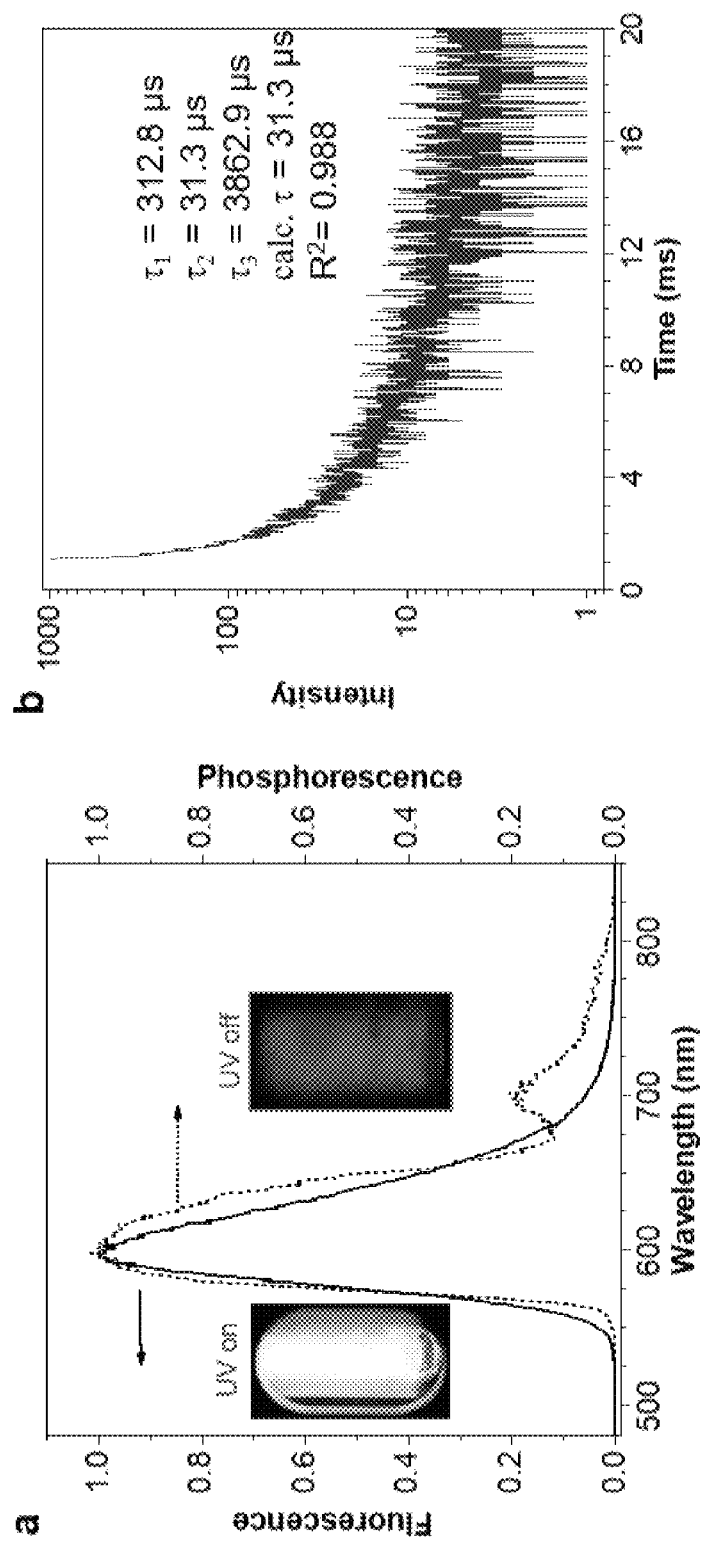
FIG. 9 depicts the triplet state of TVP-S and the singlet oxygen emission measurement. (a) The emission spectra of fluorescence and phosphorescence after delayed by 1 ms under 77 K. The inner pictures were captured under 365 nm UV light on and off, respectively. (b) The decay time of emission at 650 nm with calculated lifetime of 31.3 s.

The strong absorption of TVP-S in the visible light region could lead to the utilization of white light as the source for PDI-based antibacterial application. The ROS generation efficiency of TVP-S was initially determined by using of 2',7'-dichlorofluorescin diacetate (DCFH) as indicator, which could emit fluorescence with a "turn on" process triggered by ROS. As depicted in FIG. 4, DCFH alone was non-emissive and remained almost constant during 10 min white irradiation (~4.2 mW·cm$^{-2}$). In contrast, the emission intensity of DCFH gradually enhanced and reached 23-fold within the same period exposure to white light irradiation in the presence of TVP-S. In addition, up to 72.3% of singlet oxygen ($^1O_2$) quantum yield for TVP-S was determined using 9,10-anthracenediyl-bis(methylene) dimalonic acid (ABDA) as indicator and Rose Bengal (RB) as standard with ~75% quantum yield for $^1O_2$ (FIGS. 2e and 2f and FIG. 5). Sodium azide (NaN$_3$) as a $^1O_2$ quencher was further added to the ABDA solution in the presence of TVP-S. As shown in FIG. 6, the decomposition rate of ABDA slowed down gradually with increase of the concentration of NaN$_3$, and 2.0 mg/mL NaN$_3$ could completely inhibited the decomposition of ABDA, implying $^1O_2$ was indeed generated by TVP-S. Meanwhile, no obvious enhancements could be observed in the signal from hydroxyphenyl fluorescein (HBF) indicator for hydroxyl radical (OH$^{\bullet}$) and dihydrorhodamine (DHR) indicator for superoxide radical (O$_2^{\bullet-}$), indicating the $^1O_2$ accounted for nearly all of the ROS generated by TVP-S (FIGS. 7 and 8). As the $^1O_2$ should be stemmed from the energy transfer process between the triplet oxy-gen and triplet excited-state photosensitizer, we further checked the existence of triplet excitons in TVP-S. As shown in FIG. 9, TVP-S exhibited strong phosphorescence emission with a lifetime of up to 31.3 s at 77 K, clearly demonstrated its efficient intersystem crossing to the triplet excited state. Theoretically, this is also quite rational given TVP-S contain Br atom which usually boost ISC process in organic molecular systems (the well-known heavy atom effect).

Figure 10:
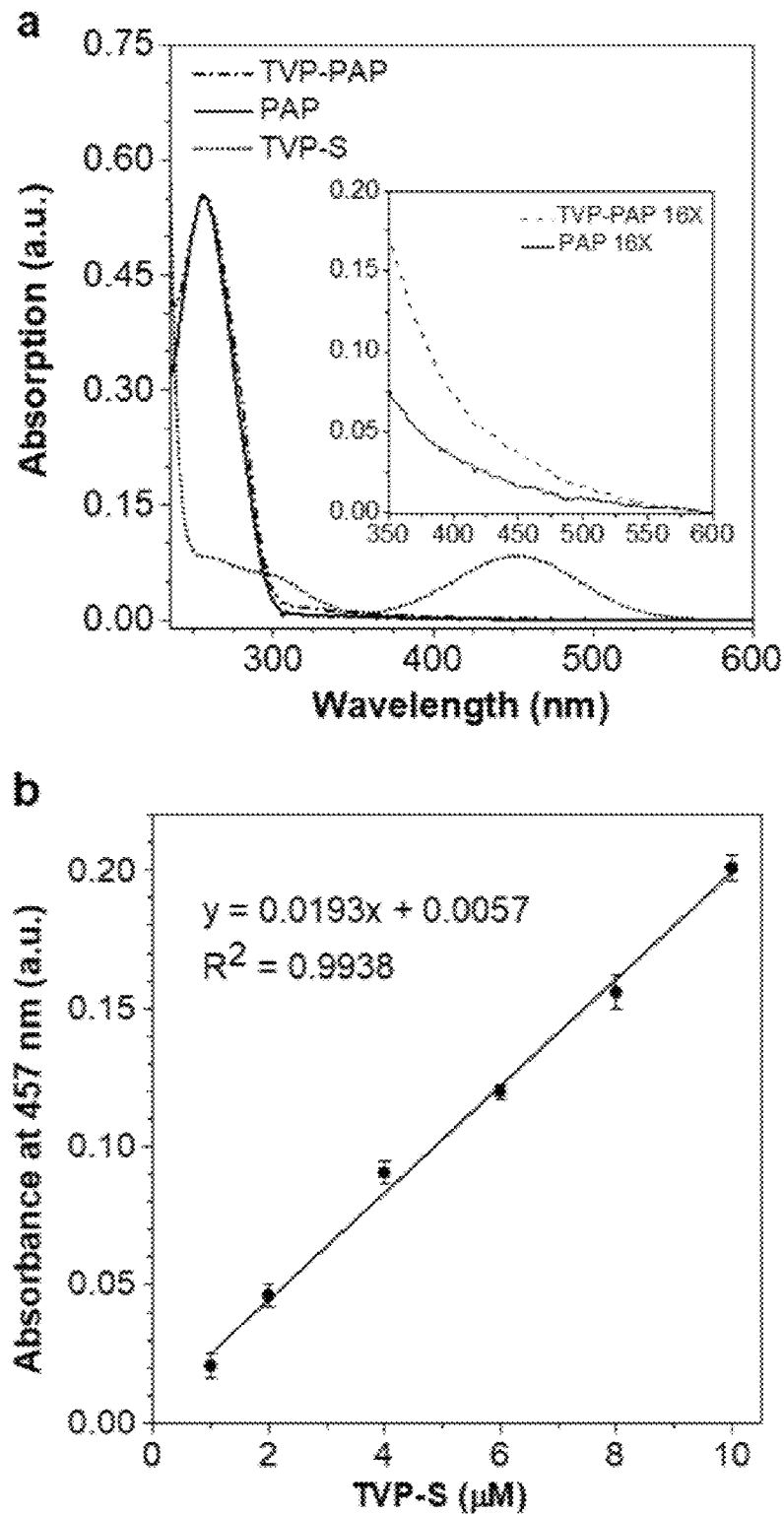
FIG. 10 depicts (a) UV-vis spectra of the aqueous solution of TVP-PAP (9.375×10$^9$ PFU·mL$^{-1}$), PAP (9.375×10$^9$ PFU·mL$^{-1}$) and TVP-S (4.26×10$^{-6}$ mol·L$^{-1}$). The inner plotting was from 16-fold concentrated TVP-PAP (1.5×10$^{11}$ PFU·mL$^{-1}$) and PAP (1.5×10$^{11}$ PFU·mL$^{-1}$). (b) and (c) The standard absorbance curve of TVP-S and PAP, respectively. Abs$_{457\ nm}$ and Abs$_{256\ nm}$ could be fitted linearly with their concentrations. Through subtraction of Abs$_{457\ nm}$ of TVP-PAP by Abs$_{457\ nm}$ of PAP, the concentration of modified AIEgens in the TVP-PAP conjugates could be calculated. And averagely 8200 AIEgens were bound on one PAP entity.
Figure 10:
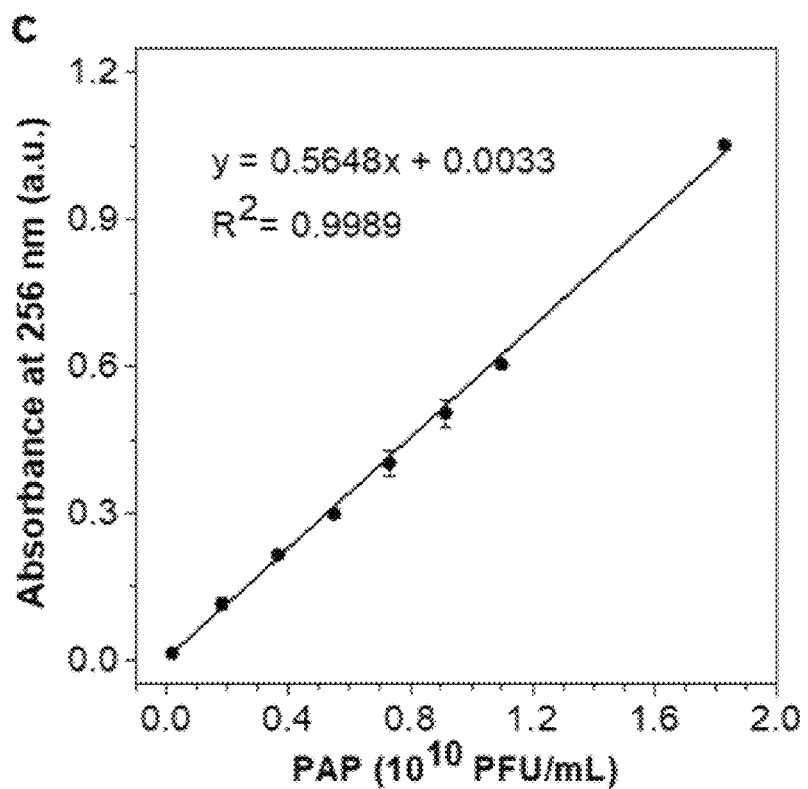
Figure 11:
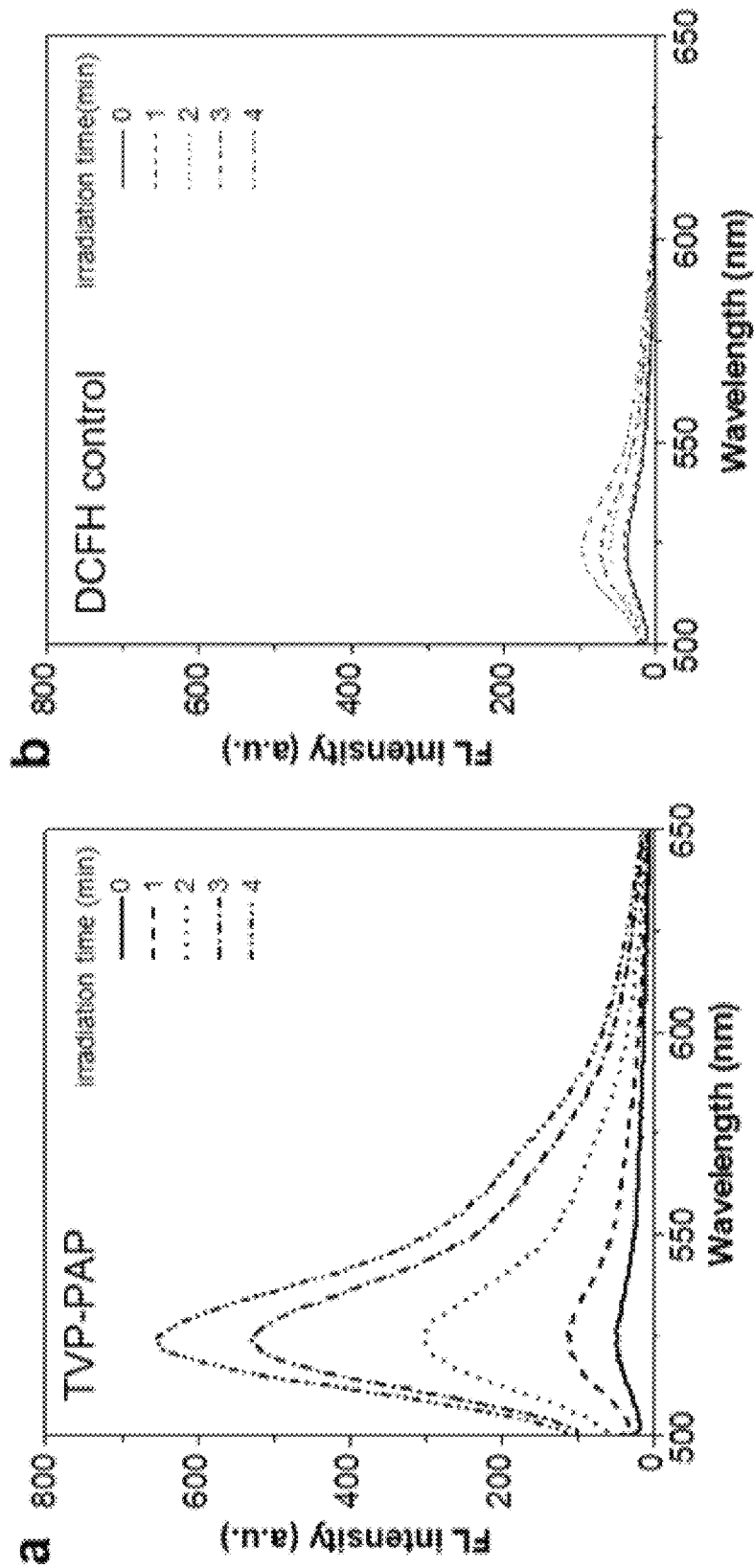
FIG. 11 depicts chemical trapping of total ROS generation bioconjugates. Photoactivation of DCFH with TVP-PAP (a), DCFH control (b), and TVP-S without DCFH indicator (c). These measurements were carried out under white light irradiation in 1×PBS buffer. (d) Activation rates of DCFH with light irradiation under different conditions at 524 nm fluorescence emission.
Figure 11:
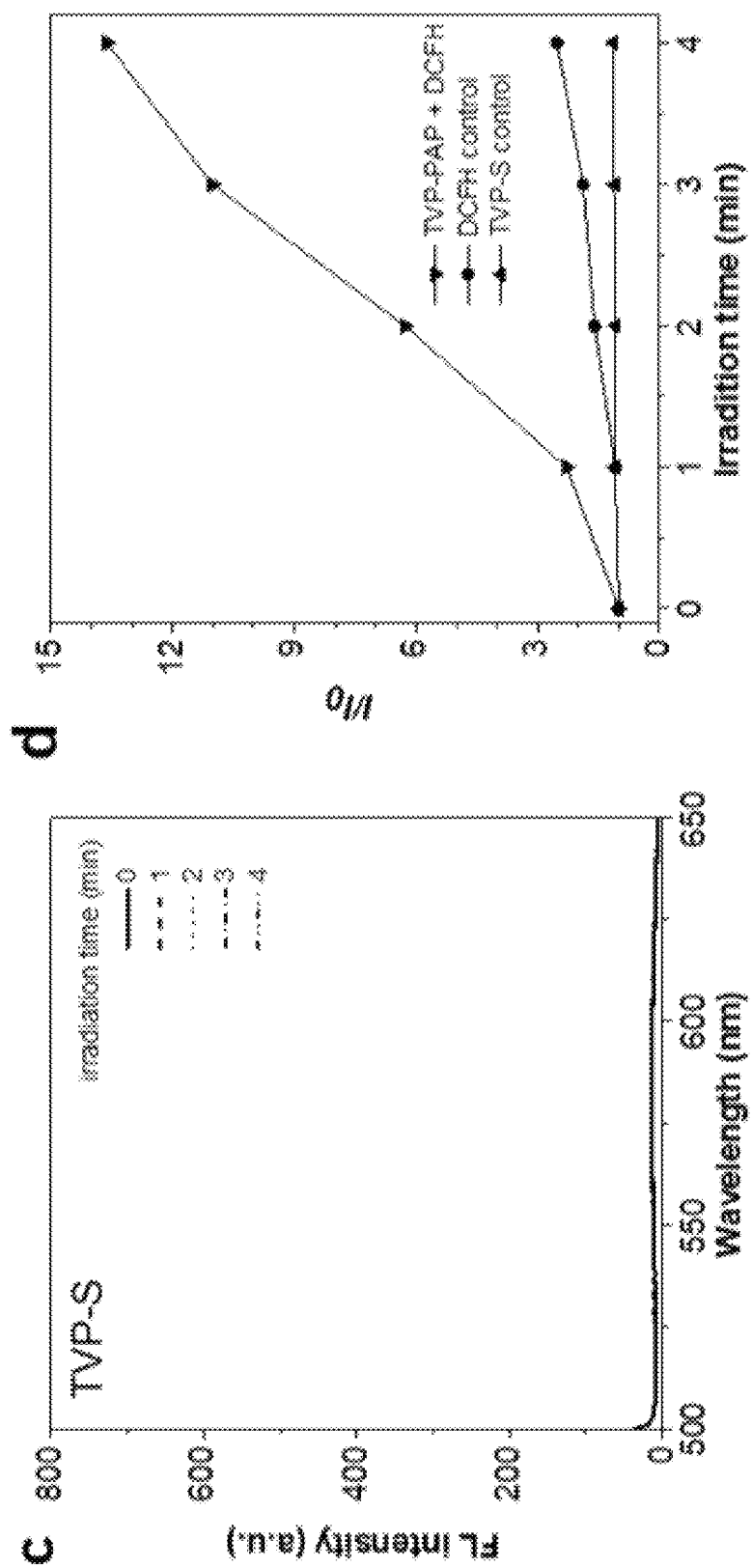

With the activated carboxyl group in its molecular structure, TVP-S could facilely react with the amino group in the outside proteins of bacteriophage and was ready to form the AIE-featured bacteriophage bioconjugate (TVP-PAP). As illustrated in FIG. 10a, the intensified absorbance of PAP bacteriophage in the range of 400-500 nm after AIEgen modification, confirmed the successful bioconjugation reaction be-tween TVP-S and PAP. According to concentration titrations, the molar extinction coefficients of TVP-S and PVP were calculated to be $1.94 \times 10^4$ and $3.41 \times 10^{10}$ M$^{-1}$ cm$^{-1}$, respectively (FIGS. 10b and 10c). And the molar ratio of TVP-S to PAP in the TVP-PAP bioconjugate was determined to be averagely 8200 AIEgen molecules bound on one PAP entity, according to the enhanced absorbance at 457 nm of TVP-PAP comparing to nude PAP. Due to the robust ROS generation capability of prepared AIE-bacteriophage bio-conjugates (FIG. 11), the particular bacterial recognition, real-time tracking, and synergistic bacterial killing were highly expectable.

Particularly Specific Bacteria Imaging by TVP-PAP

Figure 12:
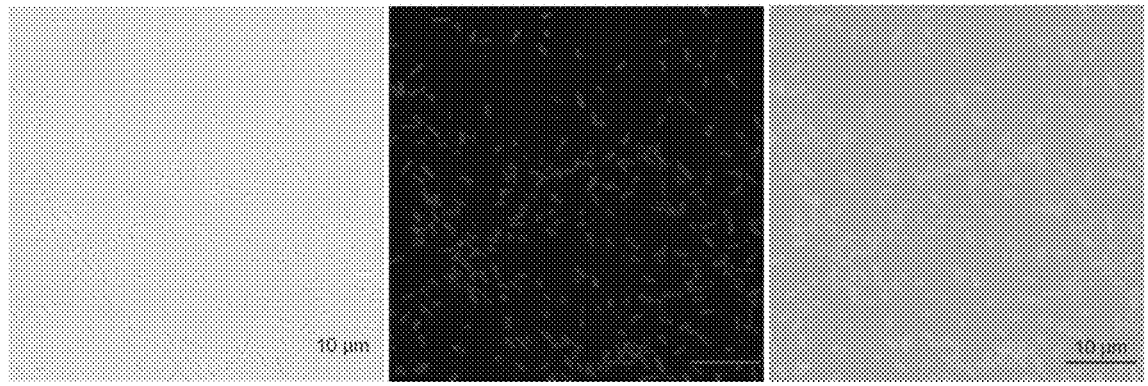
FIG. 12 depicts fluorescence imaging of P. aeruginosa incubated with TVP-PAP for 30 min. All the scale bars were 10 μm. TVP-PAP was excited at 488 nm, and the emission was collected at 580-680 nm.
Figure 13:
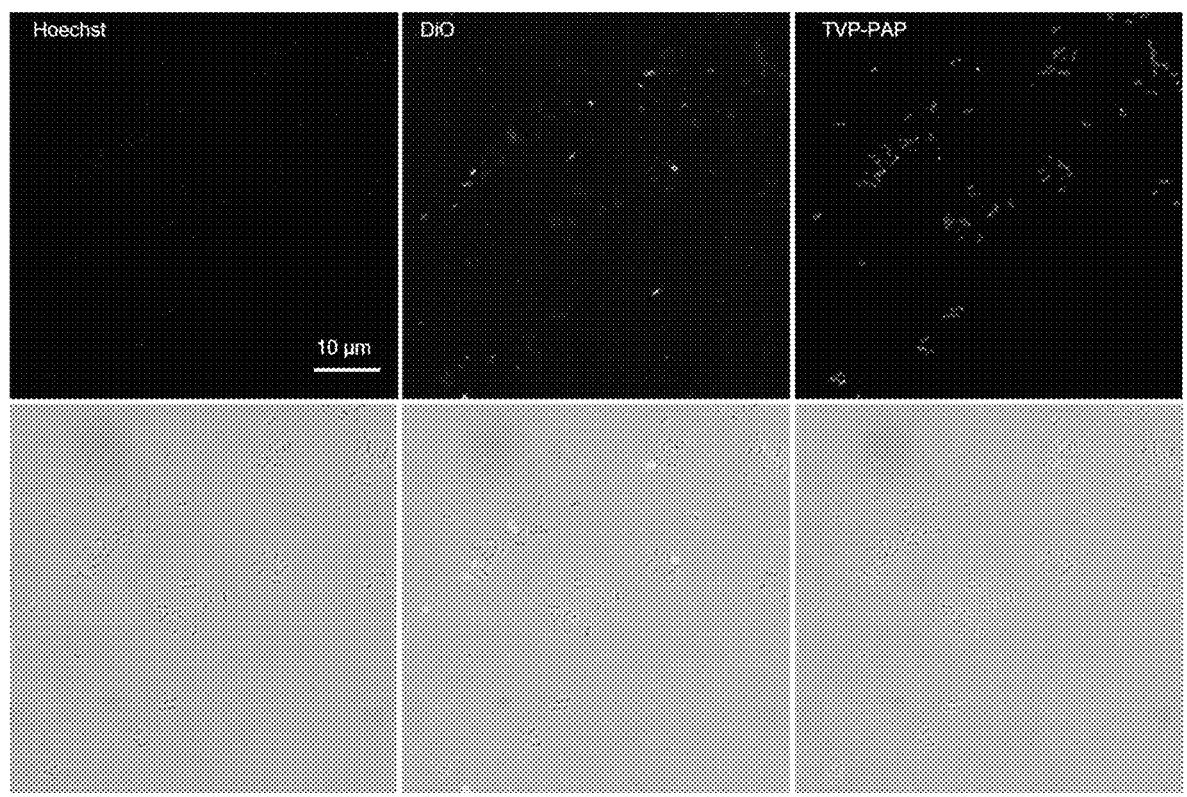
FIG. 13 depicts fluorescence imaging of P. aeruginosa co-incubated with nuclei dye (Hoechst 33342), plasma membrane dye (DiO) and TVP-PAP (AIEgen labelled). Excitations for Hoechst 33342, DiO and TVP-PAP were 350/50, 480/40 and 546/10 nm, respectively; and emissions were collected at 460/50, 527/30 and 585/40 nm, respectively. All scale bars were 10 m.
Figure 14:
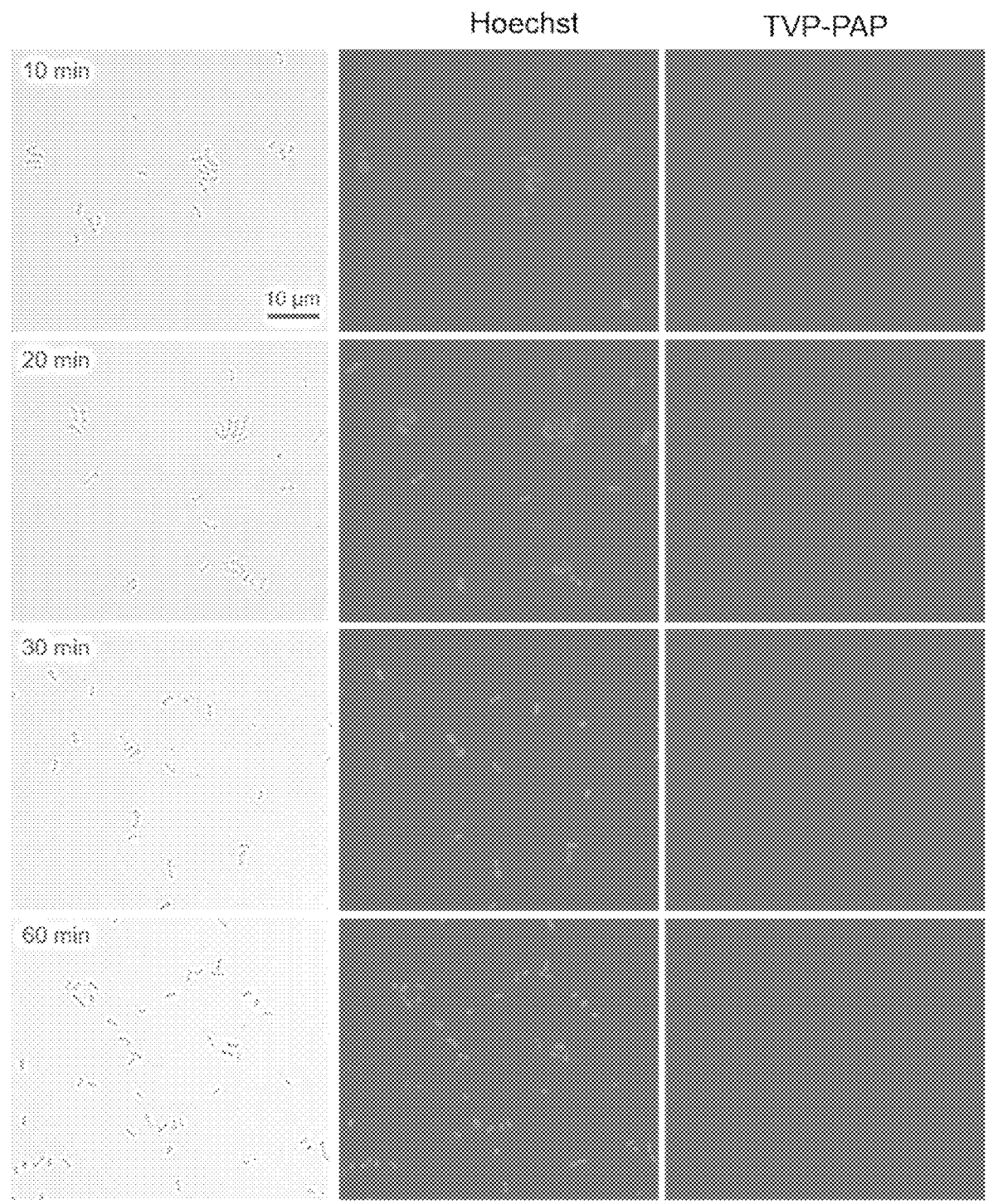
FIG. 14 depicts specificity test of TVP-PAP by fluorescence imaging of A. baumanni incubated with TVP-PAP. Hoechst 33342 with blue color fluorescence was used to stain the nucleus of A. baumannii. Hoechst: Ex: 350/50 nm, Em: 460/50 nm; AIEgen: Ex: 546/10 nm, Em: 585/40 nm.
Figure 15:
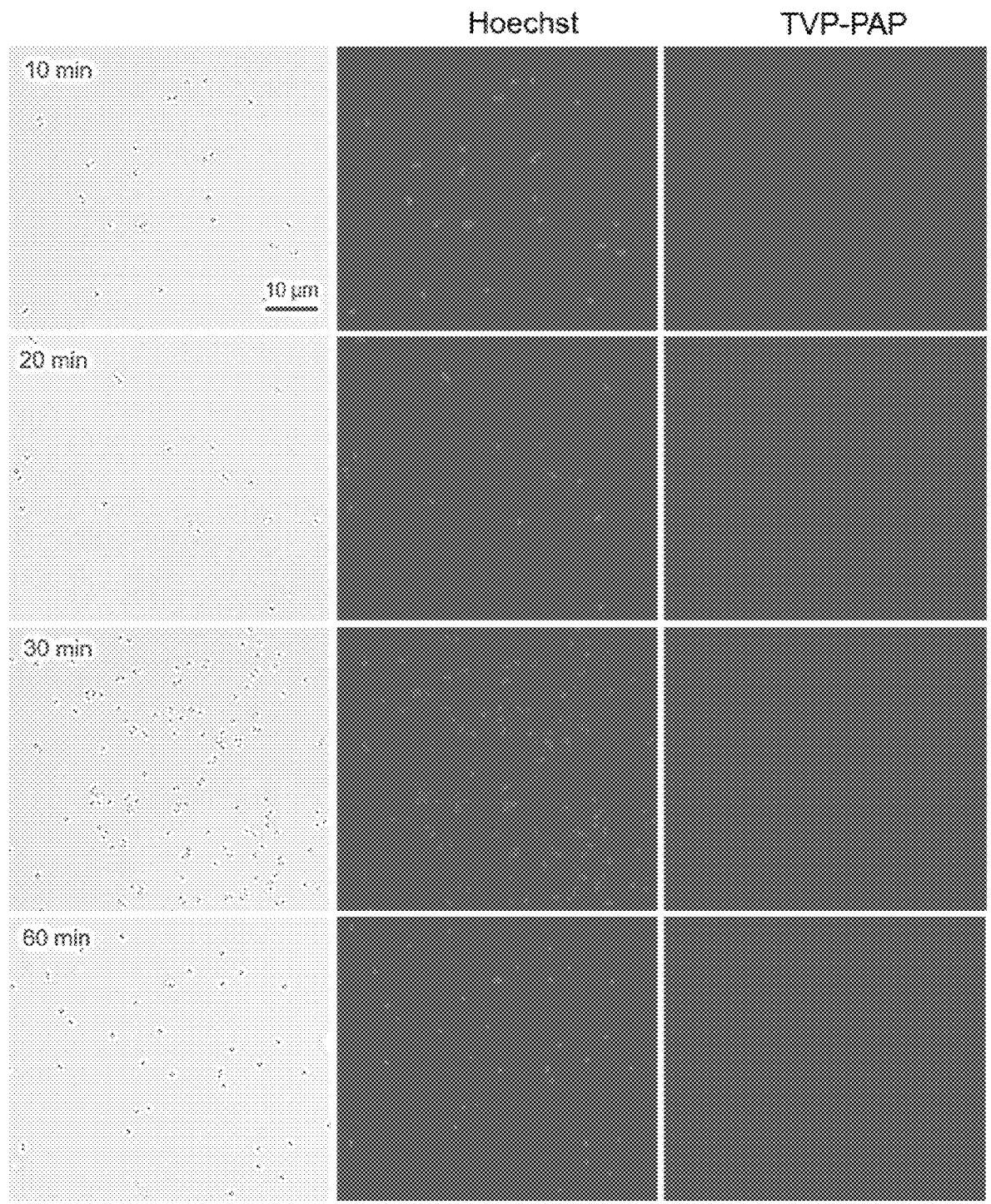
FIG. 15 depicts specificity test of TVP-PAP by fluorescence imaging of S. aureus incubated with TVP-PAP. Hoechst 33342 with blue color fluorescence was used to stain the nucleus of S. aureus. Hoechst: Ex: 405 nm, Em: 420-470 nm; AIEgen: Ex: 488 nm, Em: 550-680 nm.

Taking advantage of the specific recognition feature of bacteriophage and the unique AIE property from TVP-S, the efficiency of bacterial imaging using TVP-PAP was first examined on its target bacteria (*P. aeruginosa*, abbreviated as P.a.). As shown in FIG. 12, *P. aeruginosa* could be stained with bright fluorescence upon incubating with TVP-PAP for 30 min, and the staining efficiency could reach 100% efficiency. Comparing to the commercial cell membrane staining dye, DiO, *P. aeruginosa* could be Light-up stained by the TVP-PAP probe with a much higher staining efficiency (FIG. 13). To test the particular specificity of this TVP-PAP probe stemming from the inherent recognition capability of bacteriophage, we employed two types of bacteria, G$^-$ *A. baumannii* (abbreviated as A. b., FIG. 14) and G$^+$ *S. aureus* (FIG. 15), as control. The results showed that even the process extending to 60 min, neither bacteria could be stained by TVP-PAP probes. And no apparent fluorescence signals emitted out from neither of them in the AIE fluorescence channel.

Figure 16:
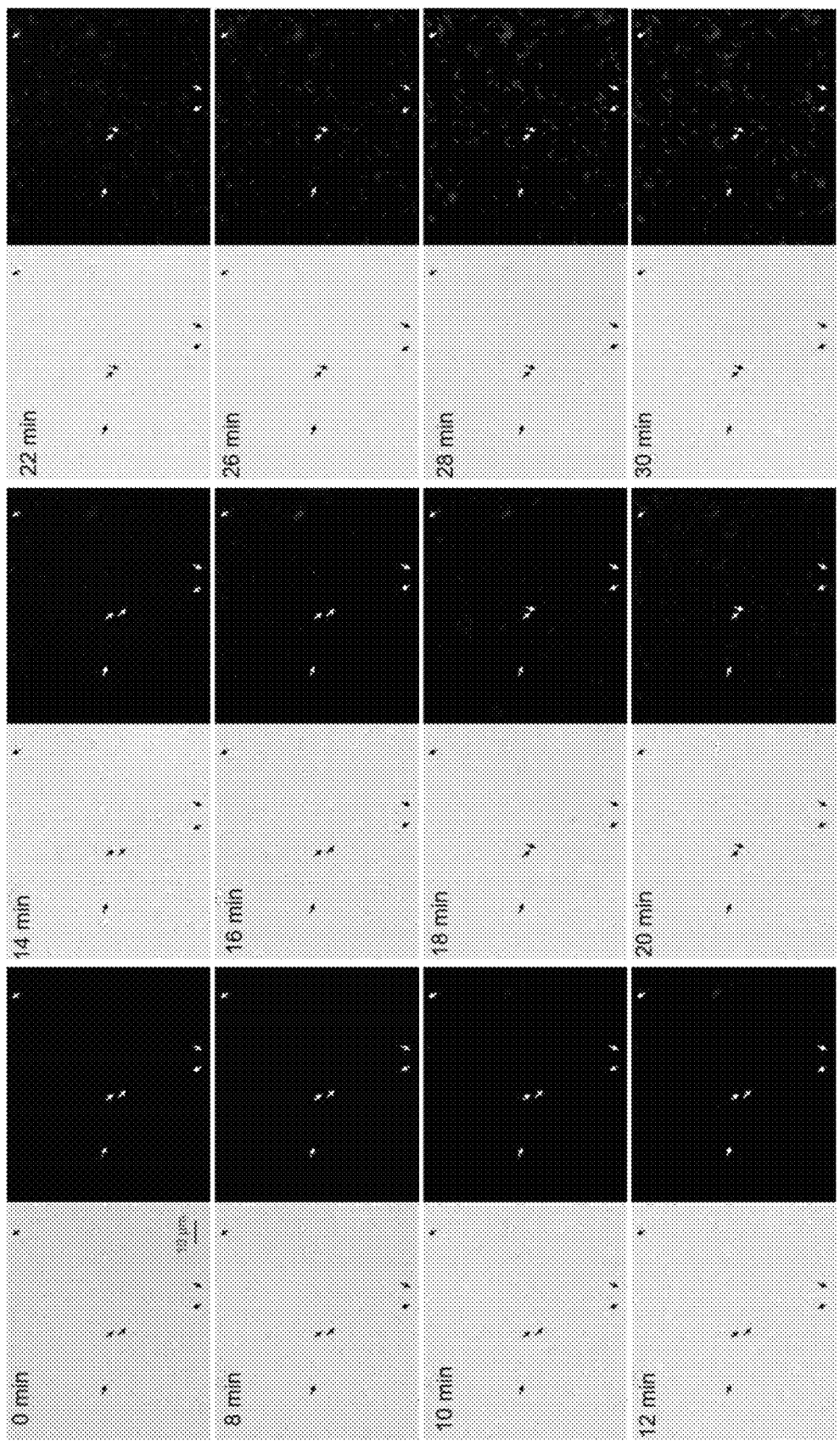
FIG. 16 depicts specificity test of TVP-PAP via co-incubated with P. aeruginosa and A. baumanni under darkness. Arrow indicated A. baumannii without staining by red fluorescence.

Encouraged by this exciting result, we further conducted real-time tracking of the bacterial staining process in the mixed microbes including *A. baumannii* (G$^-$) and host bacteria *P. aeruginosa* (G$^-$) to verify the particular selectivity of the TVP-PAP probe to its target *P. aeruginosa*. Clearly, the *A. baumannii* could never be stained throughout the whole incubation process by monitoring both the bright-field pictures and the fluorescence. In contrast, the recognition and attachment between TVP-PAP and *P. aeruginosa* started after 10 min's coincubation to emit out fluorescence signal. With the time elapsing to 30 min, the fluorescence signal became gradually stronger. And more detailed tracking of TVP-PAP was also carried out, in which the fluorescence signal of bacteria intensified to a platform after 30 min, consistent with the necessary time for bacteriophage targeted binding and infection to the host (FIG. 16). These results of nearly all *P. aeruginosa* being successfully stained while no fluorescence being observed from *A. baumannii*, demonstrated the particular specificity of TVP-PAP probe to its target bacteria. The use of AIEgen alone for bacterial imaging via non-specific electrostatic or hydrophobicity-hydrophily interaction indicated that it is impossible to realize the absolute discrimination of a certain species of bacterium. And the stable and efficient staining of G$^-$ bacteria was always challenged due to the blocking of their complicated cell walls. The introduction of bacteriophage could guide AIEgen to realize discriminative light-up imaging likely equipped with a sensing "radar". And the TVP-PAP carried AIEgen to anchor and aggregate on the surface of target bacteria, resulting in the enrichment of a large number of AIEgens at local site with enhancement in their fluorescence emission for light-up imaging of bacteria. Therefore, significant advancement in targeting specificity could be achieved by TVP-PAP bioconjugate comparing to the previous AIEgens that suffered moderate selectivity.

Figure 17:
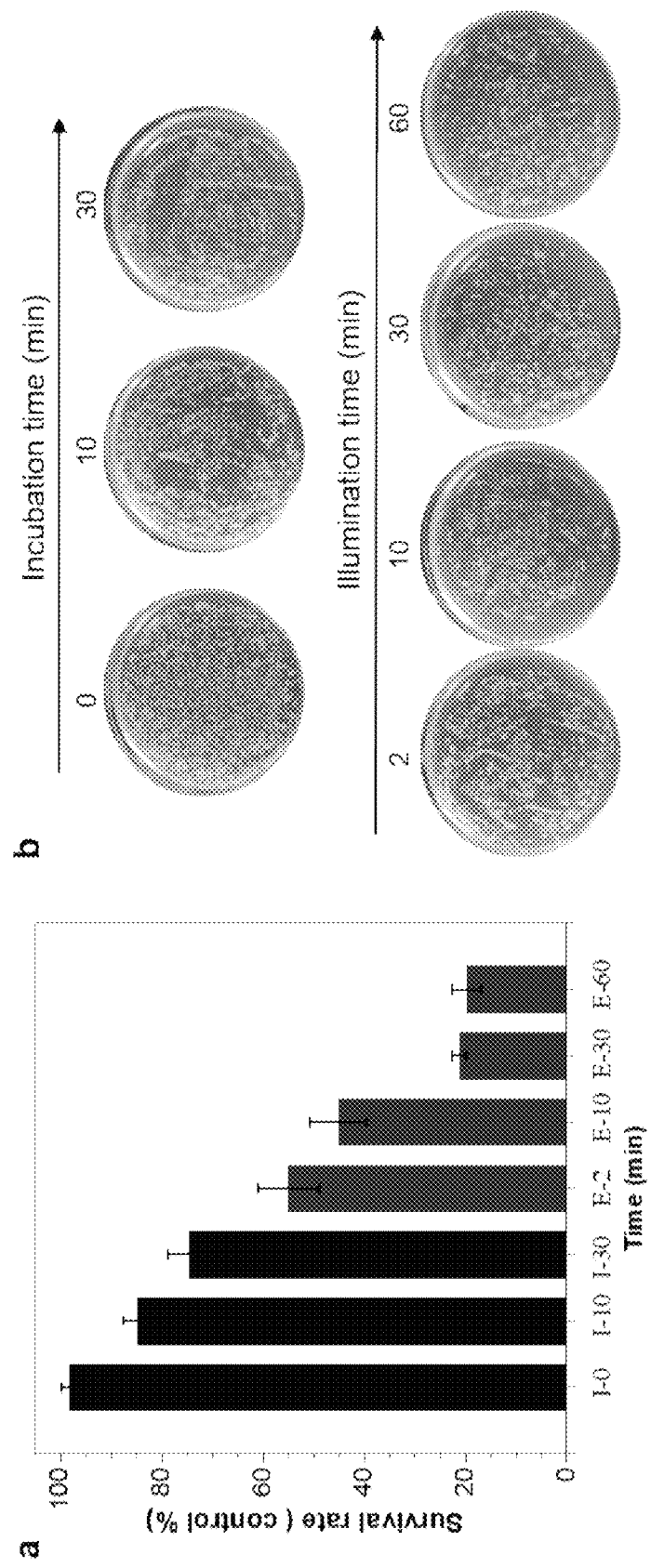
FIG. 17 depicts (a) Bacteria survival rates of P. aeruginosa after treated with TVP-PAP. The bacteria were incubated with TVP-PAP for 0 (I-0), 10 (I-10) and 30 (I-30) min in darkness, the bacteria suspensions were then treated by white-light illumination for 2 (L-2), 10 (L-10), 30 (L-30) and 60 (L-60) min, respectively. (b) Bacterial killing effect of *P. aeruginosa* based on CFU count assay. The control group was without adding of TVP-PAP or illumination.
Figure 18:
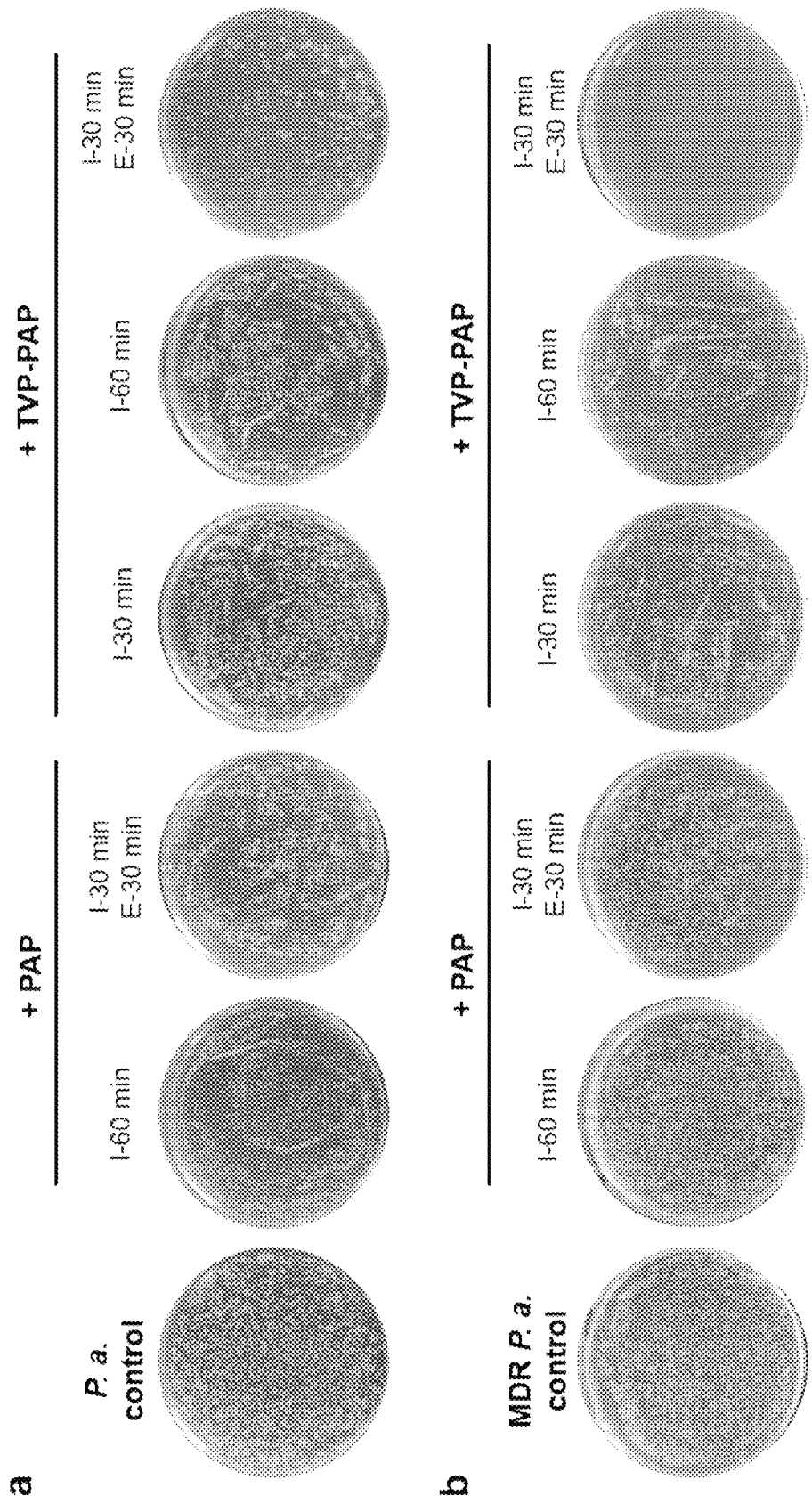
FIG. 18 depicts bacterial killing effect of TVP-PAP to (a) wild-type *P. aeruginosa* and (b) MDR-type *P. aeruginosa* based on CFU count assay, respectively.

Targeted Antibacterial Effect Via Bacteriophage-Guided Photodynamic Inactivation Inspired by the exceptional bacteria-targeting ability of PAP and high $^1O_2$ generation efficiency of AIEgens, we next checked their synergistic antibacterial performances in facing wild-type and clinically isolated multidrug resistant (MDR) *P. aeruginosa*. The times for incubation and white light illumination were first optimized by examining the survival rate of *P. aeruginosa*. In order to avoid the instant decrease of bacterial survival rate, a small amount of TVP-PAP ($9.54 \times 10^5$ PFU·mL$^{-1}$) was added in each group. As shown in FIG. 17, with elongation of the incubation time from 0 to 30 min, the bacterial survival rate decreased from 98.3% to 74.7%, consistent with the saturation time in the above imaging process (FIG. 16). Next, we fixed the incubation time at 30 min and then irradiated the bacterial suspensions by white light (4.2 mW·cm$^{-2}$) for 2, 10, 30, 60 min, respectively. Nearly 79% of *P. aeruginosa* could be eradicated after 30 min's illumination and the efficacy remained unchanged even irradiation prolonged to 60 min, indicating the saturation of ROS generation at this condition. What's more, the bacterial survival rate significantly increased after reversing the sequence of incubation and illumination, suggesting the critical role of bacteriophage targeting and infection before TVP-PAP-guided ROS generation on the bacterial surface (FIG. 18). Thus, light illumination following 30 minutes' coincubation was applied in the subsequent antibacterial tests.

Figure 19:
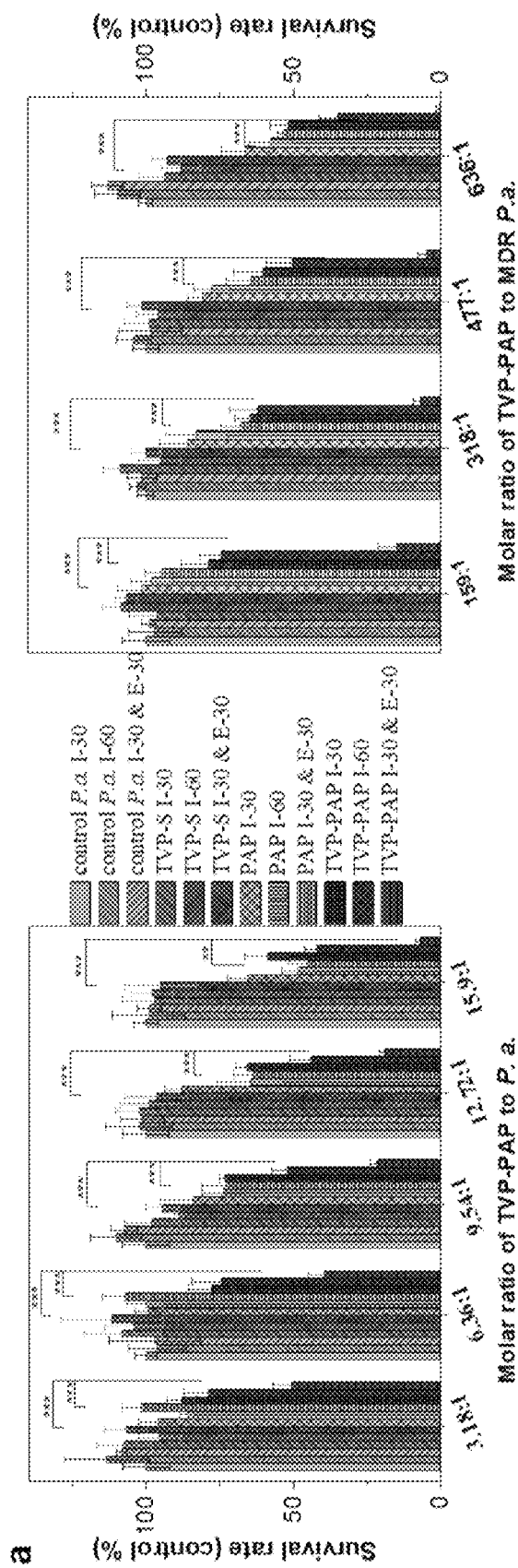
FIG. 19 depicts antibacterial evaluation. (a) Survival rate of wild-type (left) and MDR-type *P. aeruginosa* (right) upon various treatments. (b) *P. aeruginosa* and *A. baumannii* incubated together with TVP-PAP (c) Same concentrations of *P. aeruginosa* and *S. aureus* incubated together with TVP-PAP. Inner pictures in (b) and (c) were the corresponding CFU count assays with I-30 & L-30 treatment. The arrow indicated *P. aeruginosa* identified via colony morphology and colony color for another 36 h incubation (I: incubation; L: light illumination).
Figure 19:
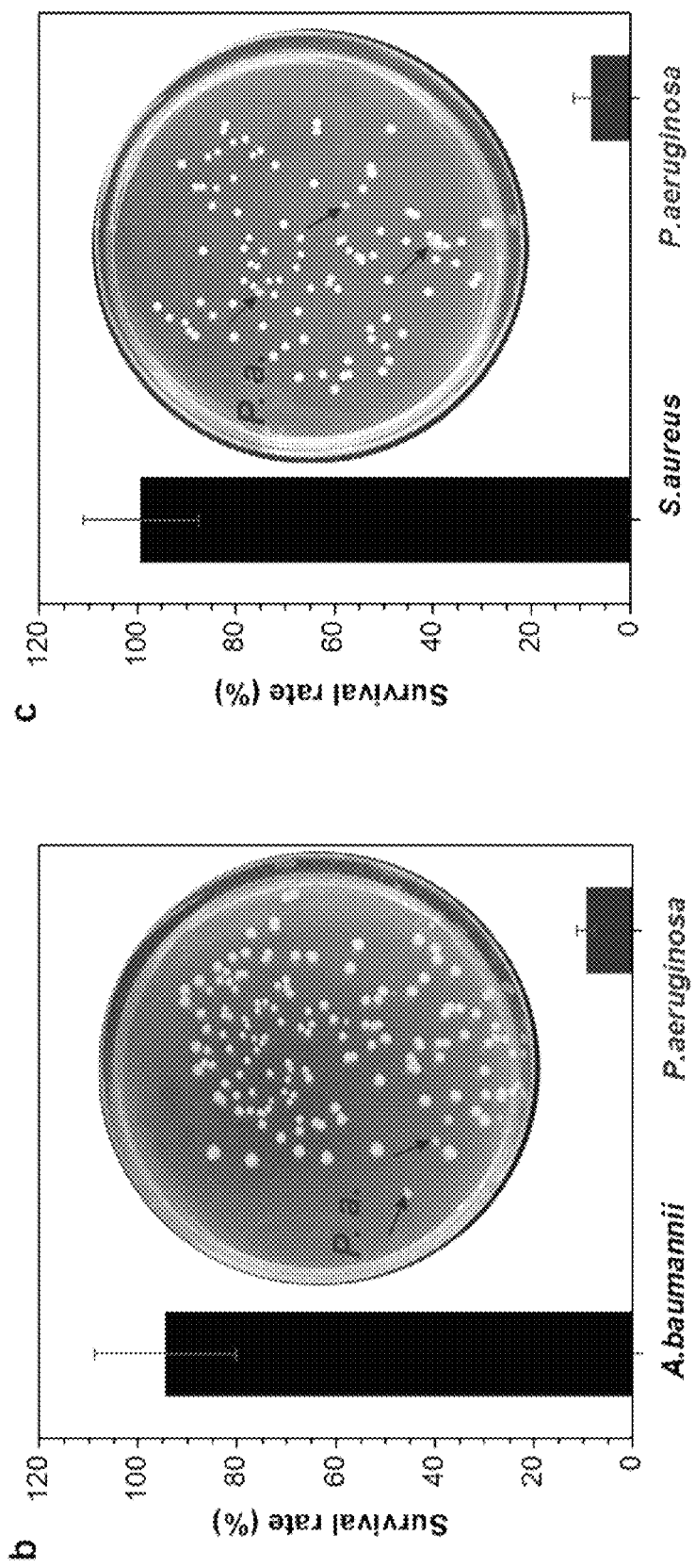
Figure 20:
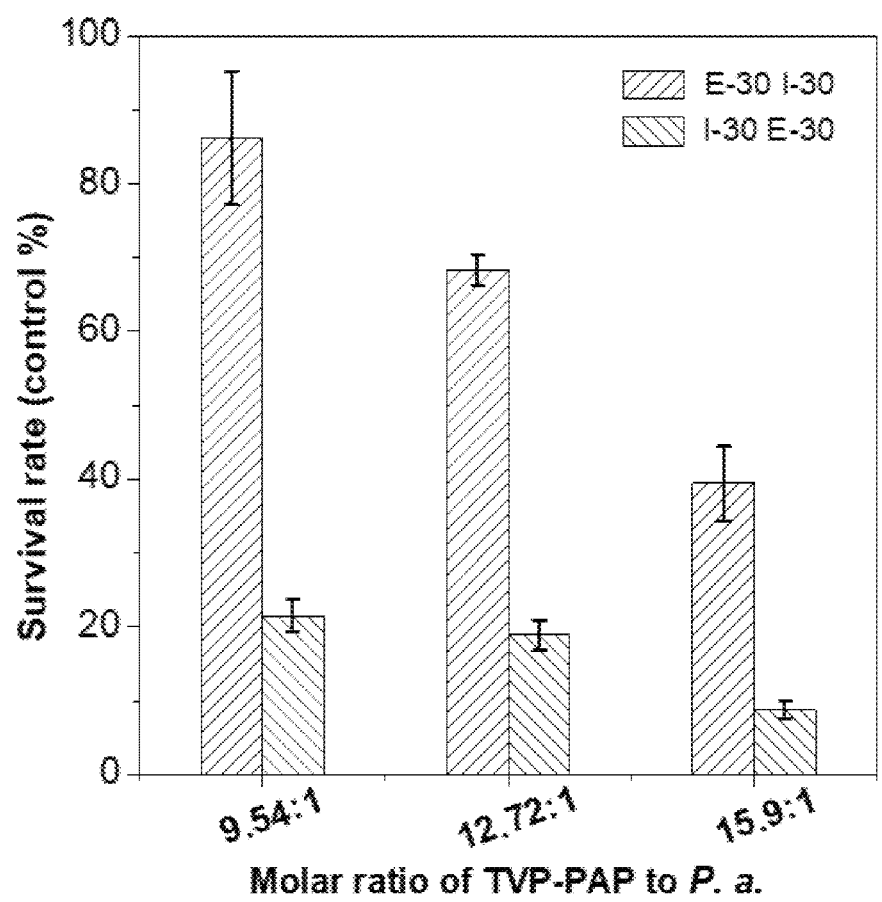
FIG. 20 depicts bacteria survival rates after various treatment sequence.

The synergistic antibacterial effect of TVP-PAP was next tested by comparing with the same molar concentrations of individual AIEgen and PAP entity. As shown in FIG. 19a, for wild P. aeruginosa, neither incubation in darkness (control I-30, control I-60) nor with further white light irradiation (control I-30 & L-30) could pose apparent influence on bacterial survival rate. Similarly, TVP-S alone could neither inhibit the bacterial growth crossing the tested concentration range (4.33~21.65 pM, according to 3.18:1~15.9:1 molar ratio), no matter with or without light irradiation. It was possibly that the non-specific AIEgens and their relative low concentration on the surface of bacteria weakened the destructive effect. In contrast, upon PAP treatment, antibacterial effect initiated when its concentration rising to $9.54 \times 10^5$ PFU·mL$^{-1}$ (according to 9.54:1 molar ratio) under darkness (PAP I-60). And the bacterial survival rate further decreased to 48.3% when the concentration increasing to $15.9 \times 10^5$ PFU·mL$^{-1}$ (according to 15.9:1 molar ratio) with a dose-dependent manner. This result indicated the inherited infection capability of the TVP-PAP bioconjugate from PAP moiety. With assistance from AIEgen, TVP-PAP showed a little bit higher antibacterial efficiency in the darkness comparing to PAP alone (TVP-PAP I-30 vs PAP I-30) crossing the tested concentration range, possibly contributed by the dark toxicity of the AIEgens enriched on the surface of P. aeruginosa. With elongating the interaction time for another 30 min (TVP-PAP I-60), this dark toxicity became much stronger and could cause another 20% decrease in the bacterial survival rate at the concentration of $9.54 \times 10^5$ PFU·mL$^{-1}$. What's more, by harnessing the extra PDI activity under white light irradiation, significant enhancements in the antibacterial efficiency could be observed (TVP-PAP I-30 & L-30). With the concentration of TVP-PAP increasing to $1.59 \times 10^6$ PFU·mL$^{-1}$, the bacteria survival rate rapidly decreased to 6.9%. The cloning plate pictures also verified the excellent antibacterial effect from TVP-PAP bioconjugates which was much superior to TVP-S and PAP alone (FIG. 18). Extending to the clinical isolated MDR P. aeruginosa, a similar dose-dependent antibacterial profile was presented upon TVP-PAP treatment. When the concentration of TVP-PAP rising to $6.36 \times 10^7$ PFU·mL$^{-1}$, the eradication efficiency could reach 64.8% (TVP-PAP I-60). And the efficiency could even rise up to 99.5% under white light irradiation (TVP-PAP I-30 & L-30). In contrast, at the same concentration, the individual AIEgen (TVP-S 130 & L-30) and PAP (PAP 130 & L-30) could only kill 7.0% and 46.5% bacteria, respectively, definitely verified the significantly synergistic antibacterial effect boosted by the PDI activity of AIEgens.

The targeted killing is another critical consideration in antibacterial test. Herein, the character of PAP was introduced for the bacterial discrimination and their following targeted killing. This capability of TVP-PAP was checked in two-component systems by culturing host bacteria, P. aeruginosa (G$^-$), with non-host bacteria, A. baumannii (G$^-$) or S. aureus (G$^+$), respectively. As shown in FIGS. 19b and 19c, in the presence of light irradiation, P. aeruginosa were killed effectively and few colonies formed upon TVP-PAP treatment. Whereas the colony quantity of A. baumannii or S. aureus was nearly unaffected, consistent with the above selective staining result of TVP-PAP to its target. The bacteriophage-guided targeting was proposed to play a critical role in achieving this super antibacterial performance. PAP first specifically recognized the wild or MDR P. aeruginosa through its tail protein binding to lipopolysaccharide of the host bacteria. Then the AIEgens (low to 21.65 pM in $1.59 \times 10^6$ PFU·mL$^{-1}$ TVP-PAP) were enriched on the bacterial surface. Following the infection process of bacteriophage itself, the AIEgens generated efficient $^1O_2$ in situ under white light irradiation could further promote the destruction on the targeted bacteria. Comparing to the previous PDI-based antibacterial tests demanding up to several M of AIEgens, our bacteriophage-guided method showed pretty higher efficacy and would remarkably mitigate the toxic concerns regarding the random interaction of traditional photosensitizers with surrounding biomolecules.

Tracking of the Bacteriophage—Guided Targeting and Killing Process

Figure 21:
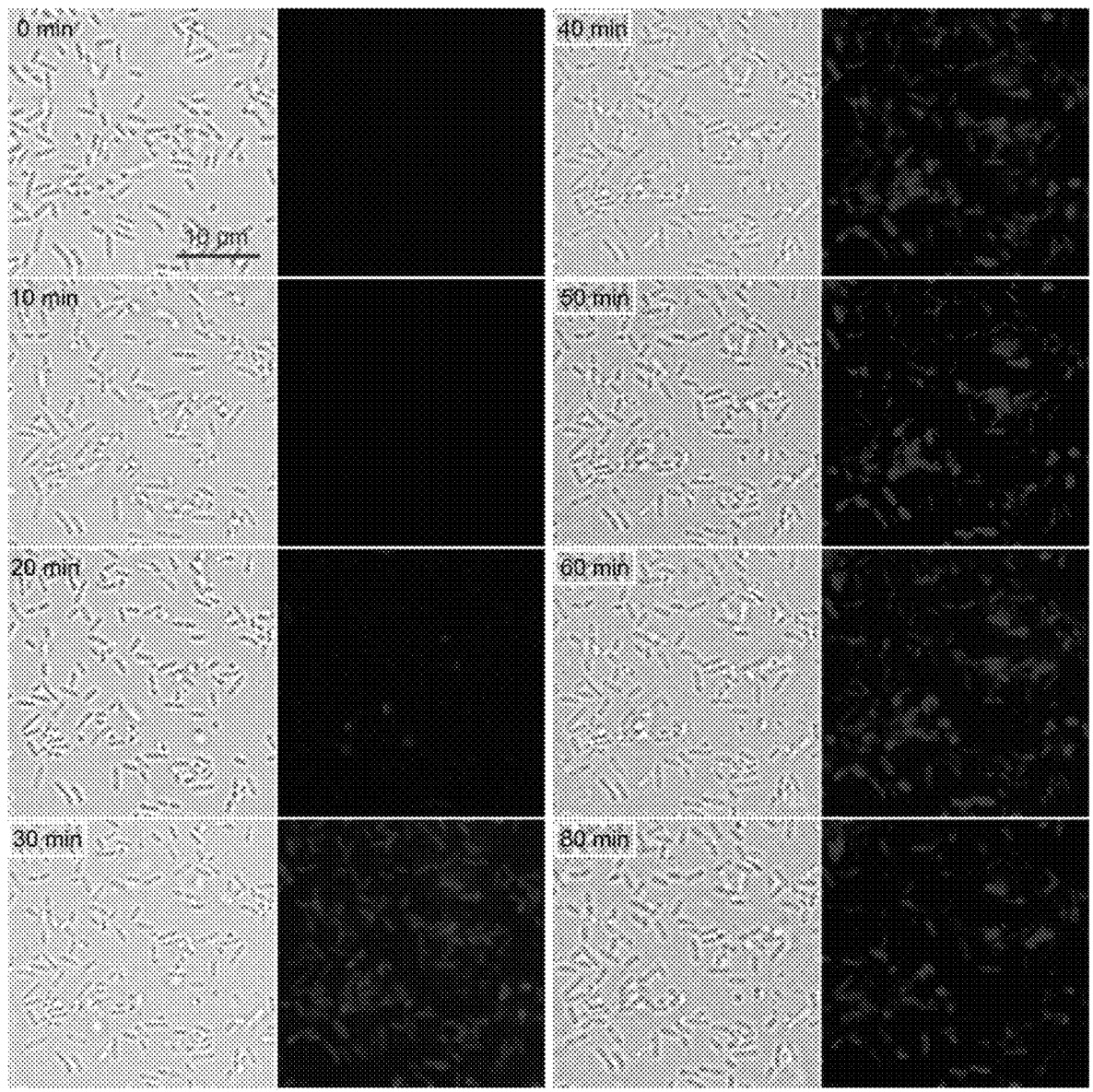
FIG. 21 depicts real-time monitoring of TVP-PAP infecting *P. aeruginosa* and PDI effect. Bacteria were first co-incubated with TVP-PAP for 30 min, and irradiated under white light for another 50 min.
Figure 22:
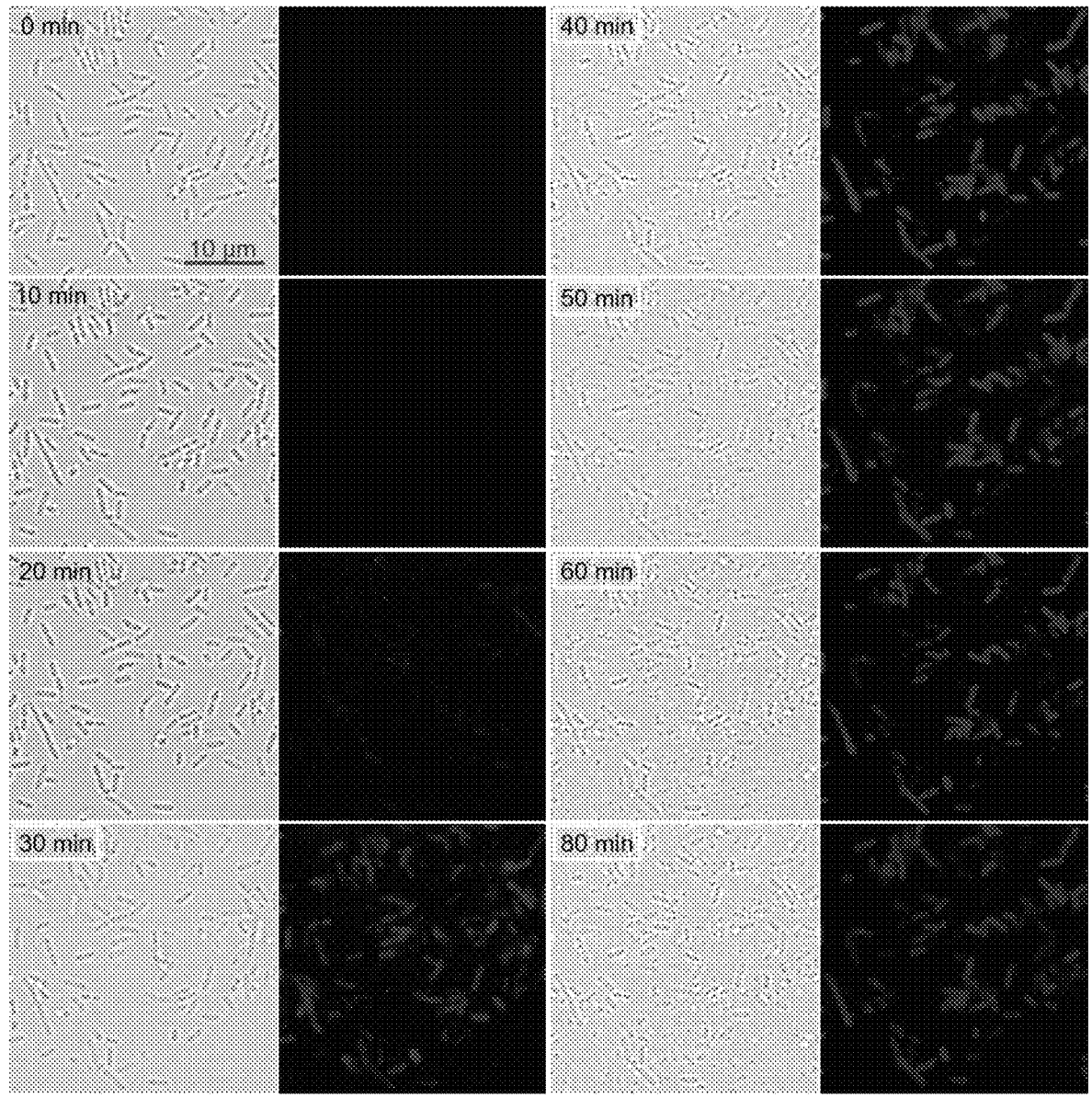
FIG. 22 depicts real-time monitoring of TVP-PAP infecting MDR *P. aeruginosa* and PDI effect. Bacteria were first co-incubated with TVP-PAP for 30 min, and then irradiated under the white light for another 50 min.

The unique fluorescence property of AIEgen was also harnessed for real-time monitoring this targeting and killing process. As shown in FIG. 21, the successful staining of P. aeruginosa was first achieved by incubating with TVP-PAP bioconjugates, with emitting out robust fluorescence signal under imaging. After exposure to white light starting from time point at 30 min, bacterial morphologies became gradually blurred with illumination lasting, with obvious appearance of fragments in the bright field. In the fluorescence field, signals disappeared in a large fraction of bacteria after 10 min's irradiation, along with the apparent agglomeration of bacterial cells. These change in morphology and fluidity indicated destruction happened on the targeted bacteria. To MDR P. aeruginosa, the real-time tracking was performed upon interaction with a higher concentration of TVP-PAP ($6.36 \times 10^7$ PFU·mL$^{-1}$) (FIG. 22). Similarly, after 30 min's coincubation, it was easy to observe the bacterial cell fragment whose amount obviously increased with the elapsing of white light irradiation time, indicating the aggravating damage to the MDR bacteria.

Figure 23:
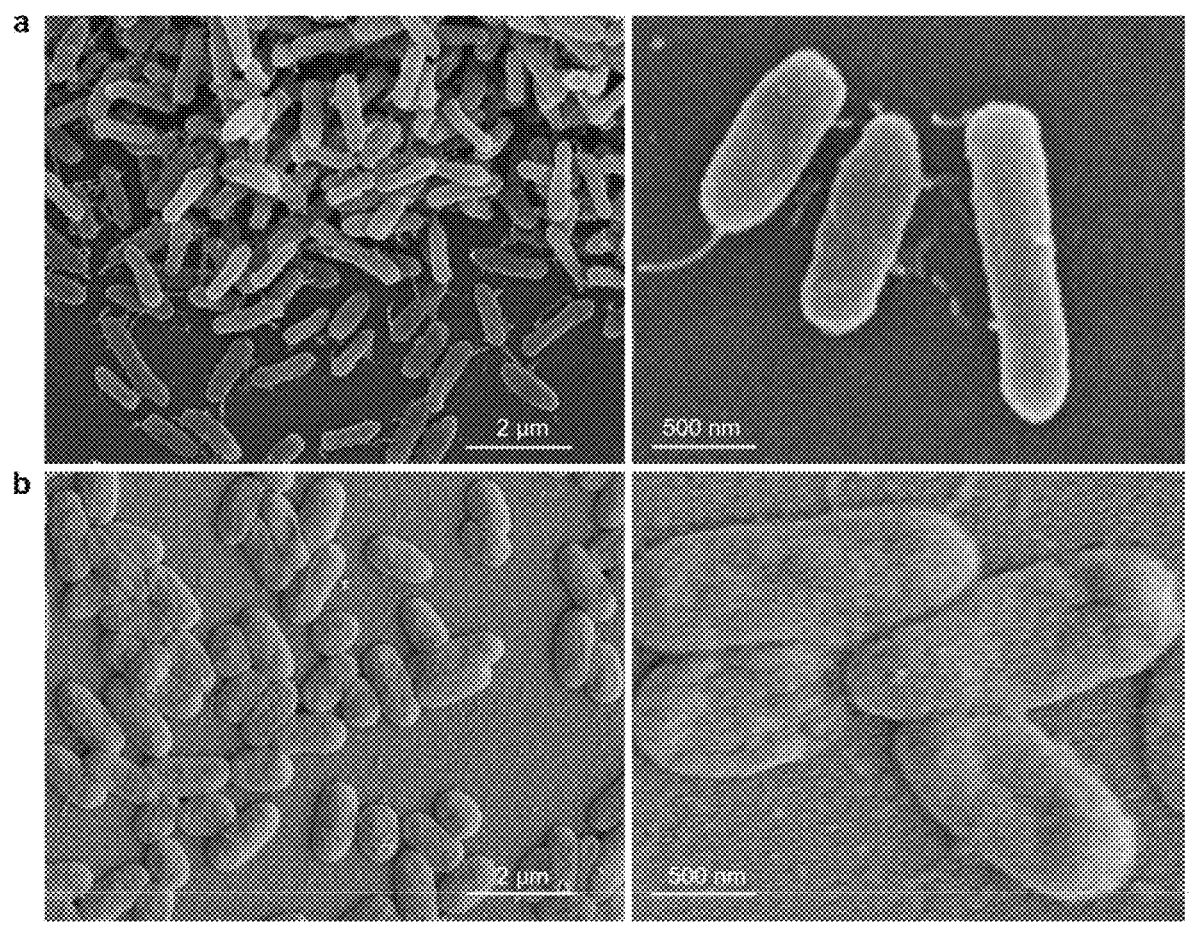
FIG. 23 depicts scanning electron microscopy (SEM) images of bacterial killing effect. (a) *P. aeruginosa* without any treatment. (b) *P. aeruginosa* incubated with TVP-PAP and under white light irradiation.
Figure 24:
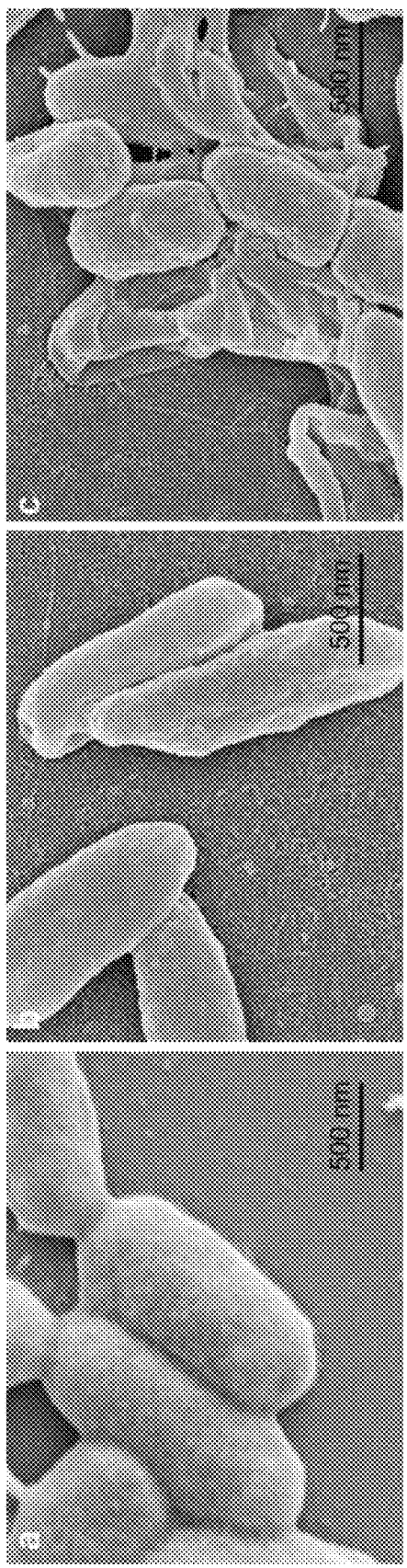
FIG. 24 depicts SEM images of (a) MDR *P. aeruginosa* without any treatment, (b) MDR *P. aeruginosa* incubated with TVP-PAP in darkness and (c) MDR *P. aeruginosa* incubated with TVP-PAP and under white light irradiation.

In order to gain more insights into the antibacterial effect of TVP-PAP, SEM imaging was employed to monitor the morphological changes on wild and MDR P. aeruginosa. As shown in FIG. 23a, without TVP-PAP treatment, P. aeruginosa possessed smooth surface with intact cell wall and well stereo-shape body. In contrast, after treatment with TVP-PAP and white light irradiation, the cell walls of P. aeruginosa apparently became rough and even ruptured with the disappearance of its original stereo shape. Also, numerous holes appeared on the bacterial surface. These holes punched by bacteriophage would accelerate the permeation of $1O_2$ into the bacteria cytoplasm and caused further damages to P. aeruginosa (FIG. 23b). Similar result with coarse cell surfaces and collapsed morphologies, could also be observed in the case of MDR P. aeruginosa, verifying the tremendous destruction from the synergistic effect of TVP-PAP bioconjugates (FIG. 24).

In Vivo Synergistic Eradication of Skin Infections

Figure 25:
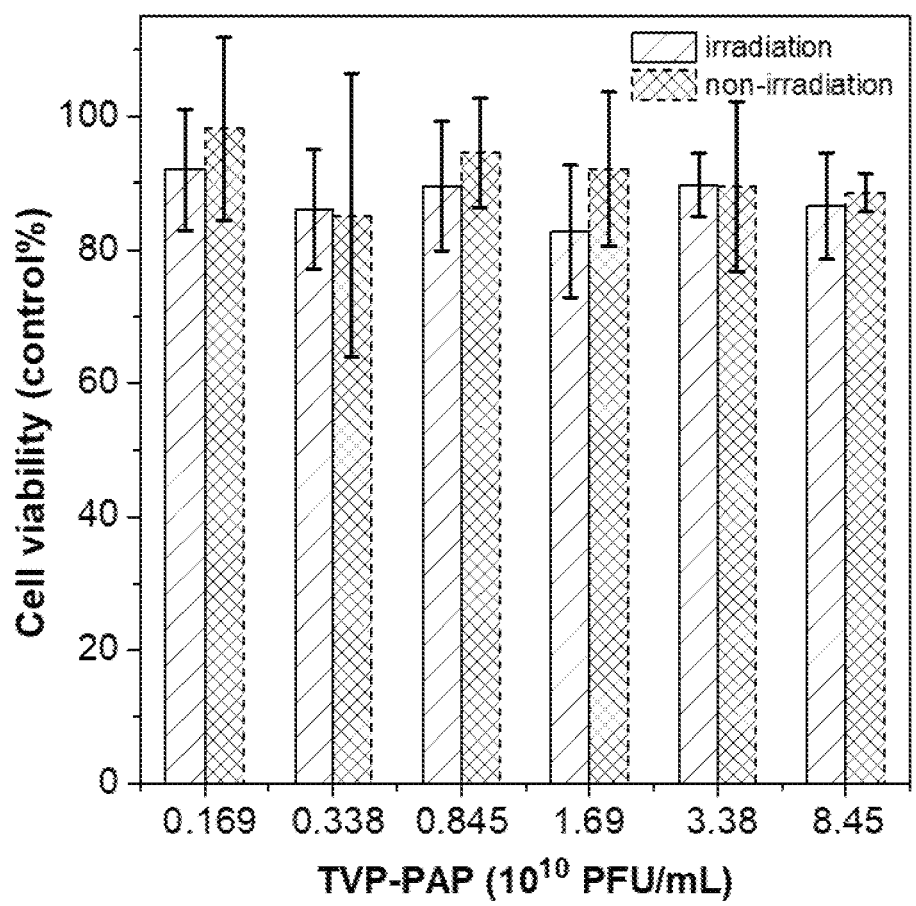
FIG. 25 depicts viability of HaCaT cell after incubation with TVP-PAP at various concentrations for 30 min and then in darkness or upon white-light illumination for 30 min.
Figure 26:
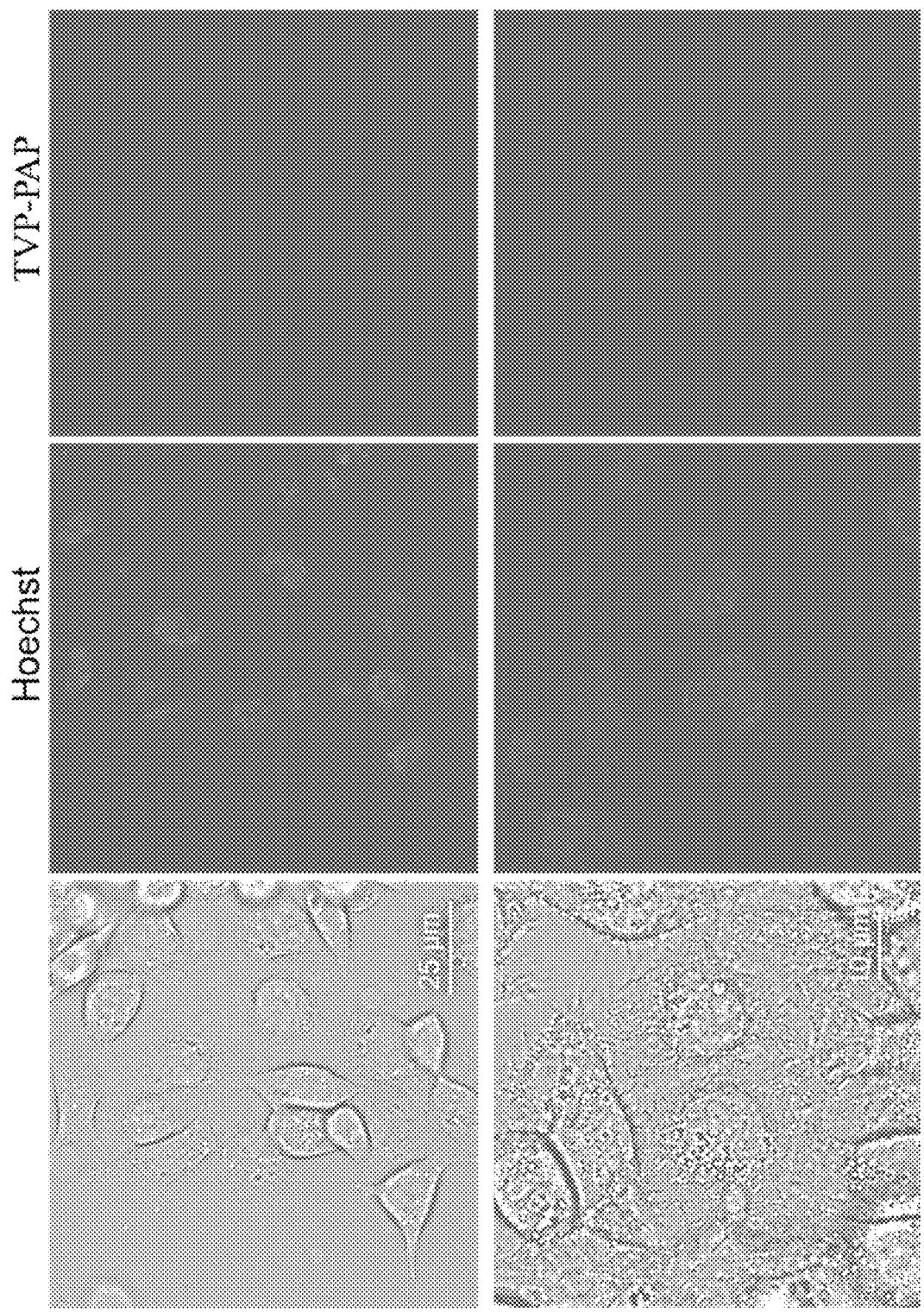
FIG. 26 depicts confocal images of HaCaT cell incubated with TVP-PAP.

Inspired by the outstanding bacteria targeting and elimination activity of TVP-PAP in vitro, we further extended antibacterial examinations to in vivo using a mouse model with wild or MDR P. aeruginosa infectious skin wounds. The biocompatibility of TVP-PAP on normal cells was first checked. As illustrated in FIG. 25, for both dark and illumination groups, the viability of HaCaT cells still remained up to 83% even the TVP-PAP concentration went up to $8.45 \times 10^{10}$ PFU·mL$^{-1}$. The imaging result of HaCaT cell incubated with TVP-PAP further verified its low toxicity as no obvious fluorescence signal could be detected (FIG. 26). And this result indicated the excellent biocompatibility of TVP-PAP and provided a basis for their in vivo antibacterial application.

Figure 27:
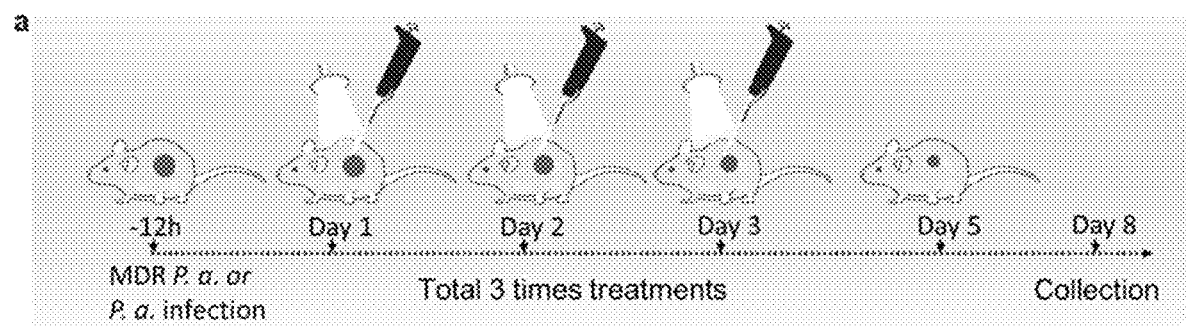
FIG. 27 depicts the in vivo evaluation of TVP-PAP in treatment of wild and MDR *P. aeruginosa* infected wounds on mice. (a) The treatment process illustrated with time elapsing. (b) Photographs of wounds treated by TVP-PAP plus white light irradiation for different time periods. (c) Relative wound size analysis after diverse treatments for 8 days. (d) Photographs of wounds treated by TVP-PAP plus white light irradiation for different time periods. (e) Relative wound size analysis after diverse treatments for 8 days.
Figure 27:
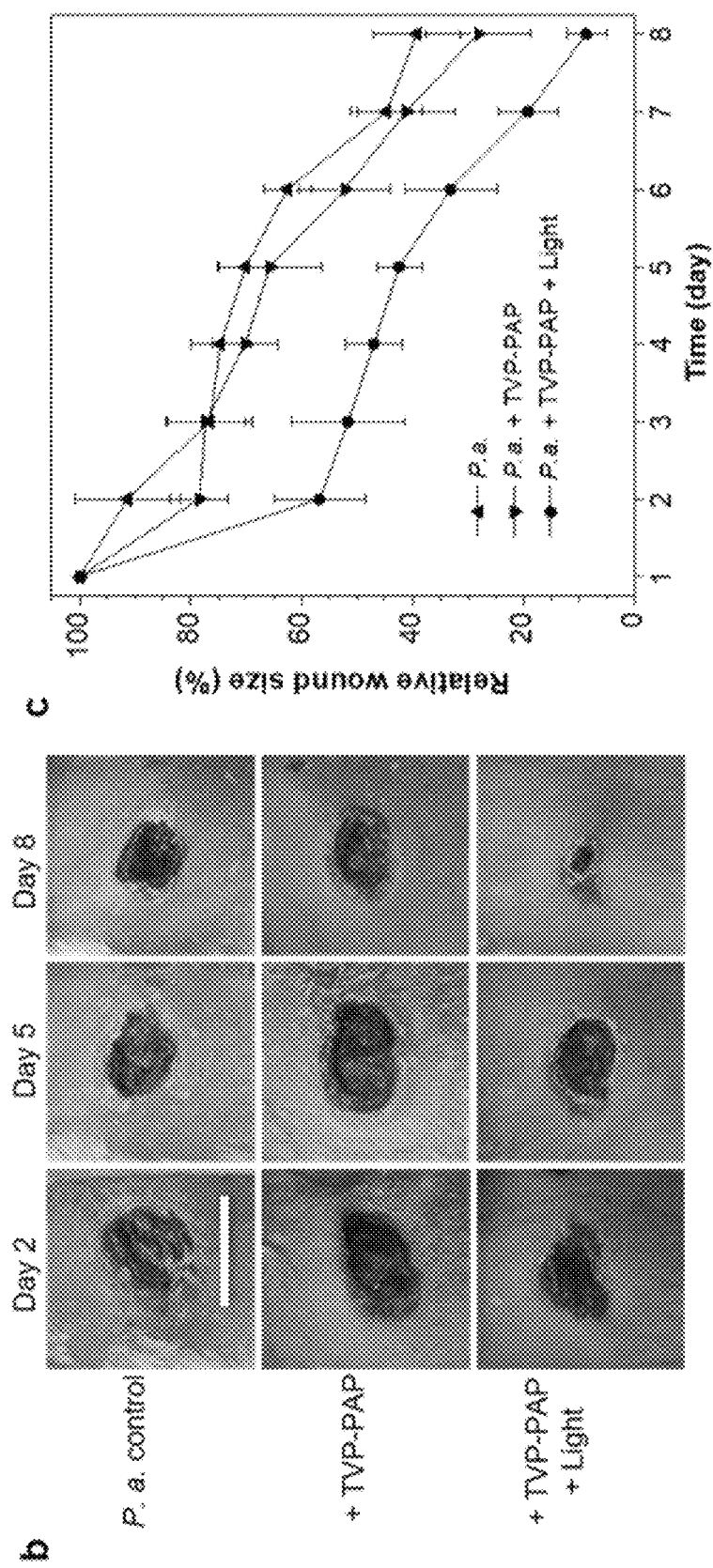
Figure 27:
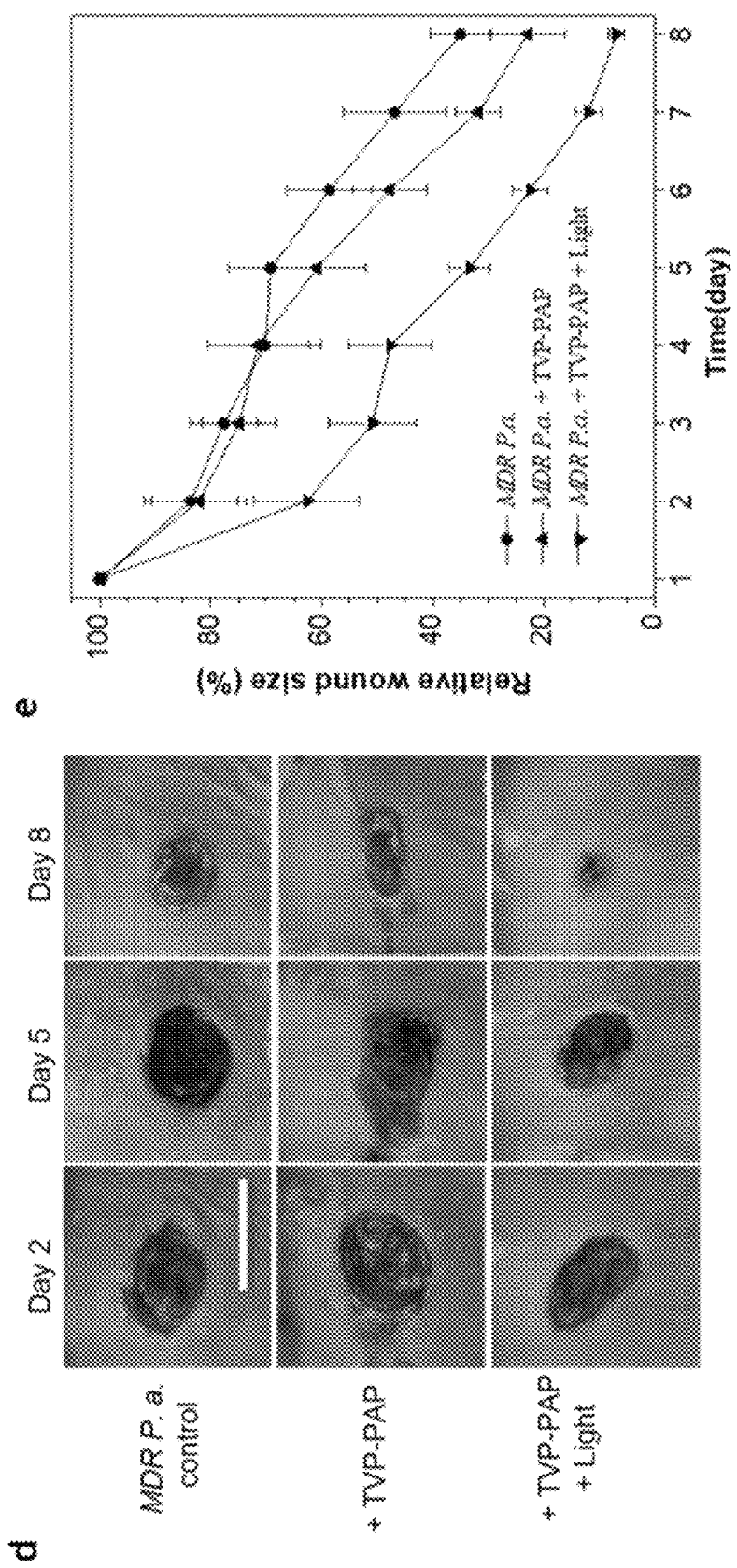
Figure 28:
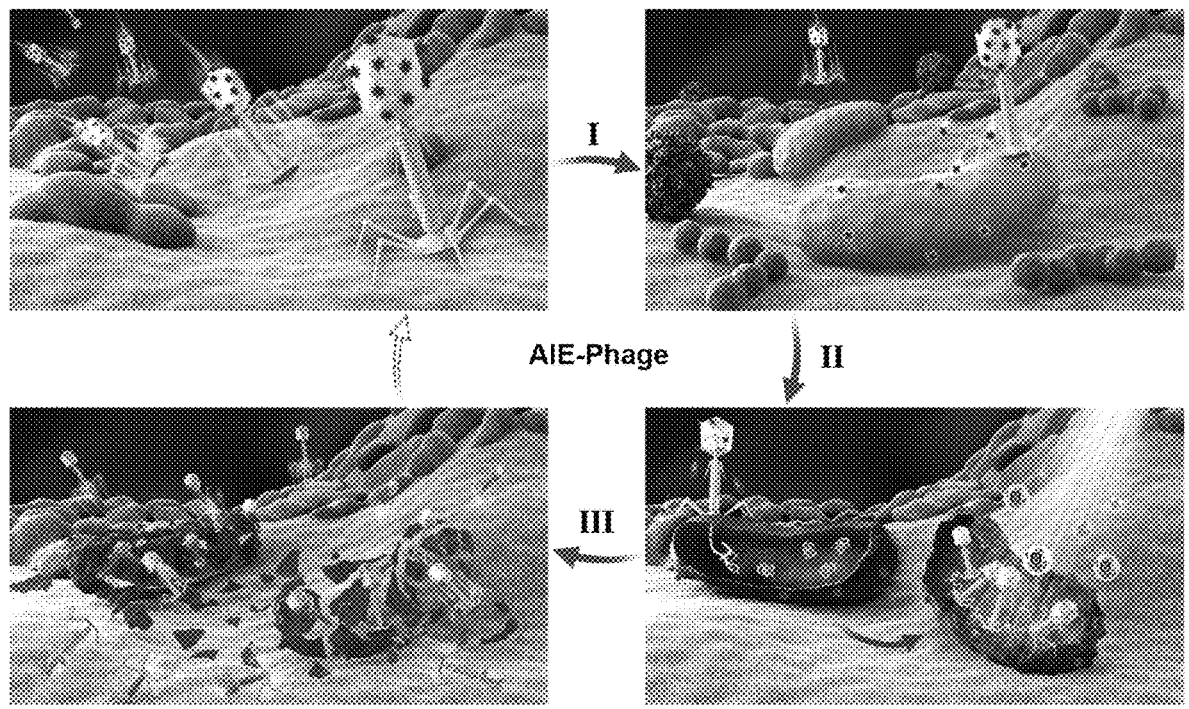
FIG. 28 depicts a schematic showing (I) bacteriophage-guided targeting, (II) discriminative imaging, and (III) synergistic killing of bacteria by AIE-bioconjugates.

After model building, the wild and MDR *P. aeruginosa* infected mice were randomly separated to three groups with various treatments (as depicted in FIG. 27a). Through monitoring the healing processes of the wounds, it was clear that the mice treated with TVP-PAP nearly recovered at 8 day posttreatment (FIGS. 27b and 27d). And both of the relative wound sizes infected by wild and MDR *P. aeruginosa* decreasing to below 10%, significantly smaller comparing to the PBS control or TVP-PAP alone group (FIGS. 27c and 27e). The wound healing was pretty faster than the previous report using AIE polymer and AIEgen-antibiotic conjugate in case of G⁻ bacterial infection, demonstrating the super efficiency of the bacteriophage-guided bacterial killing. Collectively, these outstanding performances in vivo suggested the great potential of TVP-PAP bioconjugates in the application of target bacterial killing and infectious disease therapeutics.

What is claimed is:

1. An aggregation-induced emission (AIE)-bacteriophage bioconjugate comprising a bacteriophage covalently bonded to at least one aggregation-induced emission luminogen (AIEgen) via a linker, wherein the at least one AIEgen has the Formula 4:

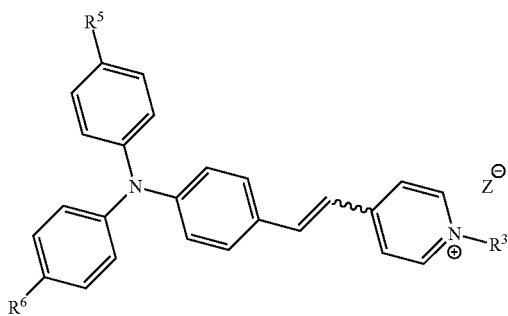

or a pharmaceutically acceptable salt thereof, wherein $R^3$ is the linker represented by the formula: *—$(CR^4_2)_n$-J-**, wherein n is a whole number selected from 1-10; J is —(C=O)—, —NH—, —S—, —N-succinimidyl, or phenol, and $R^4$ for each occurrence is independently selected from the group consisting of hydrogen and alkyl; or two instances of $R^4$ taken together with the carbon or carbons to which they are covalently bonded form a 3-7 membered cycloalkyl, wherein * represents the site of covalent attachment to the AIEgen having, Formula 4; and ** represents the site of covalent attachment of the bacteriophage;

each of $R^5$ and $R^6$ is independently selected front the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;

$R^8$ represents a moiety having the structure:

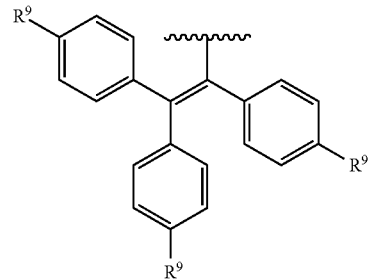

wherein $R^9$ for each instance, is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynl, optionally substituted aryl, optionally substituted aralkyl, heterocycloalkyl, and optionally substituted heteroaryl;

R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; andZ for each occurrence is independently a pharmaceutical acceptable anion.

2. The bioconjugate of claim 1, wherein J is —(C=O).

3. The bioconjugate of claim 1, wherein the bioconjugate comprises between 1,000-20,000 of the at least one AIEgen.

4. The bioconjugate of claim 1, wherein the at least one AIEgen and linker is a moiety selected from the group consisting of:

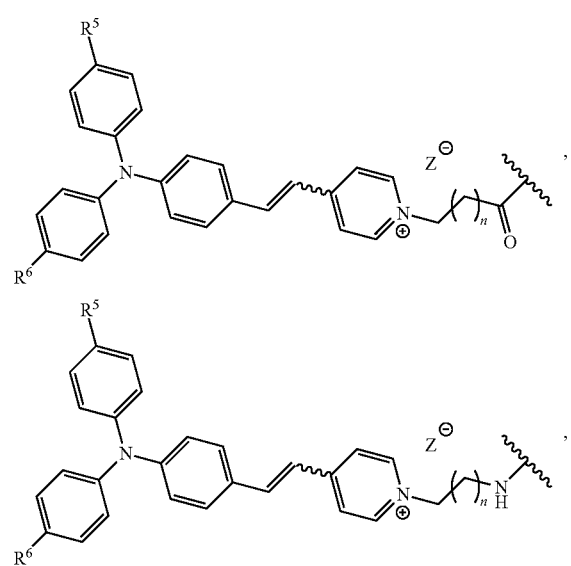

49

-continued

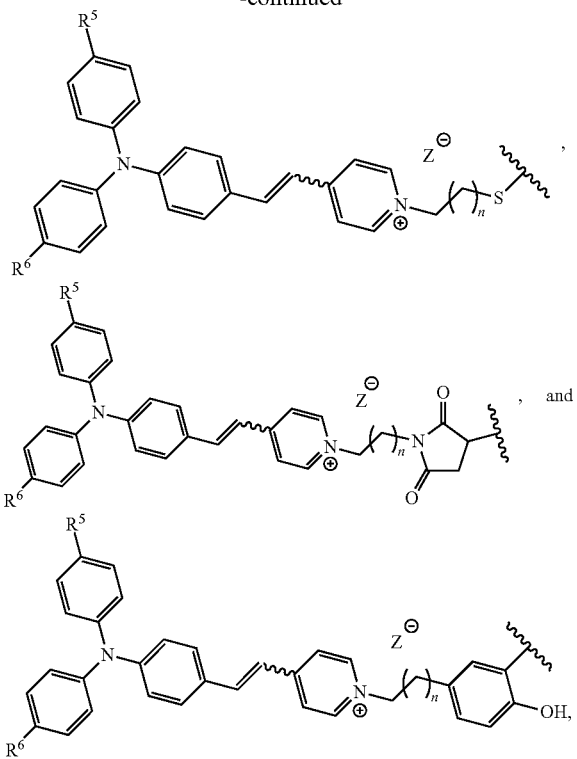

or a pharmaceutically acceptable salt thereof, wherein
n is a whole number selected from 0-4;
each of $R^5$ and $R^6$ is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;
$R^8$ represents a moiety having the structure:

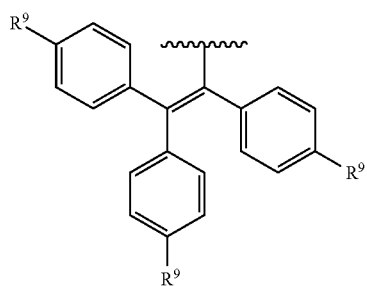

wherein $R^9$ for each instance is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl;
R for each occurrence is independently selected from the group consisting of hydrogen, alkyl, cycloalkyl, alkenyl, alkynyl, optionally substituted aryl, optionally

50 substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and Z for each occurrence is independently a pharmaceutically acceptable anion, wherein represents the site of covalent attachment to the bacteriophage.

5. The bioconjugate of claim 1, wherein the at least one AIEgen and linker is represented by:

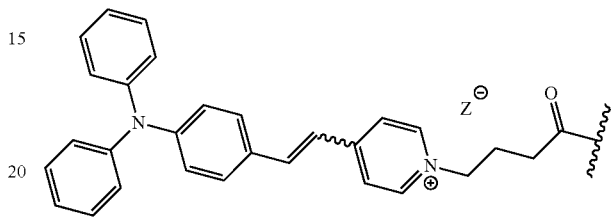

or a pharmaceutically acceptable salt thereof, wherein Z is a pharmaceutically acceptable anion; and represents the site of covalent attachment to the bacteriophage.

6. The bioconjugate of claim 1, wherein the bacteriophage is a filamentous or icosahedral bacteriophage.

7. The bioconjugate of claim 1, wherein the bacteriophage is enterobacteria phage P7 (PAP).

8. A pharmaceutical composition comprising the bioconjugate of claim 1 and at least one pharmaceutically acceptable excipient.

9. A method of preparing the bioconjugate of claim 2, the method comprising:
contacting at least one compound of Formula 5:

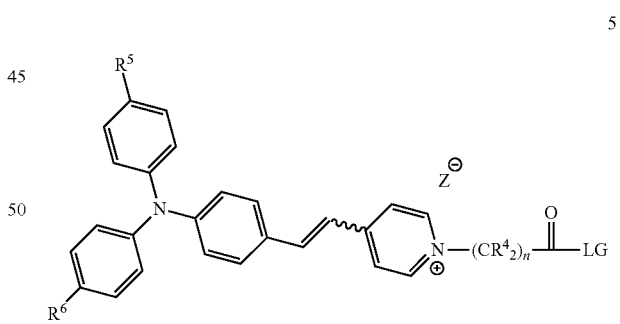

or a pharmaceutically acceptable salt thereof, wherein
n is a whole number selected from 1-10;
LG is a leaving group;
each of $R^5$ and $R^6$ is independently selected from the group consisting of hydrogen, halide, cyano, nitro, —OR, —SR, —N(R)$_2$, —(C═O)R, —(C═O)OR, —(C═O)N(R)$_2$, —N(R)(C═O)R, —O(C═O)R, —N(R)(C═O)OR, —O(C═O)N(R)$_2$, —SO$_2$R, —SO$_2$N(R)$_2$, alkyl, cycloalkyl, alkenyl, alkynyl, aryl, aralkyl, heterocycloalkyl, heteroaryl, and $R^8$;

$R^8$ represents a moiety having the structure:

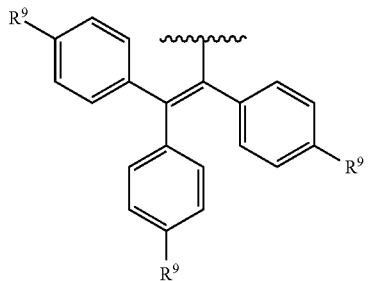

wherein $R^9$ for each instance is independently selected from the group consisting of hydrogen, halide, cyano, nitro, —OR, —SR, —N(R)$_2$, —(C=O)R, —(C=O)OR, —(C=O)N(R)$_2$, —N(R)(C=O)R, —O(C=O)R, —N(R)(C=O)OR, —O(C=O)N(R)$_2$, —SO$_2$R, —SO$_2$N(R)$_2$, alkyl, cycloalkyl, alkenyl, alkynyl, optionally substituted aryl, optionally substituted aralkyl, heterocycloalkyl, and optionally substituted heteroaryl;

R for each occurrence is independently selected from the group consisting of hydrogen, alkyl, cycloalkyl, alkenyl, alkynyl, optionally substituted aryl, optionally substituted aralkyl, heterocycloalkyl, and optionally substituted heteroaryl; or two instances of R taken together with the atom or atoms to which they are covalently bonded form a 3-7 membered cycloalkyl or 3-7 membered heterocycloalkyl; and Z for each occurrence is independently a pharmaceutically acceptable anion;

with a bacteriophage thereby covalently bonding the at least one compound of Formula 5 to the bacteriophage and forming the bioconjugate of claim 2.

10. A method of treating a bacterial infection in a subject in need thereof, the method comprising administering a therapeutically effective amount of a bioconjugate of claim 1 to the subject and irradiating the site of the bacterial infection with electromagnetic radiation in the presence of oxygen.

11. A method of imaging a bacterial cell, the method comprising contacting a bioconjugate of claim 1 with the bacterial cell; irradiating the bacterial cell with electromagnetic radiation; and detecting luminesence from the bioconjugate.

* * * * *

UNITED STATES PATENT AND TRADEMARK OFFICE
CERTIFICATE OF CORRECTION

| | |
|---|---|
| PATENT NO. | : 11,944,682 B2 |
| APPLICATION NO. | : 17/248369 |
| DATED | : April 2, 2024 |
| INVENTOR(S) | : Benzhong Tang and Xuewen He |

It is certified that error appears in the above-identified patent and that said Letters Patent is hereby corrected as shown below:

On the Title Page

In item (73) – Assignee, the correct Assignee's Name should read --The Hong Kong University of Science and Technology-- instead of "The Hong Kong University of Science and Technologyy".

Signed and Sealed this
Seventh Day of May, 2024

*Katherine Kelly Vidal*

Katherine Kelly Vidal
*Director of the United States Patent and Trademark Office*